(12) United States Patent
Driguez et al.

(10) Patent No.: US 10,772,946 B2
(45) Date of Patent: Sep. 15, 2020

(54) IMMUNOGENIC COMPOSITIONS AGAINST S. AUREUS

(71) Applicant: SANOFI PASTEUR, Lyons (FR)

(72) Inventors: Pierre-Alexandre Driguez, Le Mesnil le Roi (FR); Nathalie Guillo, Paris (FR); Bachra Rokbi, Lyons (FR); Noëlle Mistretta, Sain Bel (FR); Philippe Talaga, Sainte Consorce (FR)

(73) Assignee: SANOFI PASTEUR, Lyons (FR)

( * ) Notice: Subject to any disclaimer, the term of this patent is extended or adjusted under 35 U.S.C. 154(b) by 139 days.

(21) Appl. No.: 15/764,337

(22) PCT Filed: Oct. 13, 2016

(86) PCT No.: PCT/EP2016/074598
§ 371 (c)(1),
(2) Date: Mar. 29, 2018

(87) PCT Pub. No.: WO2017/064190
PCT Pub. Date: Apr. 20, 2017

(65) Prior Publication Data
US 2018/0280491 A1    Oct. 4, 2018

(30) Foreign Application Priority Data

Oct. 13, 2015  (EP) .................................... 15306621

(51) Int. Cl.
*A61K 39/085*   (2006.01)
*A61K 39/39*    (2006.01)
*A61K 39/00*    (2006.01)

(52) U.S. Cl.
CPC ............ *A61K 39/085* (2013.01); *A61K 39/39* (2013.01); *A61K 2039/55566* (2013.01); *A61K 2039/55572* (2013.01); *A61K 2039/575* (2013.01); *A61K 2039/60* (2013.01); *A61K 2039/6037* (2013.01)

(58) Field of Classification Search
None
See application file for complete search history.

(56) References Cited

FOREIGN PATENT DOCUMENTS

| EP | 2 848 257 A2 | 5/2013 |
|----|--------------|--------|
| WO | 2007/053176 A2 | 4/2006 |
| WO | 2006/065553 A2 | 6/2006 |

OTHER PUBLICATIONS

Sanchez-Trincado et al (Journal of Immunology Research (vol. 2017, Article ID 2680160, 14 pages.*
Livingstone et al Ann. Rev. Immunol. 5:477-501, 1987.*
International Search Report, dated Dec. 19, 2016, for Application No. PCT/EP2016/074598.
European Search Report, dated Mar. 4, 2016, for Application No. EP 15 30 6621.
Haensler, J. et al: "Design and preclinical characterization of a novel vaccine adjuvant formulation consisting of a synthetic TLR4 agonist in a thermoreversible squalene emulsion", International Journal of Pharmaceutics, Elsevier BV, NL, vol. 486, No. 1-2, Mar. 17, 2015 (Mar. 17, 2015), pp. 99-111, XP002741645.
Takahashi, K. et al: "Intradermal Immunization with Wall Teichoic Acid (WTA) Elicits and Augments an Anti-WTA IgG Response that Protects Mice from Methicillin-Resistant *Staphylococcus aureus* Infection Independent of Mannose-Binding Lectin Status", PLOS ONE, vol. 8, No. 8, Aug. 2, 2013 (Aug. 2, 2013). p. e69739, XP055255500.
Winstel, V. et al: "Pathways and roles of wall teichoic acid glycosylation in *Staphylococcus aureus*", International Journal of Medical Microbiology, vol. 304, No. 3-4, May 1, 2014 (May 1, 2014), pp. 215-221, XP055255503.
Fowler, V. G. et al: "Where does a *Staphylococcus aureus* vaccine stand?", Clinical Microbiology and Infection, vol. 20, May 1, 2014 (May 1, 2014), pp. 66-75, XP055255510.

* cited by examiner

*Primary Examiner* — Patricia Duffy
(74) *Attorney, Agent, or Firm* — Ladas & Parry LLP; Malcolm J. MacDonald

(57) ABSTRACT

The invention relates to a conjugate of a saccharide covalently bound to a carrier protein, wherein the saccharide comprises repetitive units of 1,5 ribitol phosphate in which all the ribitol residues are substituted by N-acetyl D-glucosaminyl residues at the 4-position, and wherein said N-acetyl D-glucosaminyl residues are exclusively in anomeric configuration α or are exclusively in anomeric configuration β and wherein the carrier protein provides at least one epitope to the conjugate which is recognized by T helper lymphocytes.

32 Claims, 6 Drawing Sheets

IMMUNOGENIC COMPOSITIONS AGAINST *S. AUREUS*

FIELD OF THE INVENTION

The present invention relates to immunogenic compositions that induce a cross reactive antibody response against *S. aureus* strains, methods for preparing such compositions and methods of use.

BACKGROUND OF THE INVENTION

*Staphylococcus aureus* (*S. aureus*) is an opportunistic bacterial pathogen that may cause a variety of diseases in humans ranging from moderate to severe skin and soft tissue infections to very serious diseases such as septic shock, toxic shock syndrome or pneumonia. Some of these infections may be fatal, in particular hospital-associated infections, which are often complicated by the fact that many hospital strains are resistant to antibiotics such as methicillin. Different strategies to prevent and/or treat *S. aureus* infections by passive immunization through the use of therapeutic antibodies or active immunization by vaccination are currently under development. Virulence factors of *S. aureus* are potent vaccine targets. However, it is likely that monovalent vaccine targeting only one virulence factor will not be enough to prevent *S. aureus* infections because the bacteria have developed different strategies to evade the host immune system. Antigenic variability among *S. aureus* strains or even during the life of the bacteria is another strategy. For instance, the capsular polysaccharide of *S. aureus* which is a well-known virulence factor is subject to variations among strains. Type 5 *S. aureus* strains express a type 5 capsular polysaccharide made of repeating units having the following structure: →4)-β-D-ManNAcA-(1→4)-α-L-FucNAc(3OAc)(1→3)-β-D-FucNAc-(1→while Type 8 *S. aureus* strains express a type 8 capsular polysaccharide made of repeating units having the following structure: →3)-β-D-ManNAcA(4OAc)-(1→3)-α-L-FucNAc(1→3)-α-D-FucNAc-(1→. Type 5 and type 8 strains account for approximately 88% of all clinical isolates. The remaining isolates that do not express type 5 or type 8 capsular polysaccharide have been described as carrying an antigen called the 336 antigen. The 336 antigen as described in WO 2007/053176 is a teichoic acid like structure comprising repeating units of 1,5 ribitol phosphate in which the 3-position of the ribitol is substituted by N-acetyl-β-D-glucosaminyl residues. Following the failure of a bivalent vaccine (staphVAX) comprising type 5 and type 8 capsular polysaccharides conjugated to a carrier protein in a phase III clinical trial, a second generation staphVAX vaccine is being developed, which comprises the 336 antigen in addition to the *S. aureus* type 5 and type 8 antigens and which is intended to provide a better coverage of clinical isolates than the previous version. This evolution of the staphVAX vaccine reflects the current strategy for *S. aureus* vaccine development which is to include more and more antigens in the vaccine composition in order to overcome the immune evasion mechanisms and the antigenic variability among *S. aureus* strains. Nevertheless there is a need to rationalize as much as possible the number of antigens to be included in the vaccine composition to limit the costs associated with the development and production of a multivalent vaccine. The identification of antigens that induce cross reactive antibodies recognizing both homologous and heterologous antigenic structures that are broadly expressed among *S. aureus* strains could be an efficient way to reduce the number of antigens to be combined in a vaccine against *S. aureus*. In this regard, WO 2007/057176 describes a conjugate form of the 336 antigen that elicits cross reactive antibodies that bind to both the homologous 336 antigen and the heterologous PS1 polysaccharide from *Staphylococcus epidermidis* (*S. epidermidis*). While this conjugate elicits inter species cross reactive antibodies (since the antibodies recognizes a heterologous antigenic structure expressed by *S. epidermidis*), there is no clear evidence that the antibodies recognize heterologous antigenic structures expressed by *S. aureus* strains.

EP 2848257 proposes a vaccine composition for preventing *Staphylococcus aureus* infection comprising a native form of WTA containing a ribitol-phosphate which has been modified by N-acetylglucosamine (GlcNAc), which comprises, as an active ingredient:

(i) a ribitol-phosphate which has been modified only by GlcNAc in a β-configuration and not by GlcNAc in an α-configuration;

(ii) a repeating unit of the ribitol-phosphate which has been modified only by GlcNAc in a β-configuration and not by GlcNAc in an α-configuration; or (iii) wall teichoic acid (WTA) containing the repeating unit of the ribitol-phosphate which has been modified only by GlcNAc in a β-configuration and not by GlcNAc in an α-configuration.

In the representation provided in FIG. 3 of this patent application, the GlcNAc is at position 2 of the ribitol-phosphate units. In order to improve its antigenicity, a carrier or an adjuvant can be added.

WO 2006/065,553 discloses glycoconjugate vaccines comprising a therapeutically effective amount of a capsular polysaccharide of *S. aureus* conjugated to a carrier protein, where the polysaccharide comprises an amount of peptidoglycan (e.g. at least about 5% (w/w)), which is effective to enhance properties of the vaccine, for example by improved conjugation efficiency of the polysaccharide to the carrier protein or by enhanced immunogenicity of the vaccine.

The inventors have now identified new antigenic structures that elicit cross reactive antibodies recognizing heterologous antigenic structures expressed by *S. aureus* strains so that the antibodies induced by such antigenic structures recognize a broad panel of *S. aureus* strains. Accordingly these new antigenic structures represent useful candidate vaccines since they contribute to the reduction of the number of antigens to be incorporated in an *S. aureus* vaccine.

SUMMARY OF THE INVENTION

The subject matter of the present invention is therefore:

A conjugate of a saccharide covalently bound to a carrier protein, wherein the saccharide comprises repetitive units of 1,5 ribitol phosphate in which all the ribitol residues are substituted by N-acetyl D-glucosaminyl residues at the 4-position, and wherein said N-acetyl D-glucosaminyl residues are exclusively in anomeric configuration α or are exclusively in anomeric configuration β.

In another embodiment the subject matter of the invention is a conjugate of a saccharide covalently bound to a carrier protein, wherein the saccharide consists of repetitive units of 1,5 ribitol phosphate in which all the ribitol residues are substituted by N-acetyl D-glucosaminyl residues at the 4-position, wherein said N-acetyl D-glucosaminyl residues are exclusively in anomeric configuration α or are exclusively in anomeric configuration β.

In a first aspect the saccharide according to the invention is extracted from the cell wall of *S. aureus*.

In another aspect the saccharide is obtained by chemical synthesis.

Typically, all the repetitive units of the saccharide have the following structure, or a salt thereof:

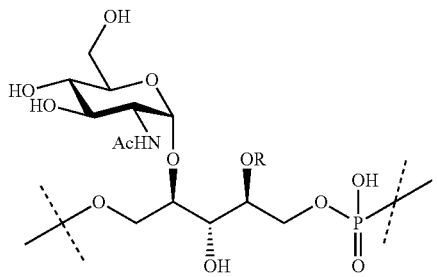

wherein:
R is independently H or D-Ala, and wherein R may be different from one repetitive unit to another, and
the N-acetyl D-glucosaminyl residue is in anomeric configuration α. Preferably, all the repetitive units of the saccharide have the following structure, or a salt thereof:

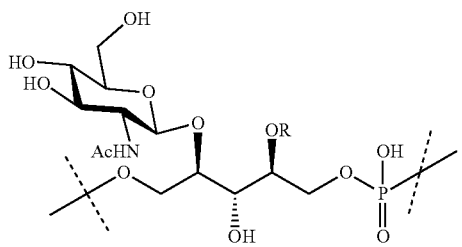

wherein:
R is independently H or D-Ala, and wherein R may be different from one repetitive unit to another, and
the N-acetyl D-glucosaminyl residue is in anomeric configuration β.

In a preferred embodiment the R group of the repetitive units of the saccharide is H.

In another aspect, the number of the repetitive units is ≥ 4, preferably between 4 and 14, more preferably equal to 6, 7, 8, 9, 10, 11, or 12.

Typically, the saccharide according to the invention is covalently bound to the carrier protein via a linker.

In a particular aspect, the carrier protein is linked to the terminal phosphate of the saccharide according to the invention, preferably via a linker.

In a preferred aspect, the conjugate according to the invention has the following structure:

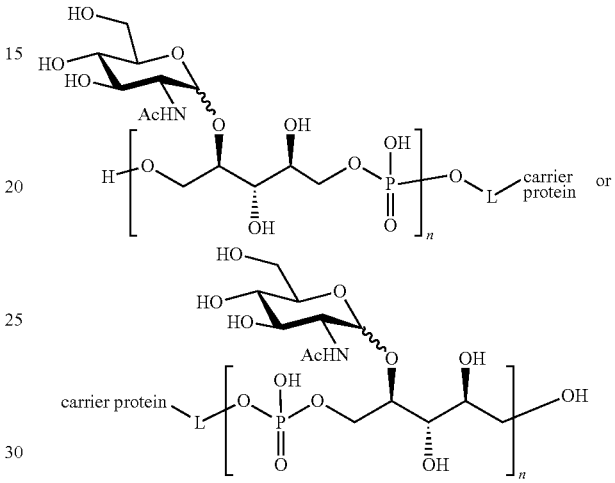

wherein:
the N-acetyl D-glucosaminyl residues are exclusively in anomeric configuration α or exclusively in anomeric configuration β;
n is an integer≥4, n being preferably between 4 and 14, more preferably n being 6, 7, 8, 9, 10, 11, or 12; and
L is a linker;
or a salt of one of these structures.

In a further aspect, the conjugate has the following structure:

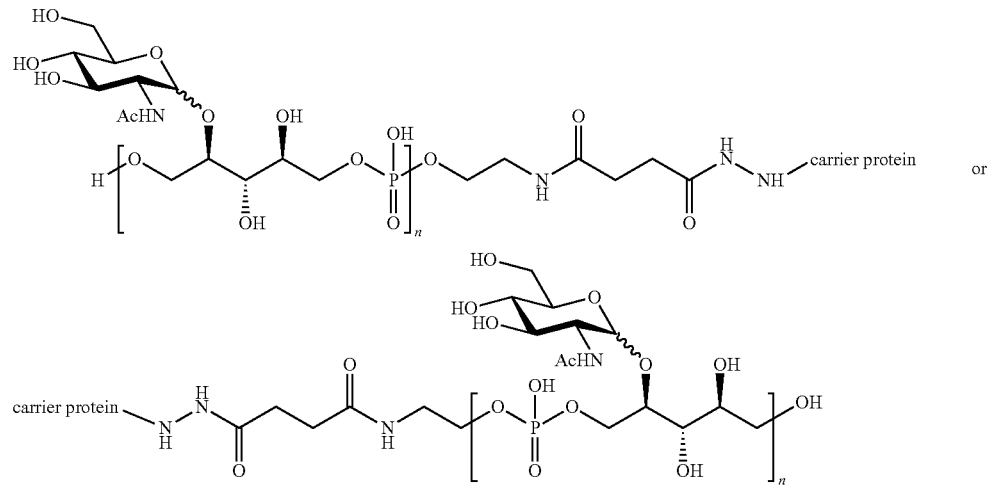

wherein:
the N-acetyl D-glucosaminyl residues are exclusively in anomeric configuration α or exclusively in anomeric configuration β;
n is an integer≥4, n being preferably between 4 and 14, more preferably n being 6, 7, 8, 9, 10, 11, or 12;
or a salt of one of these structures.

In a preferred aspect, a conjugate according to the invention comprises repetitive units of 1,5 ribitol phosphate in which all the ribitol residues are substituted by N-acetyl D-glucosaminyl residues at the 4-position and wherein wherein said N-acetyl D-glucosaminyl residues are exclusively in anomeric configuration β.

In a preferred embodiment, a conjugate according to the present invention comprises less than 5% w/w peptidoglycan. Advantageously, a conjugate according to the present invention comprises less than 4% w/w, less than 3% w/w, less than 2% w/w, less than 1% or 0% w/w peptidoglycan. Most preferably, a conjugate according to the present does not comprise any peptidoglycan (i.e. 0% w/w).

In a further embodiment, the carrier protein of the conjugate according to the invention is a detoxified bacterial toxin.

In a further aspect the detoxified bacterial toxin is Exoprotein A of *Pseudomonas aeruginosa*. Preferably said Exoprotein A is recombinant Exoprotein A (rEPA).

In a further preferred aspect the detoxified bacterial toxin is a hemolysin of *S. aureus* (Hla).

In another embodiment, the weight ratio between the saccharide and the carrier protein is between 0.1 and 10.

In yet another preferred embodiment, the invention concerns a composition comprising
a conjugate according to the invention and an adjuvant.
Typically, the adjuvant is a TLR4 agonist.
More particularly, the adjuvant is a TLR4 agonist in combination with a delivery system such as an oil in water emulsion or aluminium salts.
More specifically, the TLR4 agonist is E6020 (CAS number: 287180-63-6).

In another aspect, the adjuvant is a Th1, a Th17, or Th1/Th17 adjuvant.

In another aspect, the conjugate of the invention induces the production of antibodies that binds to both *S. aureus* type 336 strain deposited under ATCC (American Type Culture Collection) number 55804, Wood 46 strain of *S. aureus* deposited under ATCC number 10832 and the Newman D2C strain deposited under ATCC number 25904.

In another aspect, the subject matter of the invention relates to a method for preparing a conjugate according to the invention including a linker comprising:
a) providing a saccharide that comprises or consists of repetitive units of 1,5 ribitol phosphate in which all the ribitol residues are substituted by N-acetyl D-glucosaminyl residues at the 4-position, and wherein said N-acetyl D-glucosaminyl residues are exclusively in anomeric configuration α or are exclusively in anomeric configuration β,
b) providing a carrier protein,
c) derivatizing said saccharide with a linking agent and coupling the derivatized saccharide with said carrier protein or alternatively, derivatizing said carrier protein with a linking agent and coupling the derivatized carrier protein to said saccharide to obtain the conjugate.

In a particular aspect, the linking agent for derivatizing the saccharide may be a dihydrazide such as adipic acid dihydrazide when the saccharide according to the invention is extracted from the cell wall of *S. aureus*. Alternatively, when the saccharide according to the invention is obtained by chemical synthesis, the saccharide may be derivatized using a di-activated diester such as disuccinimidyl succinate followed by treatment with hydrazine.

Steps a) and b) may respectively include the preparation of the saccharide or of the carder.

In another embodiment a method for preparing a conjugate according to the invention including a linker comprises:
a) providing a saccharide that comprises or consists of repetitive units of 1,5 ribitol phosphate in which all the ribitol residues are substituted by N-acetyl D-glucosaminyl residues at the 4-position, and wherein said N-acetyl D-glucosaminyl residues are exclusively in anomeric configuration α or are exclusively in anomeric configuration β,
b) providing a carrier protein,
c) derivatizing said saccharide with a first linking agent,
d) derivatizing said carrier protein with a second linking agent, and
e) coupling said derivatized saccharide to said derivatized carrier protein to obtain the conjugate.

Steps a) and b) may respectively include the preparation of the saccharide or of the carder.

In a particular aspect, the linking agent for derivatizing the saccharide is cystamine, and the linking agent for derivatizing the carrier protein is γ-maleimidobutyric acid N-hydroxysuccinimide ester (GMBS) or succinimidyl-3 (bromoacetamido) propionate (SBAP).

In a preferred embodiment of these methods, the saccharide comprises or consists of repetitive units of 1,5 ribitol phosphate in which all the ribitol residues are substituted by N-acetyl D-glucosaminyl residues at the 4-position, and wherein said N-acetyl D-glucosaminyl residues are exclusively in anomeric configuration β. Advantageously, the carrier protein is linked to the terminal phosphate of the saccharide according to the invention, preferably via a linker.

In a further aspect, the method of the invention further comprises adding an adjuvant to the conjugate to form a composition.

In a yet another embodiment, the subject matter of the invention relates to an immunogenic composition comprising the conjugate according to the invention for use in an individual at risk of *S. aureus* infection, wherein said composition induces in said individual the production of cross reactive antibodies against *S. aureus* strains.

In a first aspect, the cross reactive antibodies bind to a *S. aureus* type 336 strain, such as the *S. aureus* type 336 strain deposited under ATCC number 55804.

In a further aspect, the cross reactive antibodies further bind to the Wood 46 strain of *S. aureus* deposited under ATCC number 10832 and the Newman D2C strain of *S. aureus* deposited under ATCC number 25904.

Lastly, the subject matter of the invention relates to a method of inducing cross reactive antibodies against *S. aureus* strains in an individual at risk of *S. aureus* infection comprising administering to said individual an immunogenic composition comprising the conjugate according to the invention.

Definitions

In the context of the present invention, the terms as cited below have the following meanings:

The word "comprise" may have the meanings "include", "contain" or "consist of". On the other hand, "consist of"

means "consist exclusively of" and excludes the addition of a component which is not listed.

"A saccharide" in the meaning of the invention encompasses both a polysaccharide and an oligosaccharide and refers to a molecule containing more than one saccharide sub-unit. In particular, the saccharide used in the conjugate of the invention comprises or consists of several ribitol phosphate repeating units as defined throughout the specification. Usually when the number of repeating units is ≤11, the saccharide is considered as an oligosaccharide and when the number of repeating units is >11, the saccharide is considered as a polysaccharide.

By "salt form" of the repetitive unit or of the conjugate, we mean a pharmaceutically acceptable salt of an anionic form of the conjugate with cation(s), for example with $Na^+$. In an aqueous solution with a pH close to 7, most of the time the phosphate groups of the saccharide will be in an anionic form, forming a salt with a cation which will be also present in the aqueous solution. In some cases phosphate groups of the saccharide may be exclusively in the acidic form or exclusively in the salt form. In other cases, some phosphate groups of the same saccharide may be in the acidic form and other phosphate groups in the salt form.

In the conjugate according to the invention, the saccharide is covalently bound to a protein carrier which comprises at least one epitope which is recognized by T helper lymphocytes. The T helper lymphocytes are also called T helper cells. An epitope which is recognized by T helper lymphocytes is called a "T helper epitope". In particular, a "T-helper epitope" activates T-helper lymphocytes via presentation of the epitope on the surface of an antigen-presenting cell (APC) together with a major histocompatibility complex (MHC) class II molecule.

The saccharide alone is poorly immunogenic. According to the invention, the immunogenic response to the saccharide is improved by conjugating the saccharide to an immunocarrier ie the carrier protein. It is thought that the saccharide alone induces a T cell-independent response when presented without a covalently attached carrier protein. The T cell-independent response results in short lived antibody responses characterized by low affinity antibodies predominated by IgM. Conjugation of a carrier protein to the saccharide provides at least one T cell epitope to the saccharide. This converts the T cell-independent response to a T cell-dependent response. According to the invention, the carrier protein of the conjugate results in the development of a T lymphocytes dependent immunity specific for the saccharide as defined throughout the invention with production of antibodies that bind to (or recognize) the saccharide. Advantageously, it also induces a stronger and faster secondary antibody response against the saccharide after a boost immunization (boost effect). In particular, upon uptake of the conjugate by B cells specific for the saccharide, the T cell epitope is displayed on the surface of the B cell along with one or more MHC, and in particular MHC class II, for interaction with T helper cells. Therefore, B cells that secrete antibodies to the saccharide are expanded in a T cell-dependent manner.

"A carrier protein" in the meaning of the invention comprises a chain of amino acids, whatever its size and the post-translational modifications. The carrier protein can be a peptide (corresponding of an amino acid chain of at most 100 amino acids), but preferably it is a protein (comprising an amino acid chain of more than 100 amino acids). In particular, the carrier protein comprises at least one chain of amino acids which is a T-helper epitope. The size of a T-helper epitope is at least 10-15 amino acids. The protein carrier may contain multiple T cell epitopes.

A "conjugate" in the meaning of the invention refers to a combination of a saccharide and a peptide or protein linked by a covalent bond. The term "conjugate" encompasses hemi-synthetic and/or synthetic compounds, but preferably excludes compounds which are present in nature, whether they are made by synthetic or hemisynthetic routes or naturally. The conjugate is the result of the conjugation of the saccharide to the protein, generally via a linker.

In the context of the present invention at least the conjugation process, i.e. the steps that ensure the linkage between the saccharide and the carrier protein, are carried out by chemical synthesis. In the context of the present invention, a conjugate is considered to be a hemi-synthetic compound when the saccharide and/or the carrier protein are of natural origin and only the conjugation process is performed by chemical synthesis, thus forming a compound that is not found in nature. The conjugate is a synthetic compound when the saccharide and the carrier protein are produced by chemical synthesis and the conjugation process is also performed by chemical synthesis. For the sake of clarity, a conjugate that is a product of nature is excluded from the scope of the invention. For instance, wall teichoic acids (WTAs) which are composed of teichoic acids (TAs) linked to peptidoglycan (PG) (insofar as PG could be considered as a carrier protein), are natural components of the cell wall of $gram^+$ bacteria, in particular WTAs of S. aureus, and are excluded from the field of the invention, as they do not include a T-helper epitope.

The term "linker" refers to the additional chemical structure located between the saccharide and the carrier protein in the completed conjugate, which results from the indirect linkage of the saccharide to the carrier protein and involves one or several linking agents having two functional reactive groups.

"Adjuvant", as used herein, refers to agents or substances that modulate the immunogenicity of an antigen. "Modulate the immunogenicity" includes enhancing the magnitude and/or duration of an immune response generated by an antigen. The terms "functional reactive group", comprises "active moiety", "activating group", "reactive site", "chemically reactive group" and "chemically reactive moiety" which are used in the art and herein refer to distinct, definable portions or units of a molecule. The terms are somewhat synonymous in the chemical arts and are used herein to indicate the portions of molecules that are reactive with other molecules. The term "active", when used in conjunction with functional groups, is intended to include those functional groups that react readily with electrophilic or nucleophilic groups. For example, as would be understood in the art, the term "active or activated ester" would include those esters that react readily with nucleophilic groups such as amines.

"Cross reactive antibodies" denote antibodies that bind to the antigenic structure against which they have been initially generated, which is referred to as the homologous antigenic structure or homologous antigen, but also to one or several other antigenic structures that are structurally distinct from the homologous antigenic structure, which are referred to as heterologous antigenic structures or heterologous antigens. By extension, a S. aureus strain that expresses a homologous antigenic structure is referred to as a "homologous strain" whereas a S. aureus strain that expresses a heterologous antigenic structure is referred to as a "heterologous strain".

The term "individual" refers to a human being or an animal selected among the canine, the feline, the bovine, the porcine, the equine, the ovine species as well as the mustelids and the avian species.

DETAILED DESCRIPTION OF THE INVENTION

Figure 1:
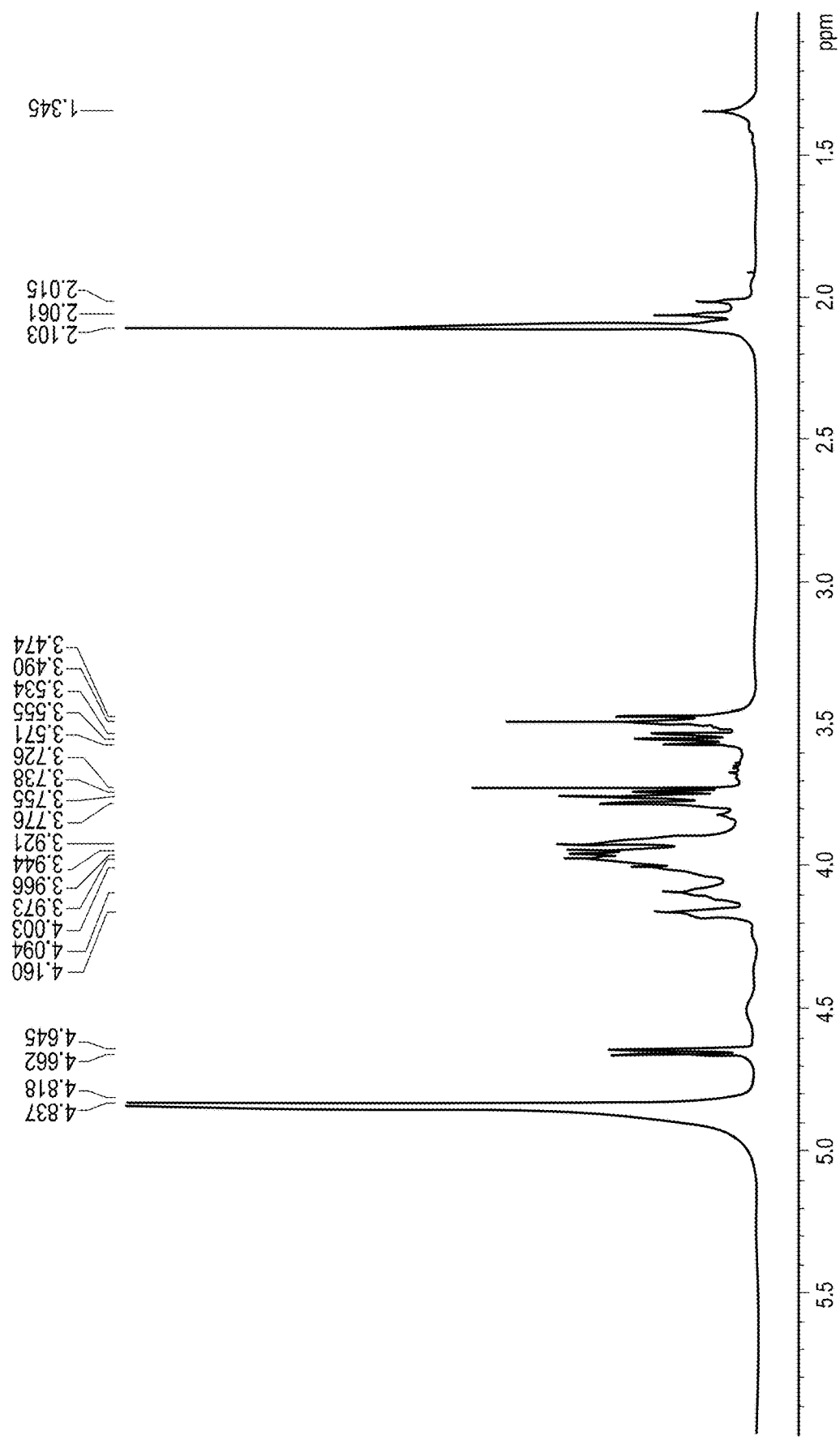
FIG. 1 is the 500 MHz $^1$H NMR spectrum of the purified β(1,3) TA from strain ATCC 55804 in $D_2O$ at 293K.

The inventors have surprisingly found that a conjugate of a saccharide covalently bound to a carrier protein, wherein the saccharide comprises repetitive units of 1,5 ribitol phosphate in which all the ribitol residues have been substituted by N-acetyl D-glucosaminyl residues at the 4-position, and wherein said N-acetyl D-glucosaminyl residues are exclusively in anomeric configuration α or are exclusively in anomeric configuration β, induces cross reactive antibodies that recognize a broad panel of *S. aureus* strains showing evidence of antigenic variations between the strains. To this end, the structure of the ribitol phosphate repeating units of the wall teichoic acid (WTA) from a panel of 20 *S. aureus* strains cultivated overnight in a Tryptic Soy Broth (TSB) was analyzed. The WTA of *S. aureus* is made of a teichoic acid moiety covalently linked to the peptidoglycan. The chemical structure of the teichoic acid moiety (TA) of *S. aureus* was reported in Int. J. Med. Microbiol 300 (2010), 148-154; and Nature Reviews Microbiology, 6 (2008), 276-286 as being composed of a disaccharide linkage unit and a main chain polymer composed of 11 to 40 ribitol-phosphate repeating units in which the hydroxyl groups on the ribitol phosphate repeating units have been tailored with cationic D-alanine esters and N-acetyl glucosaminyl residues. The disaccharide linkage unit is composed of N-acetylmannosamine β (1-3)-N-acetylglucosamine 1-phosphate with two glycerol 3-phosphate units attached to the C4 hydroxyl of the N-acetylmannosamine.

In the present study the exact nature of the N-acetyl glucosamine linkage to the ribitol residues of the ribitol phosphate repeating units was determined for each of the 20 strains by carbotyping using High Performance Anion Exchange Chromatography with pulsed Amperometry Detection (HPAEC-PAD) after acid treatment with hydrogen fluoride (see paragraph I in the "Examples" section). In parallel, the capsular polysaccharide expression of each strain was also measured by flow cytometry using a polyclonal serum specific for type 5 or specific for type 8 capsular polysaccharide of *S. aureus*.

The strain typing results are presented in the table below.

| Identification of the strain | Origin | category | Phenotype of the capsule | Biochemical characterization of the ribitol phosphate units | | |
|---|---|---|---|---|---|---|
| | | | | βGlcNAc (1-3) | βGlcNAc (1-4) | αGlcNAc (1-4) |
| HT2005 0769 | Clin. Isol. | 100% β(1-3) | (PS5) | 100% | | |
| HT2005 0667 | Clin. Isol. | 100% β(1-3) | (PS5) | 100% | | |
| ATCC 55804 | Cell collection | 100% β(1-3) | Neg. | 100% | | |
| Xen36 | Cell. Collection | 100% β(1-4) | (PS8) | | 100% | |
| HT2005 0662 | Clin. Isol. | 100% β(1-4) | (PS5) | | 100% | |
| HT2005 0499 | Clin. Isol | 100% β(1-4) | (PS5) | | 100% | |
| HT2005 0742 | Clin. Isol | 100% β(1-4) | (PS5) | | 100% | |
| HT2005 0659 | Clin. Isol | 100% β(1-4) | (PS5) | | 100% | |
| HH0528 1156 | Clin. Isol | 100% α(1-4) | Neg | | | 100% |
| Newman D2C ATCC25904 | Cell Collection | 100% α(1-4) | (PS5) | | | 100% |
| HT2005 0843 | Clin. Isol | 100% α(1-4) | (PS5). | | | 100% |
| Newman Foster NCTC8178 | Cell collection | Mix α(1-4) and β(1-4) | (PS5) | | 10% | 90% |
| HT2005 0837 | Clin. Isol | Mix α(1-4) and β(1-4) | Neg. | | 20% | 80% |
| Newman spa::KaR | Cell Collection | Mix α(1-4) and β(1-4) | (PS5) | | 30% | 70% |
| HT2005 0756 | Clin. Isol | Mix α(1-4) and β(1-4) | (PS5) | | 30% | 70% |
| HT2005 0702 | Clin. Isol | Mix α(1-4) and β(1-4) | (PS8) | | 60% | 40% |
| HT2005 0689 | Clin. Isol | Mix α(1-4) and β(1-4) | (PS5) | | 60% | 40% |

|                         |           |                        | Phenotype        | Biochemical characterization of the ribitol phosphate units | | |
| Identification of the strain | Origin | category | of the capsule | βGlcNAc (1-3) | βGlcNAc (1-4) | αGlcNAc (1-4) |
|---|---|---|---|---|---|---|
| HT2005 0828 | Clin. Isol | Mix α(1-4) and β(1-4) | Neg. | | 90% | 10% |
| HT2005 0704 | Clin. Isol | Mix α(1-4) and β(1-4) | (PS8) | | 90% | 10% |

These results clearly demonstrate that the structure of the repeating units of the TAs is highly heterogeneous among S. aureus strains.

As shown in the table, there are strains (referred to as "100% α(1-4) strains"), where the ribitol residues of the 1,5 ribitol phosphate repeating units are substituted at the 4-position by N-acetyl D-glucosaminyl residues which are all in the α anomeric configuration. There are also strains (referred to as "100% β(1-4) strains"), where the ribitol groups of the 1,5 ribitol phosphate repeating units are substituted at the 4-position by N-acetyl D-glucosaminyl residues which are all in the β anomeric configuration. There are also strains (referred to as "mix α (1-4) and β (1-4) strains"), where a part of the ribitol residues of the 1,5 ribitol phosphate repeating units are substituted at the 4-position by N-acetyl D-glucosaminyl residues which are in one specific anomeric configuration (α or β) while the remaining part of the ribitol residues are substituted at the 4-position by N-acetyl D-glucosaminyl residues in the other specific anomeric configuration (β or α). Lastly, there are strains (referred to as "100% β(1-3) strains"), where the ribitol residues of the 1,5 ribitol phosphate repeating units are substituted at the 3-position by N-acetyl D-glucosaminyl residues which are all in the β anomeric configuration.

A conjugate of a polysaccharide and a carrier protein corresponding to the 336 conjugate described in WO 2007/053176 (wherein the polysaccharide is made of 1,5 ribitol phosphate repeating units which are substituted at the 3-position by N-acetyl D-glucosaminyl residues in a β anomeric configuration) induces antibodies that recognize almost exclusively "100% β(1-3) strains" which express the homologous antigenic structure. In contrast, a saccharide-carrier protein conjugate, wherein the saccharide comprises repetitive units of 1,5 ribitol phosphate in which all the ribitol residues are substituted at the 4-position by N-acetyl D-glucosaminyl residues in anomeric configuration β, induces antibodies that recognize the homologous "100% β(1-4) strains", but also "mix α (1-4) and β-4) strains", "100% α(1-4) strains" and "100% β(1-3) strains" which express heterologous antigenic structures. Similarly, a saccharide-carrier protein conjugate, wherein the saccharide comprises repetitive units of 1,5 ribitol phosphate in which all the ribitol residues are substituted at the 4-position by N-acetyl D-glucosaminyl residues in anomeric configuration α, induces antibodies that recognize the homologous "100% α(1-4) strains", but also "mix α (1-4) and β (1-4) strains", "100% β(1-4) strains" and "100% β(1-3) strains" which express heterologous antigenic structures (see paragraph VII of the Examples section).

Therefore, with the goal of rationalizing the number of antigenic components to be included in a vaccine against S. aureus, a conjugate of a saccharide covalently bound to a carrier protein, wherein the saccharide comprises or consists of repetitive units of 1,5 ribitol phosphate in which all the ribitol residues are substituted at the 4-position by N-acetyl D-glucosaminyl residues which are exclusively in anomeric configuration β or exclusively in anomeric configuration α, is especially suitable since it induces cross reactive antibodies that recognize a broad panel of S. aureus strains, while contrary to expectations, a conjugate of a carrier protein and a polysaccharide comprising repetitive units of 1,5 ribitol phosphate in which the 3-position of the ribitol residues are substituted by N-acetyl D-glucosaminyl residues in anomeric configuration β does not.

Preparation and Features of the Saccharide

The saccharide used in the preparation of the conjugate according to the invention can be extracted and purified from the wall teichoic acids (WTA) of "100% α(1-4) strains" or "100% β(1-4) strains" available, for example, from cell collections. An example of a "100% α(1-4) strain" is the Newman D2C strain with deposit number ATCC 25904. An example of a "100% β(1-4)" strain is the Wood 46 strain with deposit number ATCC10832.

Following fermentation, cells are killed and then harvested by centrifugation. The saccharide is then extracted from the cell paste by enzyme treatment with lysostaphin, nuclease treatment such as benzonase, pronase treatment followed by conventional sequential precipitation with 25-75% cold ethanol/$CaCl_2$. The 75% ethanol precipitate contains the crude saccharide extract which is subsequently purified by well-known separation methods such as size exclusion chromatography or ion exchange chromatography. The fractions that contain the saccharide as defined in the invention are then dialyzed and lyophilized.

The saccharide obtained at the end of the purification process comprises generally more than 15 repetitive units of 1,5 ribitol phosphate in which all the ribitol residues at the 4-position are substituted by N-acetyl D-glucosaminyl residues that are all in anomeric configuration α or all in anomeric configuration β according to the features of the original strain used. The 2-position of the ribitol groups may also be randomly substituted by D-Alanine (D-Ala), but preferably the ribitol residues are not substituted by any chemical residue at the 2-position. Typically, the saccharide is a polysaccharide since the number of the repetitive units in the polysaccharide chain is between 20 and 40 repetitive units. If desired, the number of the repetitive units can be reduced by mild alkaline or acid treatments or an oxidation-reduction depolymerization reaction. The repetitive units of 1,5 ribitol phosphate in which all the ribitol residues at the 4-position are substituted by N-acetyl D-glucosaminyl residues are all in anomeric configuration α or are all in anomeric configuration β and are generally covalently linked to two glycerol phosphate residues, which are themselves linked to the N-acetylmannosamine-(β1,3)-N-acetyl-glucosamine 1-phosphate disaccharide via the the C4 hydroxyl of the N-acetylmannosamine residue as it is depicted in the teichoic acid structure of S. aureus. Ultimately, the complete chemical structure of the native saccharide extracted and purified from a "100% α(1-4) strain" or a "100% β(1-4) strain" is generally equivalent to the corresponding teichoic acid (TA) structure of the strain from which it has been purified. Therefore, the saccharide portion of the conjugate that is obtained by conjugation to a carrier protein comprises repetitive units of 1,5 ribitol phosphate in which all the ribitol residues are substituted at the 4-position by N-acetyl D-glucosaminyl residues that are exclusively in anomeric configuration α or exclusively in anomeric configuration β.

Advantageously, in another way, the saccharide for preparing the conjugate according to the invention is obtained in a reproducible way by chemical synthesis. The synthetic saccharide obtained at the end of the chemical process consists of repetitive units of 1,5 ribitol phosphate in which all the ribitol residues at the 4-position are substituted by N-acetyl D-glucosaminyl residues, which are exclusively in anomeric configuration α or exclusively in anomeric configuration β. The chemical structure of such a synthetic saccharide is as follows:

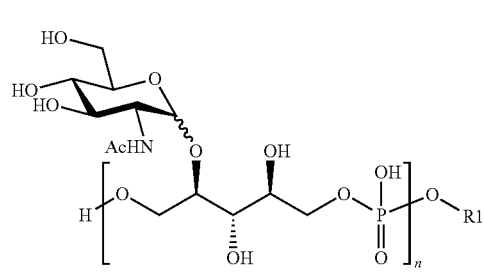

(I)

or

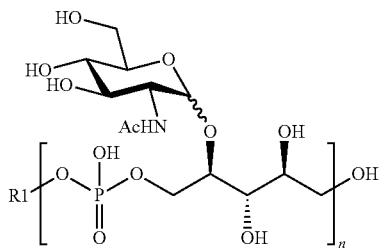

(II)

wherein:
the N-acetyl D-glucosaminyl residues are exclusively in configuration α or exclusively in configuration β;
n is at least 4; and
R1 is either H, an alkyl amine or an alkyl hydrazide,
or a salt of one of these structures.

The synthetic saccharide obtained at the end of the process can be an oligosaccharide or a polysaccharide. Advantageously, it contains at least 4 units of 1,5 ribitol phosphate, but more preferably it contains 5, 6, 7, 8, 9, 10 or 11 units of 1,5 ribitol phosphate. However, if desired, the synthetic saccharide can contain more than 15 repetitive units according to the invention. Typically, the synthetic saccharide obtained at the end of the synthesis process consists of 6 to 12 repetitive units of ribitol phosphate.

The synthesis process involves a step of preparing a fully protected equivalent of the desired synthetic saccharide. The synthesis of the fully protected equivalent is performed according to methods well known to those skilled in the art and using methods for the synthesis of oligosaccharides [for example G. J. Boons, Tetrahedron (1996), 52, 1095-1121 or K. Toshima and K. Tatsuta, Chem. Rev. (1993), 93, 1503-1531], ribitol phosphate oligomers [A. Fekete et al, Carbohydrate Research (2006), 341, 2037-2048] and nucleic acid oligomers [Y. Hayakawa et al., J. Am. Chem. Soc. (2001), 123(34), 8165-8176]. An oligosaccharide donor is coupled with an oligosaccharide acceptor in the presence of chloro-2-cyanoethyl-N,N-diisopropylphosphoramidite to introduce a protected phosphate group between the two oligosaccharides as described for instance in Step 1.11 of Example no 1. The size of the resulting protected saccharide is equal to the sum of the sizes of the two reactive species. This coupling step is repeated until the number of the repetitive units of the protected saccharide corresponds to the number of the repetitive units that is desired in the synthetic saccharide. Several deprotection steps are then performed to obtain the desired synthetic saccharide.

When the desired synthetic saccharide is of formula (I), and wherein R1 is an alkyl amine or an alkyl hydrazide, this product can be obtained from a fully protected equivalent of the desired saccharide having for example the formula:

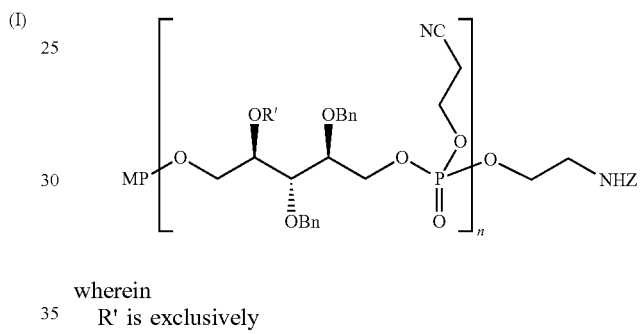

wherein
R' is exclusively

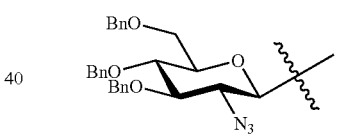

beta series or exclusively

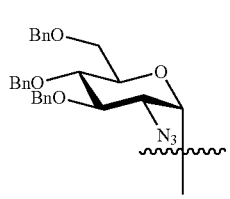

alpha series beta series alpha series
MP is para-methoxyphenyl,
n is at least 4;
Bn is benzyl, and
Z is benzyloxy-carbonyl,
followed by
1) eliminating the para-methoxyphenyl group,
2) eliminating cyanoethyl groups,
3) transforming azides into acetamido groups by reductive acetylation, 4) hydrogenolysing the benzyl ether and benzyloxycarbonyl groups, and optionally, 5) when R1 is an alkyl hydrazide, treating the saccharide obtained at the end of step 4) with disuccinimidyl succinate followed by hydrazine in order to introduce a hydrazide group.

Alternatively, step 3) can be performed before step 2).

Examples 1 to 3 detail the chemical steps leading to the preparation of oligosaccharides having 8 or 9 repetitive units, in which the protected N-acetyl D-glucosaminyl residues are exclusively in anomeric configuration α or are exclusively in anomeric configuration β. From these examples other protected oligosaccharides having a different number of repetitive units can be easily obtained.

When the desired synthetic saccharide is of formula (II), a similar synthetic route as the one described for the synthetic saccharide of formula (I) is adopted These synthetic saccharides have numerous advantages over those that have been extracted and purified from S. aureus strains, inter alia product homogeneity, avoidance of microbial contamination, and/or analytical issues. Furthermore and more importantly, we have been able to demonstrate that the repetitive units of 1,5 ribitol phosphate in which the ribitol residues at the 4-position are substituted by N-acetyl D-glucosaminyl residues that are exclusively in anomeric configuration α or exclusively in anomeric configuration β, which are the only antigenic structures of these synthetic saccharides, represent the necessary and effective antigenic structures to induce the development of a cross reactive antibody response as described in the present invention. Moreover, the lack of any other additional antigenic structure in the synthetic saccharides (as may be the case for saccharides extracted and purified from strains of S. aureus), eliminates the possible undesirable side effects associated with such additional antigenic structures, or the weakening of the cross reactive antibody response by dispersion of the immune response. For example, a conjugate according to the present invention preferably comprises less than 5% w/w peptidoglycan. Advantageously, a conjugate according to the present invention comprises less than 4% w/w, less than 3% w/w, less than 2% w/w, less than 1% or 0% w/w peptidoglycan. Most preferably, a conjugate according to the present does not comprise any peptidoglycan (i.e. 0% w/w).

The peptidoglycan (PG) content of a sample of polysaccharide can be expressed in terms of w/w % of certain amino acids, determined via amino acid analysis (AAA), conducted as follows. Briefly, a 1 mg/mL sample of purified polysaccharide in water is hydrolyzed with vapor phase hydrochloric acid. Reconstituted primary and secondary amino acids are converted to stable fluorescent derivatives that fluoresce strongly at 395 run. Analysis of the re-suspended protein hydrolysate is performed by reverse phase HPLC. The amino acids are quantified by means of external and internal standards. Amino acids present in the polysaccharide solution arise from (1) PG (residues Ala, Glx, Gly and Lys) and (2) residual proteins (residues Arg, Asx, He, Leu, Met, Phe, Ser, Thr, Thy, Val, His and Pro). Two amino acids (Cys and Trp) are not quantitated and are therefore not reported. The concentrations of the amino acids associated with PG and residual protein are reported as a mass percentage relative to the polysaccharide using the following equations:

Calculation for % Peptidoglycan (w/w):

$$\% \text{ Peptidoglycan} = [PG]/[CPS] \times 100$$

$$[PG] \text{mg/mL} = \text{Gln/Glu} + \text{Gly} + \text{Ala} + \text{Lys}$$

where:
[PG]=calculated peptidoglycan concentration of the sample (mg/mL)
[CPS]=known polysaccharide concentration of the sample (mg/mL)

Calculation for % Residual Protein (w/w):

$$\% \text{ RP} = (\text{peptides})_{cps} - [PG]/[CPS] \times 100$$

$$\Sigma(\text{Amino acids}) = (\text{peptides}) \text{cps where:}$$

(peptides)cps=Total peptide concentration
[RP]=Calculated residual protein concentration of sample (mg/mL)
[CPS]=Known polysaccharide concentration of sample (mg/mL)

Features of the Carrier Protein

The carrier protein as previously mentioned can be any peptide or protein provided it contains at least one T-Helper epitope. PADRE (Pan DR T-helper epitope) peptide described by Del guercio et al. [Vaccine (1997), Vol 15/4, 441-448] is an example of a useful carrier peptide. Alternatively Human Serum Albumin (HSA), Keyhole Limpet Haemocyanin (KLH) and viral or bacterial proteins are also useful carrier proteins. By way of example, reference is made to bacterial toxoids obtained by chemical detoxification such as tetanus toxoid or diphtheria toxoid or toxoids obtained by genetic mutation such as diphtheriae toxoid (CRM 197), the detoxified Streptococcus pneumominae pneumolysine (PlyD), the detoxified Bordetella pertussis toxin, the detoxified Pseudomonas aeruginosa exoprotein A or the non-toxic mutants of S. aureus exotoxin A. The outer membrane proteins of bacteria, such as OMP1 and OMP2 proteins of Neisseria meningitides, lambB, OmpC, OmpaA, OmpF and PhoE proteins of Escherichia coli, CotC and CotD proteins of Bacillus subtilis, the bacterial porins such as Neisseria meningitidis B Class 1 porin and Klebsiella pneumoniae porin P40; the lipoproteins such as Borelia burgdorfi OspA, Streptococcus pneumoniae PspA, Neisseria meningitidis Transferrin binding protein type 2 (TBP2), Escherichia coli TraT, Streptococcus pneumoniae adhesin A, the purified protein derivative of tuberculin (PPD), protein D of Haemophilus influenzae, as well as fragments of any of the above cited proteins (which contain at least one T-helper epitope) are also suitable carrier proteins.

Staphylococcal proteins or fragments thereof are also especially suitable carrier proteins as they can further contribute to the reduction of the number of antigens to be incorporated in a S. aureus vaccine. By way of example reference is made to extracellular component binding proteins of Staphylococcus such as laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin Binding protein, fibrinogen binding protein, coagulase, Fig and MAP. Staphylococcus transporter proteins like Immunodominant ABC transporter, IsdA, IsdB, Mg2+ transporter, SiTC and Ni ABC Transporter can also be used. Detoxified toxins of Staphylococcus such as alpha-toxin, hemolysins, panton-valentine leukocidin, enterotoxin B and TSST-1 or derivatives thereof as well as the staphylococcus proteins that regulate the production of toxins such as RNA III activating protein (RAP) are also suitable carrier proteins.

Preferably, the carrier protein of the conjugate according to the invention is a detoxified bacterial toxin or a derivative thereof that causes the development of a sustained T cell dependent immunity specific for the saccharide as defined in the invention. More specifically, the detoxified bacterial toxin can be selected from the group of toxins secreted by *Clostridium tetani, Clostridium diphtheriae, Pseudomonas aeruginosa* and *Staphylococcus aureus*. Unless the conjugation process itself is responsible for the detoxification of the bacterial toxin, usually the toxin is previously detoxified before carrying out the conjugation process between the carrier protein and the saccharide according to the invention. The detoxification of the bacterial toxin can be achieved by chemical treatment and/or heat treatment, as is usually the case for tetanus toxin or diphtheria toxin, or by genetic mutation. The genetic mutant CRM197 of the diphtheria toxin can be used as alternative to the chemically detoxified diphtheria toxin.

In a preferred embodiment, the carrier protein is the detoxified exoprotein A of *Pseudomonas aeruginosa* or a fragment thereof. A detoxified form of the exoprotein A of *Pseudomonas aeruginosa* can be obtained for instance by deletion of the binding domain I as described in WO 88/02401 or preferably by deletion mutation whereby Glutamic Acid in position 553 of the protein has been removed. The recombinant mutant protein, named rEPA 553D, produced for instance by a recombinant strain of *E. coli* carrying a plasmid expressing the mutant protein is devoid of toxicity due to the suppression of ADP-ribosylation catalytic activity and can also be used as carrier protein.

In another preferred embodiment, the carrier protein of the conjugate according to the invention is a detoxified α-hemolysin of *S. aureus* (HIa) or a derivative or a fragment thereof. Detoxification can be achieved by chemical treatment, but preferably the detoxification is carried out by introducing a point mutation in the amino acid sequence of HIa. Preferably the detoxified HIa comprises a point mutation located at amino acid 35 (His) and/or at amino acid 48 (His), wherein the Histidine residue is replaced by a Leucine as described by Menzies and Kerodle (1996); Infect. Immun. 64; 1839 and Menzies and Kerodle (1994); Infect. Immun. 62(5); 1843-7 or by other amino acids such as Arginine, Lysine, Alanine or Glutamic acid. Optionally, such a detoxified HIa may also comprise a deletion in the amino latch domain as described in WO 2007/145689. In a further alternative, a derivative of the mature or premature form of HIa detoxified by deleting some or all the amino acids of the stem-like structure as described in U.S. Pat. No. 8,632,783 can be used. Deletion of all or part of the stem-like structure of HIa was shown to eliminate the haemolytic activity of the toxin. In a further embodiment, a fragment of the HIa comprising at least the first 50 amino acids of the Nterminal part of the amino acid sequence of HIa but unable to assemble into a heptameric ring structure can also be used as carrier protein. Active immunization with a fragment of the first 50 amino acids of the HIa toxin was also shown to confer protection against *S. aureus* mediated pneumonia [Ragle et al. (2009); Infect. Immun. 77(7), 2712].

Preparation and Features of the Conjugate

As shown in paragraph VI of the Examples section, the saccharide according to the invention, either synthetic or native (i.e. extracted and purified from natural source) has to be coupled to a carrier protein to induce an antibody response.

The conjugate according to the invention is made of a carrier protein and a saccharide comprising repetitive units of 1,5 ribitol phosphate in which all the ribitol residues are substituted by N-acetyl D-glucosaminyl residues at the 4-position, and wherein said N-acetyl D-glucosaminyl residues are exclusively in anomeric configuration α or are exclusively in anomeric configuration β. In particular, the saccharide comprises at least 4 identical repetitive units, wherein the repetitive unit has the following structure, (which may be in the form of a salt):

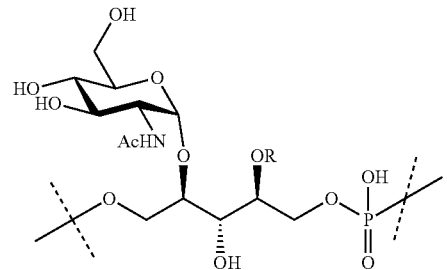

wherein R is independently H or D-Ala, and may be different from one repetitive unit to another, and
the N-acetyl D-glucosaminyl residue is in anomeric configuration α.

Preferably, the R groups of the repetitive units of the saccharide are all H.

In a preferred embodiment, the conjugate of the invention is made of a carrier protein and a saccharide comprising at least four identical repetitive units, wherein the repetitive unit has the following structure, which may be in the form of a salt:

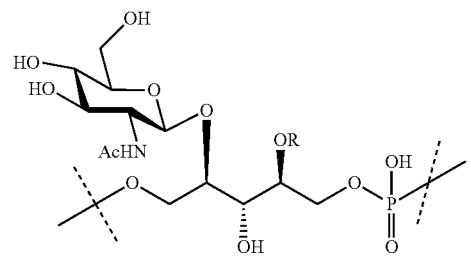

wherein R is independently H or D-Ala, and may be different from one repetitive unit to another, and
the N-acetyl D-glucosaminyl residue is in anomeric configuration β.

Preferably, the R groups of the repetitive units of the saccharide are all H.

Indeed, it has surprisingly been found that the structure of the repetitive units of the teichoic acids can evolve to some extent towards an "anomeric configuration β" when *S. aureus* stains are put in an "in vivo" environment as shown in paragraph I of the Examples section. This is evidenced by the fact that there is no change in the structure of the TA when a 100% β(1-4) strain is put in an "in vivo" environment, i.e. the glucosaminyl residues of the repetitive units remain in a β(1-4) anomeric configuration. In contrast, when a "mix α(1-4) and β(1-4) strain" is put in an "in vivo" environment (for instance by administration to an individual), this favours the production of 1,5 ribitol phosphate units having a β(1-4) anomeric configuration.

In a more preferred embodiment, the conjugate of the invention is made of a carrier protein and a saccharide consisting of identical repetitive units, wherein the number of repetitive units is preferably between 4 and 14, more preferably 6, 7, 8, 9, 10, 11, or 12, and the repetitive unit has the following structure, which may be in the form of a salt:

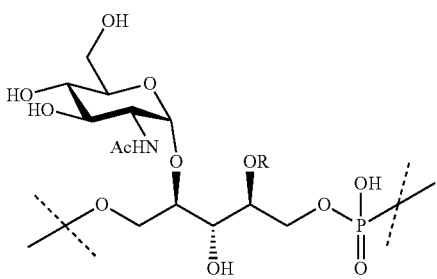

wherein R is H and the N-acetyl D-glucosaminyl residues are in anomeric configuration α.

In a still more preferred embodiment, the conjugate of the invention is made of a carrier protein and a saccharide consisting of identical repetitive units, wherein the number of repetitive units is preferably between 4 and 14, more preferably 6, 7, 8, 9, 10, 11, or 12, and the repetitive unit has the following structure, which may be in the form of a salt:

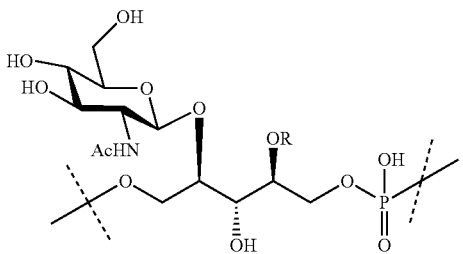

wherein R is an hydrogen atom and the N-acetyl D-glucosaminyl residues are in anomeric configuration β.

Figure 5:
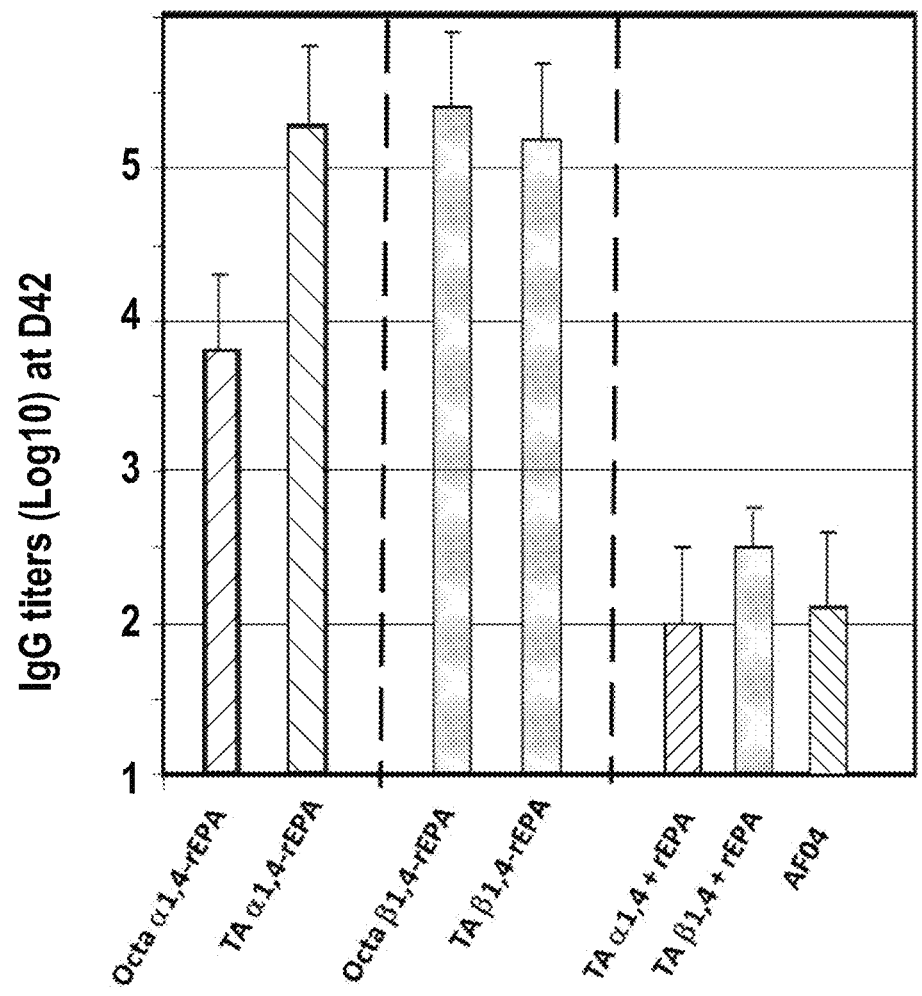
FIG. 5 represents the specific IgG titers directed against the homologous TA after 3 immunizations (D42) with unconjugated α(1,4) TA [TA α(1,4)+rEPA], unconjugated β(1,4) TA [TA β(1,4)+rEPA], synthetic α(1,4) octamer conjugate [Octa α(1,4)-rEPA], α(1,4) TA conjugate [TA α(1,4)-rEPA], synthetic β(1,4) octamer conjugate [Octa β(1,4)-rEPA], or with β(1,4) TA conjugate [TA β(1,4)-rEPA] in the presence of the AF04 adjuvant.
Figure 6:
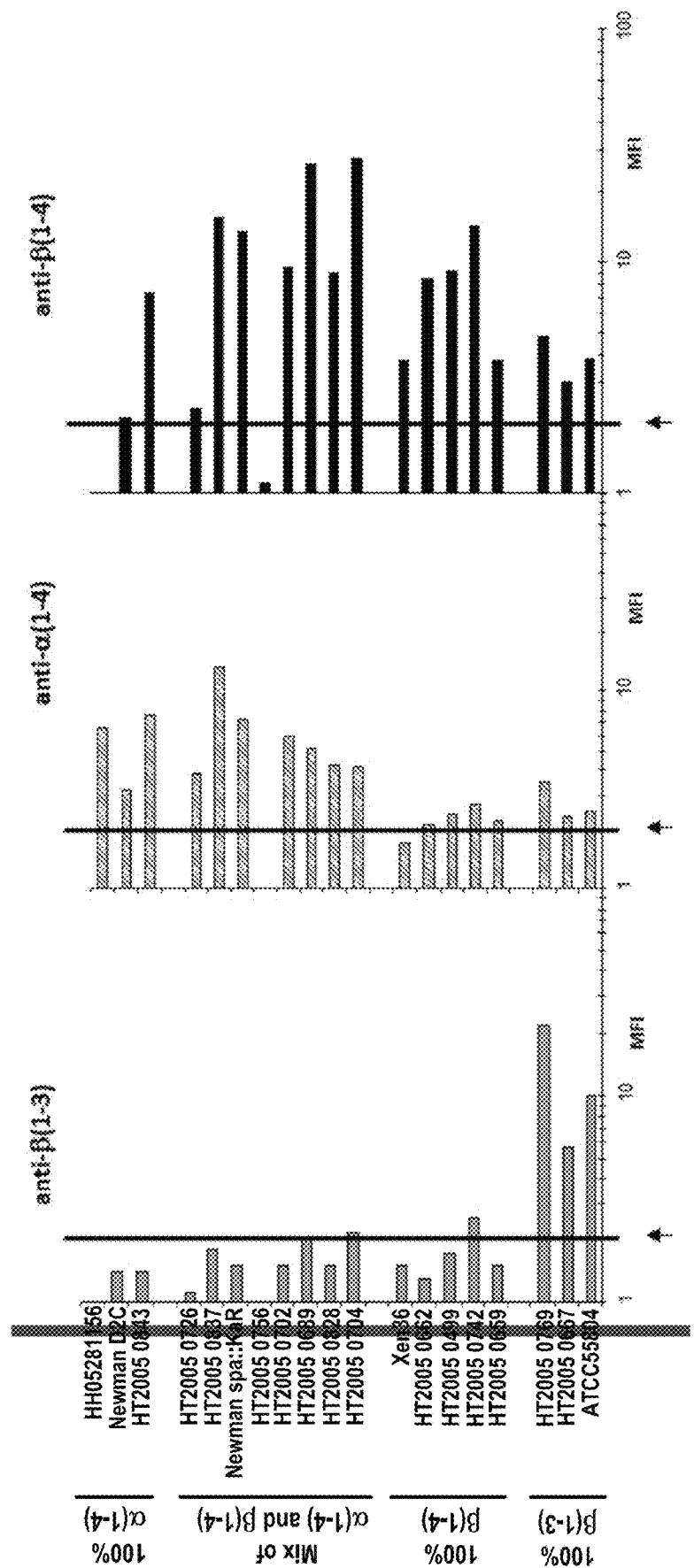
FIG. 6 is the recognition pattern of a panel of *S. aureus* strains by the immune sera of mice after immunization with either a synthetic α(1,4) octamer conjugate [anti α(1,4)], or a synthetic β(1,4) octamer conjugate [anti β(1,4)] or with a synthetic β(1,3) nonamer conjugate [anti β(1,3)].

As shown in FIGS. 5 and 6, it has surprisingly been found that a conjugate of a synthetic saccharide consisting of identical repeating units, whereby the N-acetyl D-glucosaminyl residues are exclusively in anomeric configuration β induces a stronger cross reactive antibody response than an analogous conjugate which has N-acetyl D-glucosaminyl residues exclusively in anomeric configuration α.

The conjugate according to the invention can be obtained by direct covalent linking of the saccharide to the carrier protein. The reactive groups of the saccharide such as the phosphate groups and/or the OH groups of the ribitol or of the N-acetyl glucosamine as well as the reactive groups present on the carrier protein such as carboxyl groups (for instance via aspartic acid or glutamic acid), amino groups (for instance via lysine), sulfhydryl groups (for instance via cysteine), hydroxyl groups (for instance via tyrosine), an imidazoyl group (for instance via histidine), a guanidyl group (for instance via arginine) and an indolyl group (for instance via tryptophan) can be used for coupling. For instance, when direct covalent linking is contemplated, the OH groups of the saccharide according to the invention can be activated using cyanogen bromide or 1-cyano-4-dimethylamino-pyridinium tetrafluoroborate (CDAP), 1,1'-carbonyldiimidazole (CDI) or 1,1'-carbonyldi-(1,2,4-triazole) (CDT). The carrier protein is then added and reacts via its amino groups with the activated polysaccharide.

Preferably, the linkage between the saccharide and the carrier protein is via the terminal phosphate group of the saccharide.

Preferably the saccharide is linked to the carrier protein via a linker to minimize the effects of steric hindrance which can decrease the level of antibody response against the saccharide and/or to avoid random coupling chemistry between the saccharide and the carrier protein. The chemical structure of the linker results from the use of one or several linking agents during the conjugation process. The linking agents are generally used: (i) to obtain a derivatized saccharide and/or a derivatized carrier protein; (ii) to introduce a new functional reactive group into the derivatized saccharide and/or the derivatized carrier protein; and/or (iii) to introduce a spacer between the saccharide and the protein.

When the coupling of the saccharide to the carrier protein involves the use of one linking agent, the method for preparing the conjugate according to the invention comprises:

1) providing the saccharide that comprises or consists of repetitive units of 1,5 ribitol phosphate in which all the ribitol residues are substituted by N-acetyl D-glucosaminyl residues at the 4-position, and wherein said N-acetyl D-glucosaminyl residues are exclusively in anomeric configuration α or exclusively in anomeric configuration β,
2) providing the carrier protein,
3) derivatizing said saccharide with a linking agent and coupling the derivatized saccharide with said carrier protein or alternatively, derivatizing said carrier protein with a linking agent and coupling the derivatized carrier protein with said saccharide to obtain the conjugate.

It is understood that steps 1 and 2, that may respectively include the preparation of the saccharide or the carrier, can be performed in any order, and that the overall steps have to be carried out such that they do not modify the chemical structure of the repeating units of the saccharide. Preferably, the saccharide comprises or consists of repetitive units of 1,5 ribitol phosphate in which all the ribitol residues are substituted by N-acetyl D-glucosaminyl residues at the 4-position, and wherein said N-acetyl D-glucosaminyl residues are exclusively in anomeric configuration β.

The linking agent (L1) which is used to obtain the derivatized saccharide is usually of the general formula, R'1-A-R'2 in which:

A denotes an aliphatic and/or aromatic chain which may be substituted or unsubstituted, saturated or unsaturated;
R'1 denotes an amine (in particular —$NH_2$) or a chemical group carrying a nitrogen, such as for instance, a group comprising a hydrazide such as —C(O)—NH—$NH_2$; and
R'2 denotes a group capable of reacting with a reactive group of the carrier protein, or alternatively a reactive group capable of reacting with a functional group present on a second linking agent (L2).

Advantageously, A denotes an alkyl, an alkylene (alkyl including at least one double bond) or a dithioalkyl (alkyl including a —S—S—), comprising from 1 to 12 carbons, advantageously from 2 to 8 carbons, preferably from 2 to 6 carbon atoms. Preferably, the linking agent of formula R'1-A-R'2 is an alkyl dihydrazide such as adipic acid dihydrazide; a monoamino thioalkyl such as cysteine or cysteamine, or a diamino dithioalkyl such as cystamine; or a diaminoakyl or diaminoalkylene, such as diaminomethane, diaminoethane or diaminohexane.

The saccharide can be activated with cyanogen bromide or 1-cyano-4-dimethylamino-pyridinium tetrafluoroborate (CDAP) to form cyanate esters that react with the R'1 group of the linking agent L1 to obtain the derivatized saccharide.

In another embodiment, the saccharide according to the invention is activated by treatment with a carbodiimide, for instance EDAC [1-ethyl-3-(3-dimethyl-aminopropyl) carbodiimide], in an aqueous medium under mild acidic conditions in presence of the linking agent L1. During this step the molar ratio of the linking agent to the saccharide is higher than 1, preferably higher than 5.

The derivatized saccharide obtained is then covalently linked to the carrier protein via the R'2 group of the linking agent. Usually, the weight/weight ratio of the saccharide to the carrier protein is between 0.1 and 10, preferably between 0.25 and 8, more preferably between 0.25 and 6, and still more preferably between 0.25 and 4.

In a particular embodiment of the invention, the method for preparing a conjugate according to the invention comprises:
1) extracting and purifying a saccharide according to the invention from the WTA of a "100% α(1-4) strain", such as Newman D2C strain (ATCC 25904), or a "100% β(1-4) strain", such as Wood 46 strain (ATCC 10832);
2) derivatizing the purified polysaccharide by carbodiimide treatment, for instance EDAC, in the presence of adipic acid dihydrazide as linking agent; and
3) coupling the derivatized saccharide to a detoxified form of the exoprotein A of *Pseudomonas aeruginosa*, for instance rEPA, in presence of a carbodiimide, for instance EDAC, to obtain the conjugate.

Advantageously, the conjugation process involves two linking agents to target still more specifically the coupling chemistry between the saccharide and the carrier protein, to hamper random coupling chemistry between the saccharide and the carrier protein and/or to increase the distance between the saccharide and the carrier protein (i.e. the size of the linker). Two linking agents are used to derivatize separately the saccharide according to the invention and the carrier protein. Accordingly, a method for preparing a conjugate according to the invention comprises:
1) providing the saccharide that comprises or consists of repetitive units of 1,5 ribitol phosphate in which all the ribitol residues are substituted by N-acetyl D-glucosaminyl residues at the 4-position, and wherein said N-acetyl D-glucosaminyl residues are exclusively in anomeric configuration α or are exclusively in anomeric configuration β,
2) providing the carrier protein,
3) derivatizing said saccharide with a first linking agent,
4) derivatizing said carrier protein with a second linking agent, and
5) coupling said derivatized saccharide with said derivatized carrier protein to obtain the conjugate.

It is understood that: (i) steps 1 and 2, that may respectively include the preparation of the saccharide or the carder, can be performed in any order; (ii) steps 3 and 4 can be performed in any order and (iii) that steps 1 to 5 have to be carried out such that they do not modify the chemical structure of the repeating units of the saccharide.

Considering that the first linking agent (L1) is used for derivatizing the saccharide, the choice of the second linking agent (L2) is conditioned by the functional reactive group R'2 carried by the first linking agent (L1) and the functional reactive group which is targeted on the carrier protein The L2 linking agent is usually a chemical compound of formula R3-B—R4, in which: B denotes an aliphatic and/or aromatic chain which may be substituted or unsubstituted, saturated or unsaturated;

R3 denotes a functional reactive group capable of reacting with the functional group R'2 carried by L1; and
R4 denotes a functional reactive group capable of reacting with a functional group of the carrier protein.

Advantageously, B denotes an alkyl or an alkylene which may be substituted or unsubstituted, comprising from 1 to 12 carbons, preferably from 2 to 8 carbon atoms; an aryl, an alkylaryl or an arylalkylene, comprising from 7 to 12 carbon atoms; a phenyl or phenylene which may be substituted or unsubstituted.

When R'2 comprises a thiol group, R3 can be a thiol group; an unsaturated α- or β-carbonyl or an imidyl group, in particular a maleimidyl group; an acyl halide or an alkyl halide, in which the halogen is a bromine, a chlorine or an iodine.

Advantageously, R4 is capable of reacting with a carboxyl, thiol or amine group of the carrier protein. Thus, if the functional group of the carrier protein which is targeted in the conjugation process is a thiol, R4 can be a maleimide group. Similarly, if the functional group of the carrier protein which is targeted in the conjugation process is an amine, R4 can be a carboxyl group or preferably an N-hydroxysuccinimidyl or N-hydroxysulfosuccinimidyl group.

When the L1 linking agent is a diaminoalkyl or a dihydrazide, the second inking agent L2 is advantageously chosen from the disuccinimidylalkyl or succinimidylmaleimidoalkyl compounds of formula R3-B—R4 in which B is an alkyl group, R3 is a succinimidyl group and R4 is a succinimidyl or maleimido group. The disuccinimidyl group can be disuccinimidyl suberate (DSS), bis(sulfosuccinimidyl) suberate (BS3), disuccinimidyl glutarate (DSG), the succinimidyl diester of adipic acid (SIDEA) or the succinimidyl diester of succinic acid. The succinimidyl and or sulfosuccinimidyl groups are capable of reacting with an amine group. The succinimidylmaleimidoalkyl compound can be one of those mentioned above.

In a preferred embodiment, the L1 linking agent is an aminothiol such as cysteine, cysteamine or cystamine, and the second linking agent L2 is advantageously a succinimidyl maleimidyl alkyl. The latter is preferably selected among: γ-maleimidobutyric acid N-hydroxysuccinimide ester (GMBS), succinimidyl-3 (bromoacetamido) propionate (SBAP), γ-maleimidobutyric acid N-sulfosuccinimide ester (sulfo-GMBS), ε-maleimidocaproic acid N-hydroxysuccinimide ester (MCS), succinimidyl 4-(p-maleimidophenyl) butyrate (SMPB), sulfosuccinimidyl 4-(p-maleimidophenyl) butyrate (sulfo-SMPB), maleimidobenzoic acid N-hydroxysuccinimide ester (MBS), maleimidobenzoic acid N-hydroxysulfosuccinimide ester (sulfo-MBS), 4-(N-maleimidomethyl)cyclohexanecarboxylic acid N-hydroxysuccinimide ester (SMCC) and 4-(N-maleimidomethyl)cyclohexanecarboxylic acid N-hydroxysulfosuccinimide ester (sulfo-SMCC).

In another preferred embodiment of the invention, the method for preparing a conjugate according to the invention comprises:
1) extracting and purifying a polysaccharide according to the invention from the WTA of a "100% α(1-4) *S. aureus* strain" such as Newman D2C strain (ATCC 25904) or a "100% β(1-4) *S. aureus* strain" such as Wood 46 strain (ATCC 10832);
2) derivatizing the purified polysaccharide by carbodiimide treatment, such as EDAC in presence of cystamine;
3) cleaving the disulfide bond of the derivatized polysaccharide with a reducing agent, such as dithiothreitol;

4) derivatizing a carrier protein by treatment with ymaleimidobutyric acid N-hydroxysuccinimide ester (GMBS), or with Succinimidyl-3 (bromoacetamido) propionate (SBAP); and
5) coupling the cleaved and derivatized polysaccharide with the derivatized carrier protein to obtain the conjugate.

The main chemistry steps are summarized in the schema below in which TA-OP(O)O⁻OH designates the saccharide and Prot the carrier protein:

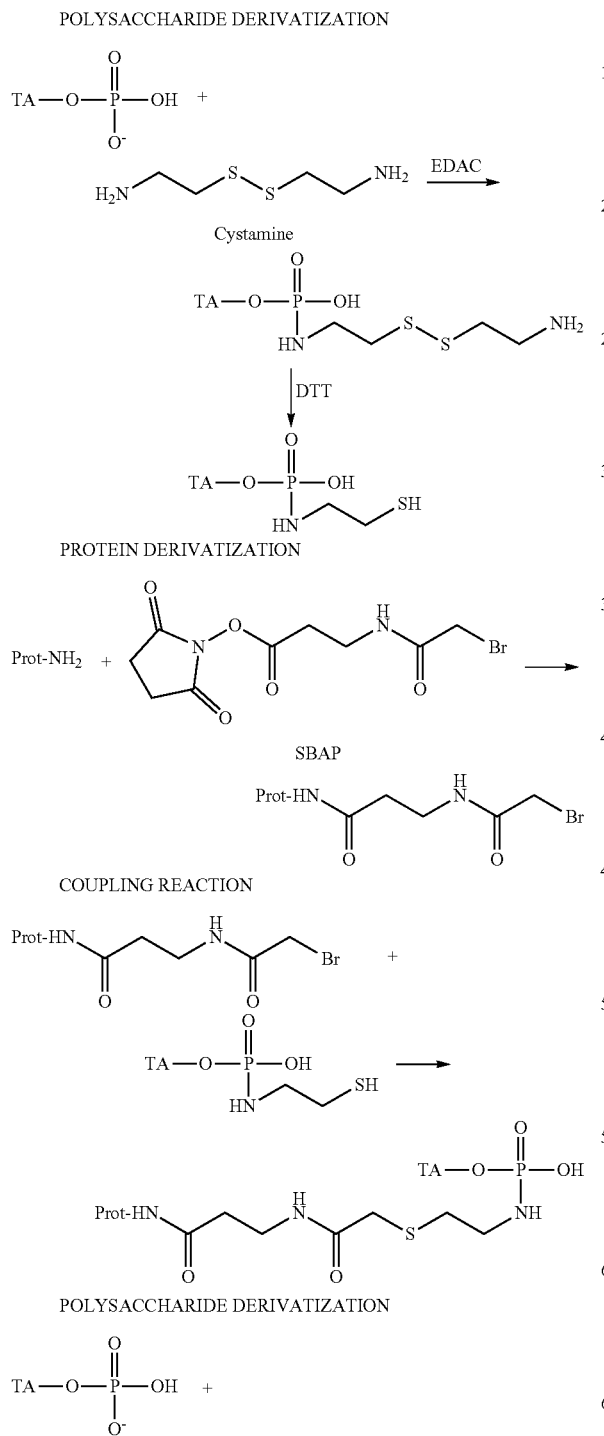

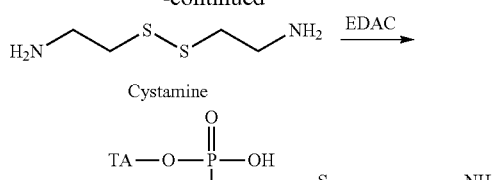

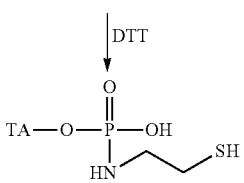

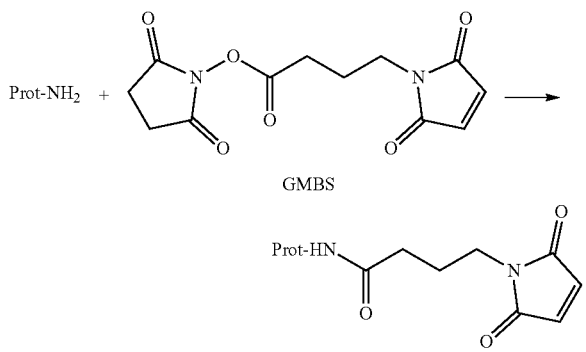

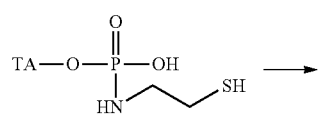

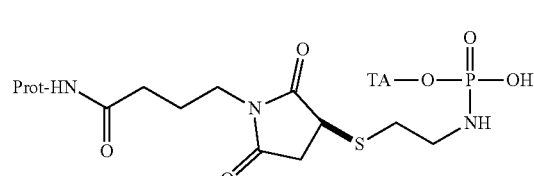

Preferably, the carrier protein is a detoxified α-hemolysin of *S. aureus* (HIa), a derivative or a fragment thereof.

To prevent multiple anchorages of the carrier protein on the saccharide, which may potentially mask one or several useful epitopes carried by the conjugate and be detrimental to the features of the immune response induced by the conjugate, the invention relates to a conjugate, wherein the carrier protein is linked via a linker to the terminal phosphate of the saccharide as defined in the invention. More specifically, the conjugate has the following structure:

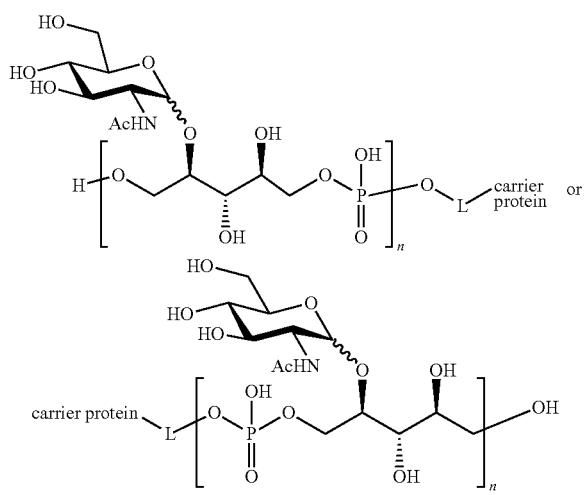

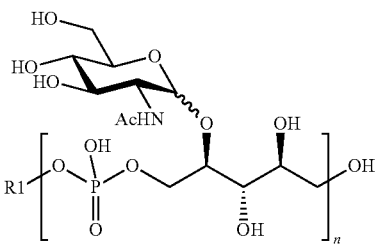

wherein the N-acetyl D-glucosaminyl residues are exclusively in anomeric configuration α or exclusively in anomeric configuration β;

n is at least 4, preferably 6, 7, 8, 9, 10, 11, or 12; and

R1 is H, an alkyl amine or an alkyl hydrazide, preferably an alkyl amine or an alkyihydrazide;

wherein:
the N-acetyl D-glucosaminyl residues are exclusively in anomeric configuration α or exclusively in anomeric configuration β;
n is ≥4, preferably between 6 and 12, preferably 6, 7, 8, 9, 10, 11 or 12; and
L is the linker;
or a pharmaceutically acceptable salt thereof.

Preferably, said N-acetyl D-glucosaminyl residues are exclusively in anomeric configuration β.

Accordingly, the method for preparing such a conjugate comprises:
1) preparing a synthetic saccharide or a salt thereof having the following chemical structure:

2) preparing a carrier protein;

3) optionally derivatizing said saccharide with a first linking agent, 4) optionally derivatizing said carrier protein with a second linking agent; and 5) coupling said saccharide or said derivatized saccharide with said protein or said derivatized protein derivatized saccharide to obtain the conjugate.

It is understood that: (i) steps 1 and 2 can be performed in any order; (ii) steps 3 and 4 can be performed in any order and (iii) that steps 1 to 5 have to be carried out such that they do not modify the chemical structure of the repeating units of the saccharide. Preferably, the N-acetyl D-glucosaminyl residues are exclusively in anomeric configuration β.

In a particular aspect, the conjugate has the following structure:

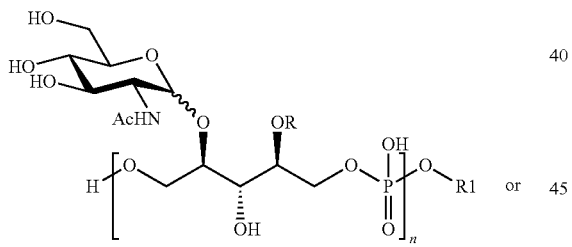

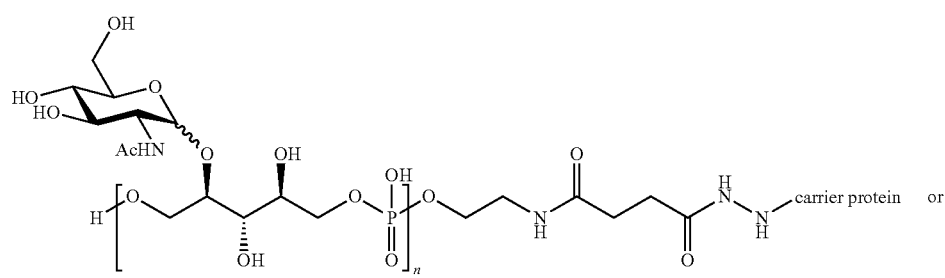

-continued

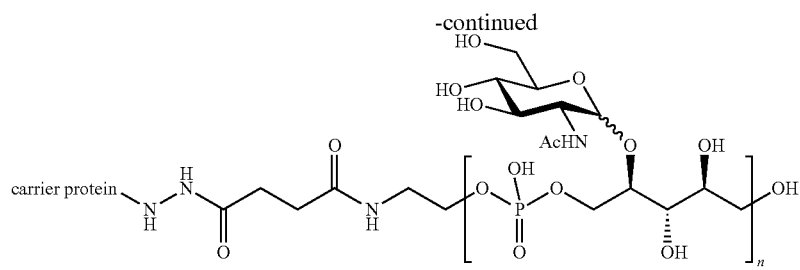

wherein the N-acetyl D-glucosaminyl residues are exclusively in anomeric configuration α or exclusively in anomeric configuration β;

n is at least 4; n being preferably between 4 and 14, more preferably n being 6, 7, 8, 9, 10, 11, or 12;

and the carrier protein is preferably a detoxified bacterial toxin, such as rEPA, a detoxified α-hemolysin of *S. aureus* (HIa), or a derivative or a fragment thereof;

or a pharmaceutically acceptable salt of said conjugate. Preferably, the N-acetyl D-glucosaminyl residues are exclusively in anomeric configuration β.

Accordingly, the method for preparing such a conjugate comprises:

1) preparing a synthetic saccharide or a salt thereof having the following chemical structure:

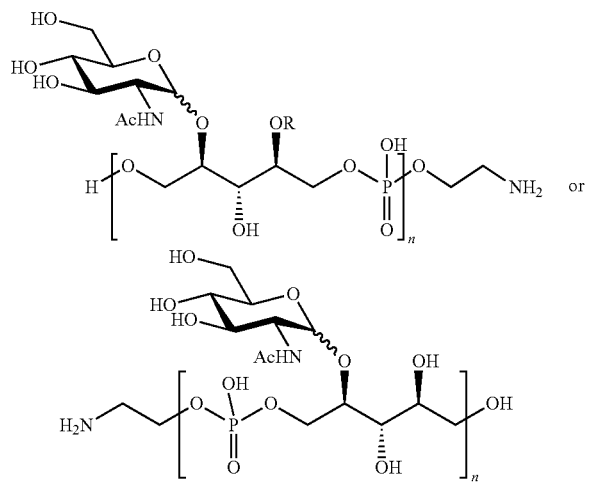

wherein the N-acetyl D-glucosaminyl residues are exclusively in anomeric configuration α or exclusively in anomeric configuration β; and n is at least 4; preferably 6, 7, 8, 9, 10, 11, or 12, 2) preparing a carrier protein, such as rEPA or HIa,
3) derivatizing said saccharide using disuccinimidyl succinate as a linking agent, followed by hydrazine treatment, and
4) coupling said derivatized saccharide with the carrier protein to obtain the conjugate.

Preferably, said N-acetyl D-glucosaminyl residues are exclusively in anomeric configuration β. Preferably, the carrier protein is a detoxified α-hemolysin of *S. aureus* (HIa) or a derivative or a fragment thereof. Preferably, the N-acetyl D-glucosaminyl residues are exclusively in anomeric configuration β.

As shown in the table of paragraph VI in the Examples section, it has been found that a synthetic conjugate, especially when the N-acetyl D-glucosaminyl residues are exclusively in anomeric configuration β, whereby the saccharide is only linked by its terminal phosphate to the carrier protein via a linker induces a more powerful cross reactive antibody response than the corresponding hemisynthetic conjugate prepared from a natural saccharide. Without being bound by theory, it is likely that the unique anchorage of the carrier protein to the saccharide at the terminal phosphate and the lack of any additional antigenic structure in the synthetic saccharide other than the repetitive units as defined in the invention, are useful means to optimize the quality of the cross reactive antibody response.

At the end of the conjugation process, regardless of the method used, the conjugates obtained are usually purified to remove the residual, unconjugated saccharide and protein fractions, for instance by ammonium sulfate precipitation, by ultrafiltration, by hydrophobic chromatography, or by size exclusion chromatography. When size exclusion chromatography is used, depending on the size of the saccharide of the invention, a column of Sepharose 6B or Superdex 75 can be used.

Formulation of the Conjugate

The conjugate of the invention can be formulated in a composition with any pharmaceutically acceptable vehicle. In the context of the invention, the expression "pharmaceutically acceptable vehicle" refers to a vehicle that is physiologically acceptable for administration to a mammal, and in particular to a human being, while retaining the physiological activity of the conjugate according to the invention, i.e. its ability to induce an immune response. One exemplary pharmaceutically acceptable vehicle is physiological saline. Other physiologically acceptable vehicles are known to those skilled in the art and are described, for instance, in Remington's Pharmaceutical Sciences (18th edition), ed. A. Gennaro, 1990, Mack Publishing Company, Easton, Pa.

The pH of the composition is usually between 6 and 8, and more preferably between 6.5 and 7.5 (e.g. about 7). Stable pH may be maintained by the use of a buffer e.g. a Tris buffer, a citrate buffer, phosphate buffer, or a histidine buffer. Thus the composition will generally include a buffer. The composition may be sterile and/or pyrogen-free. Compositions may be isotonic with respect to humans.

A composition according to the invention will comprise an immunologically effective amount of the conjugate. An 'immunologically effective amount' is an amount which, when administered to a subject, is effective for eliciting an antibody response against the conjugate. This amount can vary depending upon the health and physical condition of the subject to be treated, their age, the capacity of the subject's immune system to produce antibodies, the degree of protection desired, the formulation of the vaccine, the treating doctor's assessment of the medical situation. The 'immunogenically effective amount' of a particular conjugate in a composition is generally dosed based on total polysaccharide, conjugated and non-conjugated for that conjugate. In general, a dose of a composition according to the present invention will contain from 0.1 to 100 μg of the polysaccharide.

In a preferred embodiment of the invention the conjugate of the invention is formulated in a composition with an adjuvant to enhance the antibody response. Examples of suitable adjuvants include those that are mainly acting as delivery systems, such as aluminium salts, calcium phosphate, liposomes, virosomes, ISCOMs, micro- and nanoparticles, emulsions and/or those that are mainly acting as immunopotentiators, such as TLR agonists. A TLR agonist is understood to mean a natural TLR ligand, a TLR ligand mimic, a synthetic or chemical TLR ligand, a cell or particle including a pathogen associated molecular pattern, a microbial pathogen, a bacterium, a virus and viral-like particle. In a preferred embodiment of the invention, the adjuvant comprises a TLR4 agonist. Examples of TLR4 agonists include monophosphoryl lipid A or a derivative thereof, particularly 3-de-O-acylated monophosphoryl lipid A (3D-MPL), Phosphorylated hexaacyl disaccharide also called GLA (CAS Number 1246298-63-4), aminakyl glucosaminide phosphates (AGPs) as described in WO 98/50399 or in WO 01/034617, in particular RC529 described in U.S. Pat. No. 6,113,918, and chemical compounds as described in US 2003/0153532 or in US 2005/0164988, in particular the compounds identified and exemplified in US 2003/0153532 under the following names: ER803022 (CAS number: 287180-56-7), ER803058 (CAS number: 287180-57-8), ER803732 (CAS number: 287106-29-0), ER803789 (CAS number: 287180-61-4), ER804053 (CAS number: 287180-62-5), ER804057 (CAS number: 287180-63-6), ER804058 (CAS number: 287180-65-8), ER804059 (CAS number: 287180-64-7), ER 8044442 (CAS number: 287180-78-3), ER 804764 (CAS number: 287180-87-4), ER111232 (CAS number: 287180-48-7), ER112022 (CAS number: 287180-46-5), ER112048 (CAS number: 287106-02-9), ER112065 (CAS number: 287180-49-8), ER112066 (CAS number: 287180-50-1), ER113651 (CAS number: 287180-51-2), ER118989 (CAS number: 287180-52-3), ER119327 (CAS number: 287180-54-5) and ER119328 (CAS number: 287180-55-6). These compounds have generally one or several asymetric carbons. When these compounds have one or several asymmetric carbons, they can be used as a mixture of optical isomers or under the form of a specific isomer. These TLR4 agonists can also be themselves combined with a delivery system such as aluminium salt (for instance aluminium phosphate and/or aluminium hydroxide), calcium phosphate, liposomes, virosomes, ISCOMs, micro- and nanoparticles, emulsions. As an example of suitable formulation of a TLR4 agonist combined with a delivery system, citation is made of an oil in water emulsion comprising as TLR4 agonist the compound ER 804057 (now called E6020) (CAS number: 287180-63-6), which is the disodium salt of the compound having the following chemical formula:

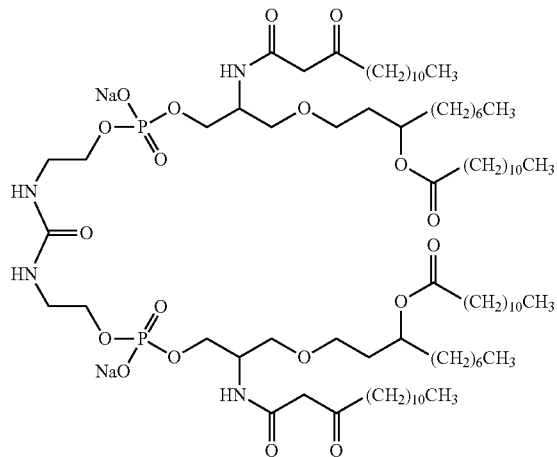

The four asymmetric carbons of E6020 are all in in the Rconfiguration (R,R,R,R). Such an emulsion can be obtained for instance by microfluidisation techniques as described in WO 2004/060396 or by a phase inversion temperature process (PIT process) as described in WO 2007/080308.

Another suitable combination of a TLR4 agonist and a delivery system may be a mixture of a TLR4 agonist with an aluminium salt, in particular a mixture of E6020 adsorbed on aluminium hydroxide in a phosphate buffer.

More specifically the adjuvants can also be classified according to the type of immune response they induce in the presence of the antigen. A Th1-type immune response is associated with an increased production of IFN-r and/or IL-2 cytokines by T-lymphocytes while a Th-2 type immune response is associated with an increased production of IL-4, IL-5, IL-13, and/or IL-10 cytokines. A Th17-type immune response is associated with an increase in the IL-17 response. An adjuvant that induces predominantly a Th1-type immune response is considered as a Th1 adjuvant. Likewise, an adjuvant that induces predominantly a Th2-type immune response is considered as a Th2 adjuvant, as well as an adjuvant that induces predominantly a Th17-type immune response is a Th17 adjuvant. In the context of the invention, the adjuvant is preferably a Th1 adjuvant, a Th17 adjuvant or a Th1/Th17 adjuvant (which induces predominantly both a Th1-type immune response and Th17-type immune response).

The adjuvant or the combination of adjuvants and the conjugate according to the invention are usually mixed together if there is no incompatibility between the products or alternatively the adjuvant can be extemporaneously added to the conjugate just prior to administration to an individual.

Use of the Conjugates

The subject matter of the invention also relates to a method of inducing a cross reactive antibody response in an individual at risk of *S. aureus* infection, said method comprising the administration of an immunogenic composition to said individual that comprises a conjugate according to the invention. This immunogenic composition can be formulated as described above in section "Formulation of the conjugate".

The method may be applied to any animal at risk of *S. aureus* infection, i.e. any animal sensitive to *S. aureus* infection whatever the outcome of the infection: asymptomatic and/or symptomatic, lethal or non-lethal, chronic or not. In particular, the method applies to a human being or an animal selected from a canine, a feline, a bovine, a porcine, an equine or an ovine species as well as the mustelids and the avian species since they are susceptible to *S. aureus* infections. In a particular embodiment, the method applies to individuals at greater risk of contracting *S. aureus* infection. In humans, it applies to immune-compromised individuals or individuals that are hospitalized or will be hospitalized because of the risk of *S. aureus*-associated nosocomial infections. Accordingly, the method according to the invention applies to individuals that will undergo a surgical procedure, in particular those whose surgery leads to the implantation of a medical device such as a urinary sonde, an orthopedic prosthesis, a pacemaker, a cardiac valve, etc.

The composition comprising the conjugate according to the invention can be administered via any route commonly used and following a regimen leading to the induction of an immune response. Usually, the immunization schedule includes several administrations. The amount of the composition administered is enough to produce the desired immune response, i.e. a cross reactive antibody response. Preferably the immunogenic composition of the conjugate according to the invention also comprises an adjuvant, such as a TLR4 agonist (for instance E6020) which may be combined with a delivery system as described above.

Advantageously, the method according to the invention induces the production of cross reactive antibodies that recognize a broad panel of *S. aureus* strains, in particular *S. aureus* strains identified as "100% β(1-3) strains", such as the *S. aureus* type 336 strain (ATCC number 55804), in which all the ribitol groups of the repetitive units of the TA are substituted by β(1-3) N-acetyl D-glucosaminyl residues, *S. aureus* strains identified as "100% β(1-4) strains", such as the Wood 46 strain (ATCC number 10832) in which all the ribitol groups of the repetitive units of the TA are substituted by β(1-4) N-acetyl D-glucosaminyl residues and *S. aureus* strains identified as "100% α(1-4) strains", such as the Newman D2C strain (ATCC number 25904) in which all the ribitol groups of the repetitive units of the TA are substituted by α(1-4) N-acetyl D-glucosaminyl residues.

In another aspect, the immunogenic composition comprising the conjugate of the invention can be administered to an individual who then acts as a source of "hyper immune globulin" that contains antibodies directed against a broad panel of *S. aureus* strains. An individual thus treated would be a plasma donor from which "hyper immune globulin" would then be obtained via conventional plasma-fraction methodology, and administered to another subject in order to impart resistance to *S. aureus* infection. Hyper immune globulins obtained with a conjugate according to the invention are particularly useful for immune-compromised individuals unable to mount an antibody response following the administration of the immunogen according to the invention or individuals undergoing surgery where time does not permit the individual to produce his own antibodies before the surgery.

The present invention is further described by reference to the following illustrative examples.

EXAMPLES

List of Abbreviations Used in the Examples and Meanings

Abbreviations

Ac: acetyl
AcOEt: ethyl acetate
ADH: adipic dihydrazide
Bn: benzyl
CAN: ceric ammonium nitrate
CE: capillary electrophoresis
CFU: colony forming unitsDCM: dichloromethane
DMAP: 4-dimethylaminopyridine
DMF: N,N-dimethytformamide
DMSO: dimethyl sulfoxide
EDCl: 1-(3-dimethylaminopropyl)-3-ethylcarbodiimide hydrochloride
Et: ethyl
EDAC: ethyldiaminopropylcarbodiimide
ESI: electron Spray Ionisation
ESI-MS: mass spectrometry coupled ESI
ETT: 5-(ethytthio) tetrazole
h: hour
HIa: *S. aureus* alpha-hemolysin, also known as alpha-toxin
HIadM: detoxified double mutant *S. aureus* alpha toxin (HIadM) as carrier protein. HIadM comprises the detoxifying mutations H35L and H48L
HPAEC-PAD: High performance anion exchange chromatography coupled to pulse amperometric detection.
HPSEC: High Performance Size Exclusion Chromatography
IF buffer: immunofluorescence buffer
Lev: levulinoyl
LC-MS: mass spectrometry coupled liquid chromatography
Me: methyl
MEKC: micellar capillary electrophoresis
MES: 2-(N-morpholino) ethanesulfonic acid
MeOH: methanol
MIBK: methyl isobutyl ketone
min: minute (s)
mL: millilitre (s)
mm: millimetre (s)
mM: millimolar
mmol: millimole(s)
MP: para-methoxyphenyl
MW: molecular weight
NMR: nuclear magnetic resonance
PBS: phosphate buffered saline
Ph: phenyl
Py: pyridine
rEPA: non-toxic *Pseudomonas aeruginosa* recombinant exotoxin A
Rib: ribitol phosphate
Rf: retention factor
rt: room temperature
RT: retention time
SFC: supercritical fluid chromatography
SFC-MS: mass spectrometry coupled SFC
TA: teichoic acid
TBAF: tetra-butylammonium fluoride
TBDMS: tert-butyldimethylsilyl
TBDPS: tert-butyldiphenysilyl
TFA: trifluoroacetic acid
THF: tetrahydrofurane
TLC: thin layer chromatography
TNBS: 2,4,6-Trinitrobenzenesulfonic acid
TSB: tryptic soy broth
Z: benzyloxy-carbonyl I) Characterization of the Teichoic Acids from a Panel of *S. aureus* Strains The nature of the GlcNAc glycosidic linkage to the ribitol phosphate units of the TAs from a representative panel of 20 *S. aureus* strains comprising, for example, *S. aureus* strains obtained from cell collections and *S. aureus* strains from clinical isolates kindly provided by the Centre National de référence des Staphylocoques, Hôpital Edouard Herriot, Lyon, France was determined for each strain by carbotyping using High Performance Anion Exchange Chromatography coupled to Pulsed Amperometry Detection (HPAEC-PAD) after acid treatment of the bacteria with hydrogen fluoride (HF). GlcNAc-Rib disaccharides were released by HF hydrolysis from the polyribitol phosphate backbone of TA.

Cell Growth

Figure 2:
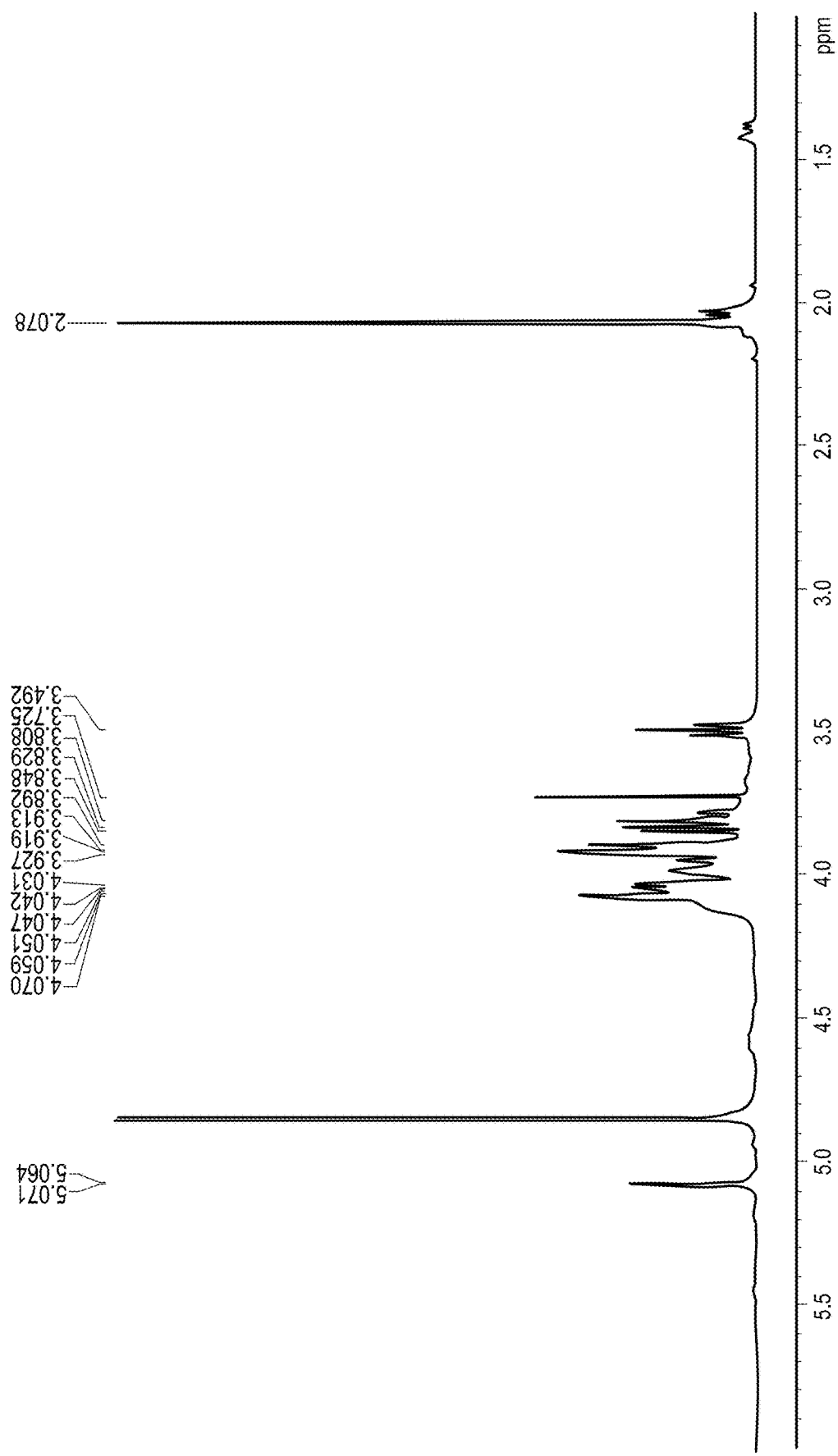
FIG. 2 is the 500 MHz $^1$H NMR spectrum of the purified α(1,4) TA from strain Newman D2C in $D_2O$ at 293K.
Figure 3:
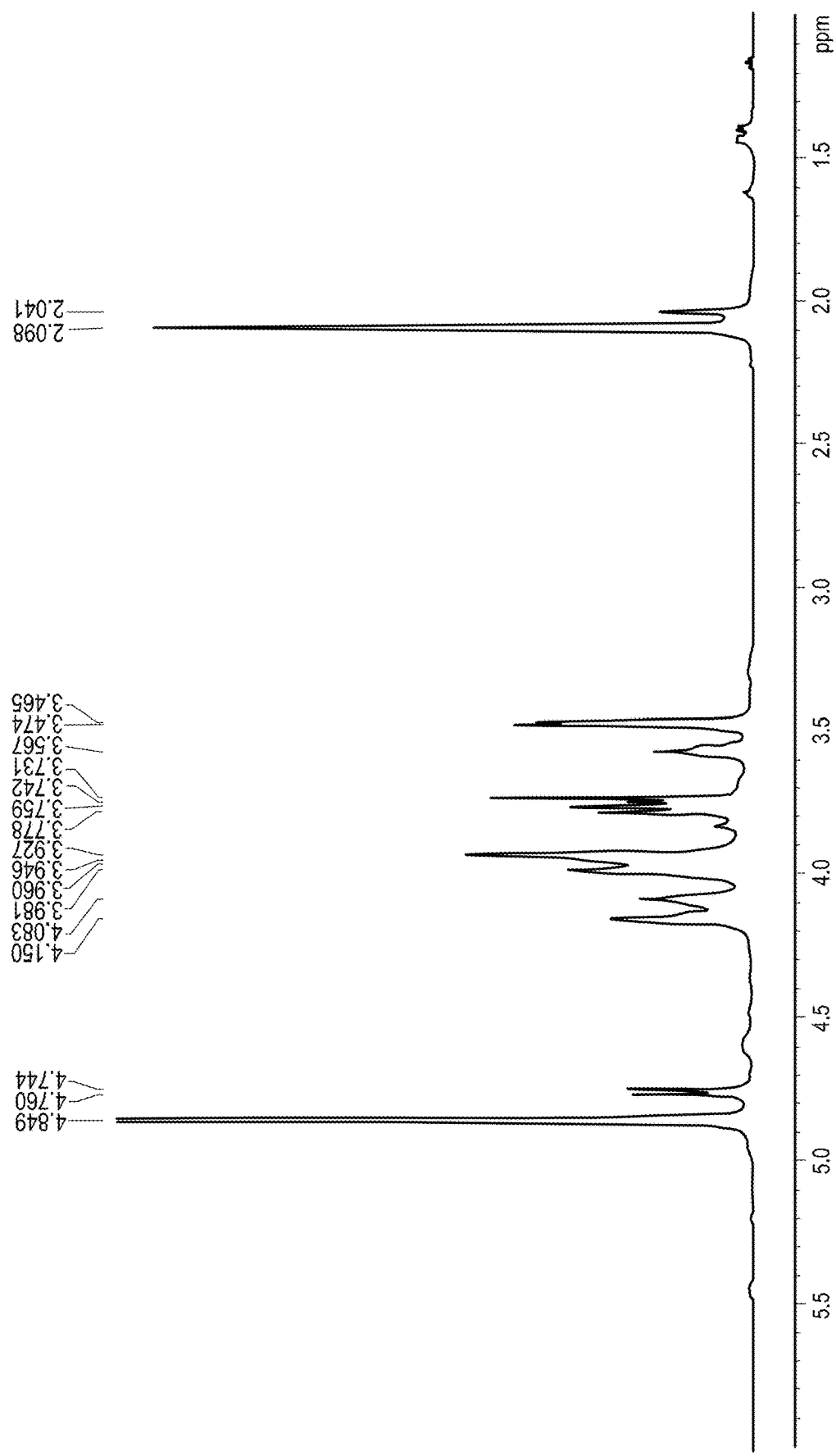
FIG. 3 is the 500 MHz $^1$H NMR spectrum of the purified β(1,4) TA from strain Wood 46 in $D_2O$ at 293K.

*S. aureus* strains were grown on Tryptic Soy Broth medium (TSB) overnight. For each strain a volume of broth culture containing $10^9$ CFU was centrifuged at 5,000 g and +4° C. for 20 min. The cell paste was then washed with 0.5 mL of 0.15M NaCl and centrifuged again. The supernatant was discarded. The cell pellet was suspended in 200 µL of 48% HF and incubated at room temperature overnight. Acid was removed under a stream of nitrogen at 40° C. and dried cell hydrolysate was suspended in 400 µL of water. After removing cell debris by centrifugation, 300 µL of sample was passed through a centrifugal filter unit (10 kDa MW cut-off, Ultracel-10, Millipore) to remove proteins and other macromolecules. The GlcNAc-Rib disaccharides were separated on a Dionex system using a CarboPac MA1 (4 mm×250 mm) analytical column with a guard column (4 mm×50 mm) previously equilibrated in 480 mM NaOH at a flow rate of 0.4 mL/min. The disaccharides were separated isocratically using 480 mM NaOH for 40 min. The Purified TAs as described in paragraph IV, the structures of which have been determined by Nuclear Magnetic Resonance Spectroscopy as shown in FIGS. 1 to 3, were hydrolyzed in the same way and used as standards to determine the exact nature of the GlcNAc glycosidic linkage of the 20 isolated GlcNAc-Rib disaccharides.

The ratio between the peak area corresponding to the GlcNAc-Rib disaccharide wherein the N-acetyl D-glucosaminyl residue was in the anomeric configuration α and the peak area corresponding to the GlcNAc-Rib disaccharide wherein the N-acetyl D-glucosaminyl residue was in the anomeric configuration β was directly related to the proportion of the N-acetyl D-glucosaminyl residues that were in the anomeric configuration α and in the anomeric configuration β in the ribitol phosphate units of the TA from the strain analyzed. When there was only one peak corresponding to the GlcNAc-Rib disaccharide in which the N-acetyl D-glucosaminyl residue was in the anomeric configuration α, the strain was a 100% α 1-4 strain. Likewise, when there was only one peak corresponding to the GlcNAc-Rib disaccharide wherein the N-acetyl D-glucosaminyl residue was in the anomeric configuration β, the strain was a 100% β 1-4 strain or a 100% β 1-3 strain according to the position of the peak in the chromatogram and by reference to the chromatograms of the standards.

Carbotyping results of the 20 strains tested are summarized in the table below.

| Identification of the strain | origin | category | Phenotype of the capsule | Biochemical characterization of the ribitol phosphate units | | |
|---|---|---|---|---|---|---|
| | | | | βGlcNAc (1-3) | βGlcNAc (1-4) | αGlcNAc (1-4) |
| HT2005 0769 | Clin. Isol. | 100% β(1-3) | PS5 | 100% | | |
| HT2005 0667 | Clin. Isol. | 100% β(1-3) | PS5 | 100% | | |
| ATCC 55804 | Cell collection | 100% β(1-3) | Neg. | 100% | | |
| Xen36 | Cell. collection | 100% β(1-4) | PS8 | | 100% | |
| HT2005 0662 | Clin. Isol. | 100% β(1-4) | PS5 | | 100% | |
| HT2005 0499 | Clin. Isol | 100% β(1-4) | PS5 | | 100% | |
| HT2005 0742 | Clin. Isol | 100% β(1-4) | PS5 | | 100% | |
| HT2005 0659 | Clin. Isol | 100% β(1-4) | PS5 | | 100% | |
| HH0528 1156 | Clin. Isol | 100% α(1-4) | Neg | | | 100% |
| Newman D2C ATCC25904 | Cell collection | 100% α(1-4) | PS5 | | | 100% |
| HT2005 0843 | Clin. Isol | 100% α(1-4) | PS5 | | | 100% |
| Newman Foster NCTC8178 | Cell collection | Mix α(1-4) and β(1-4 | PS5 | | 10% | 90% |
| HT2005 0726 | Clin. Isol | Mix α(1-4) and β(1-4) | PS8 | | 20% | 80% |
| HT2005 0837 | Clin. Isol | Mix α(1-4) and β(1-4) | Neg. | | 20% | 80% |
| Newman spa::KaR | Cell Collection | Mix α(1-4) and β(1-4) | PS5 | | 30% | 70% |
| HT2005 0756 | Clin. Isol | Mix α(1-4) and β(1-4) | PS5 | | 30% | 70% |
| HT2005 0702 | Clin. Isol | Mix α(1-4) and β(1-4) | PS8 | | 60% | 40% |
| HT2005 0689 | Clin. Isol | Mix α(1-4) and β(1-4) | PS5 | | 60% | 40% |
| HT2005 0828 | Clin. Isol | Mix α(1-4) and β(1-4) | Neg. | | 90% | 10% |

|  |  |  | Phenotype | Biochemical characterization of the ribitol phosphate units | | |
|---|---|---|---|---|---|---|
| Identification of the strain | origin | category | of the capsule | βGlcNAc (1-3) | βGlcNAc (1-4) | αGlcNAc (1-4) |
| HT2005 0704 | Clin. Isol | Mix α(1-4) and β(1-4) | PS8 |  | 90% | 10% |

These results clearly show structural variations in the ribitol phosphate repeating units of S. aureus TA. Three strains were 100% α(1-4), five strains were 100% β(1-4), nine strains were mix α(1-4) and 1 (1-4) and three strains were 100% β(1-3).

"In Vivo" Change of the TA Structure

To assess whether structural changes in the structure of TAs from S. aureus strains occur "in vivo", mice were infected with a non-lethal dose of either the HT2005 0742 strain which is a 100% β(1-4) S. aureus strain or the Newman Foster strain which is a mix α(1-4) and β(1-4) S. aureus strain. After a fifteen day period, organs from infected mice were harvested and the structures of TAs from infected organs were analyzed. The protocol used was as follows.

Bacterial suspensions were obtained from a 50 mL culture of the Newman strain or the HT2005 0742 strain grown for 20 hours in TSB at +37° C. Mice were infected via the intraperitoneal route with $1.7 \times 10^6$ CFU/500 µL of the Newman strain or $7 \times 10^6$ CFU/500 µL of the HT2005 0742 strain. Bacterial inocula were prepared extemporaneously by mixing 1:1 sterile 20% hog mucin and 2× concentrated adjusted bacterial suspensions. Fifteen days post infection, mice were euthanized. Livers and kidneys were removed, dissociated and homogenized in sterile PBS. CFUs per organ were enumerated by serial dilution and plating on Tryptic Soy Agar. Kidneys and livers from infected mice that contained at least $6 \times 10^7$ CFUs/kidney and $10^9$ CFUs/liver were selected and further analyzed for TA characterization. The selected organs were ground, washed twice with respectively 5 mL and 1 mL of 0.15 M NaCl. The pellet was suspended in 400 µL of 48% HF and incubated at room temperature overnight. Cell debris was removed by centrifugation, and HF was removed under a stream of nitrogen at 40° C. The samples were then dissolved in 400 µL of water and passed through a centrifugal filter unit (10 kDa MW cut-off, Ultracel-10, Millipore) to remove proteins and other macromolecules. The GlcNAc-Rib disaccharides were separated on a Dionex system and analyzed according to the protocol described in the previous paragraph.

With respect to the HT2005 0742 strain, the results obtained showed that the ribitol residues of the 1,5 ribitol phosphate repeating units were substituted at the 4-position by N-acetyl D-glucosaminyl residues which remained exclusively in the β anomeric configuration. Therefore, there was no change in the TA structure of HT2005 0742 which remained a 100% β(1-4) strain after "in vivo" amplification in the infected organs of mice.

In contrast, it was observed that, following "in vivo" amplification, the Newman Foster strain had a teichoic acid profile in which almost 90% of the N-acetyl D-glucosaminyl residues of the 1,5 ribitol phosphate were in a β(1-4) anomeric configuration. The TA structure of this strain was therefore subject to variations according to growth conditions and the "in vivo" environment favoured a β(1-4) anomeric configuration.

Together, these results suggest that, when S. aureus strains are put in an "in vivo" environment, the structure of the TAs evolves towards a structure wherein the N-acetyl D-glucosaminyl residues on the 1,5 ribitol phosphate are predominantly in a β anomeric configuration.

II) Synthesis and Characterization of the Octamer and Nonamer Oligosaccharides

Materials and Methods:

All chemicals (Acros, Fluka, Merck, Sigma-Aldrich, Interchim) were used as received and reactions were carried out dry, under argon atmosphere, except for those containing water. DNA synthesis grade acetonitrile from Sigma-Aldrich was used for all phosphoramidite coupling reactions. Both the 3 Å and 4 Å molecular sieve powders were activated in an oven at 300° C. at least 12 h before use. Thin-Layer Chromatography (TLC) analysis was conducted on TLC silica gel glass sheets (Merck, silica gel 60, F245) or on basic alumina TLC glass plates (with 254 nm fluorescent indicator, Teledyne Isco). Compounds were visualized by UV absorption (254 nm), by spraying with 20% $H_2SO_4$ in ethanol. Column chromatography was performed on Merck silica gel (0.015-0.040 mm) packed columns. Preparative ionic Dionex chromatography was performed on a Varian PrepStar machine equipped with a CarboPac™ PA-100 column (22×250 mm), a column oven (set to 27° C.), and a UV detector (set to 206 nm). The following eluant was used for elution: phase A-9:1 $H_2O$-MeCN; phase B-9:1 2 M NaCl-MeCN. The elution gradient was as follows (flow rate: 10 mL/min): 9 to 13% phase B linearly for 12 min, 13 to 80% B linearly for 1 min, 80% B for 2 min, 80 to 9% B for 1 min, and 9% B for 2 min.

Optical rotation measurements ($[\alpha]_D^{20}$) were performed on a Perkin Elmer polarimeter (Sodium D-line, λ=589 nm) with a concentration of 10 mg/mL (c=1), unless stated otherwise.

$^1$H NMR spectra were recorded with a Bruker AV 400 (400 MHz), a Bruker AV 500 (500 MHz) or a Bruker DMX 600 (600 MHz). NMR spectra were recorded in $CDCl_3$ with chemical shift (δ) relative to tetramethylsilane, unless stated otherwise. When $D_2O$ was used, $^1$H-NMR spectra were recorded with chemical shift relative (δ) to HDO (4.755 ppm).

LC-MS analyses were performed on HPLC or UPLC/UV detection at 220 nm/single quadrupole MS analyzer with Electrospray ionisation (ESI) source operating in either positive or negative mode.

Method 1

Instrument: HP 1100 MSD (Agilent)

Column: Symmetry C18 (50×2.1 mm) 3.5 µm (Waters); column temp.: 30° C.

Solvent A: $H_2O$+0.005% TFA; Solvent B: $CH_3CN$+0.005% TFA

Flow rate: 0.4 mL/min

Gradient A/B: 100/0 (t0 min) to 0/100 (t10 min) hold 0/100 (t15 min)

Method 2
Instrument: UPLC Acquity SQD (Waters)
Column: BEH C18 (50×2.1 mm) 1.7 μm (Waters); column temp.: 55° C.
Solvent A: $H_2O$+0.02% HCOOH; Solvent B: $CH_3CN$+0.02% HCOOH
Flow rate: 1 mL/min
Gradient A/B: 98/2 (t0 min) to 2/98 (t4 min) hold 2/98 (t4.5 min)
Method 3
Instrument: UPLC Acquity SQD (Waters)
Column: BEH C18 Shield (100×2.1 mm) 1.7 μm (Waters); column temp.: 65° C.
Solvent A: $H_2O$+0.02% HCOOH; Solvent B: $CH_3CN$+0.02% HCOOH
Flow rate: 0.7 mL/min
Gradient A/B: 95/5 (t0 min) to 75/25 (t0.5 min) to 40/60 (t7 min) to 15/85 (t9.7 min) to 2/98 (t10 min) hold 2/98 (t10.5 min)
Method 4
Instrument: UPLC Acquity SQD (Waters)
Column: CSH C18 (50×2.1 mm) 1.7 μm (Waters); column temp.: 55° C.
Solvent A: $H_2O$+0.02% HCOOH; Solvent B: $CH_3CN$+0.02% HCOOH
Flow rate: 1 mL/min
Gradient A/B: 98/2 (t0 min) to 2/98 (t4 min) hold 2/98 (t4.5 min)
Method 5
Instrument: HP 1100 MSD (Agilent)
Column: X Terra MS C8 3.5 μm (100×3.0 mm) Waters); column temp.: 30° C.
Solvent A: $H_2O$+$NH_4OAc$ 10 mM pH 7; Solvent B: $CH_3CN$
Flow rate: from 0.6 mL/min at t0 min to 0.4 mL/min at t12 min
Gradient A/B: 70/30 (t0 min) to 5/95 (t12 min) hold 5/95 (t36 min)
Method 11
Instrument: HP 1100 MSD (Agilent)
Column: Kinetex C18 (50×3.0 mm) 2.6 μm (Phenomenex); column temp.: 30° C.
Solvent A: $H_2O$+0.05% TFA; Solvent B: $CH_3CN$+0.035% TFA
Flow rate: 0.8 mL/min
Gradient A/B: 7/3 (t0 min) to 0/1 (t30 min) hold 0/1 (t35 min)
Methods 12a and 12b
Instrument: UPLC Acquity SQD (Waters)
Column: BEH C18 (50×2.1 mm) 1.7 μm (Waters); column temp.: 55° C.
Solvent A: $H_2O$+0.02% HCOOH; Solvent B: $CH_3CN$+0.02% HCOOH
Flow rate: 1 mL/min
a: Gradient A/B: 95/5 (t0 min) to 2/98 (t2 min) hold 2/98 (t2.5 min)
b: Gradient A/B: 95/5 (t0 min) to 0/100 (t2 min) hold 0/1 (t2.5 min)
LC-HRMS analyses were performed on a UPLC Acquity/ESI Tof mass spectrometer LCT-Premier XE (Waters) operating in either positive or negative mode.
Method 6
Column: BEH300 C4 (100×2.1 mm) 1.7 μm (Waters); column temp.: 70° C.
Solvent A: $H_2O$+0.005% TFA; Solvent B: $CH_3CN$+0.005% TFA
Flow rate: 0.6 mL/min (split 1/20 into ion source)
Gradient A/B: 7/3 (t0 min) to 0/1 (t10 min) hold 0/1 (t15 min)
Method 7
Column: BEH300 C4 (100×2.1 mm) 1.7 μm (Waters); column temp.: 70° C.
Solvent A: $H_2O$+0.1% TFA; Solvent B: $CH_3CN$+0.1% TFA
Flow rate: 0.6 mL/min (split 1/20 into ion source)
Gradient A/B: 7/3 (t0 min) to 0/1 (t10 min) hold 0/1 (t15 min)
CE Capillary Zone Electrophoresis was performed on P/ACE MDQ (Beckman) system.
Methods 8a and 8b
Capillary: PVA coated 50 μm (id), effective length: 40 cm
Buffer: 5-sulfosalicylic acid, 4 mM
a: pH-3.51 (NaOH)
b: pH-3.64 (NaOH)
Voltage: −15 kV
Temperature: 25° C.
Injection: 5 sec (0.5 psi) solution at 0.5 mg/mL in $H_2O$ co-injected with 5 sec (0.5 psi) DMSO
Detection: indirect UV 214 nm
SFC-MS analyses were performed on SFC (Berger)/UV detector (Agilent) at 220 nm/single quad. mass spectrometer ZQ (Waters) with Electrospray ionisation (ESI) source operating in positive mode. Solvent make-up, delivered by HP1100 (Agilent pump), was added after back pressure regulator and before ion source.
Method 9
Column: Diol 60A (250×4.6 mm) 5 μm (Princeton); column temp.: 34° C.
Supercritical fluid: $CO_2$, pressure: 180 bars, temp.: 40° C.
Modifier: MeOH/$CH_3CN$ 1/1 (V/V)
Modifier gradient: from 5% (t2 min) to 40% (t13.7 min) at 3%/min, hold at 40% during 1 min
Flow rate: 3 mL/min
Make-up Solvent: MeOH+0.2% HCOOH at 0.2 mL/min
Method 10
Column: Diol 60A (250×4.6 mm) 5 μm (Princeton); column temp.: 36° C.
Supercritical fluid: $CO_2$, pressure: 180 bars, temp.: 40° C.
Modifier: MeOH
Modifier gradient: from 5% (t1 min) to 40% (t12.7 min) at 3%/min, hold at 40% during 2 min
Flow rate: 3 mL/min
Make-up Solvent: MeOH+0.2% HCOOH at 0.2 mL/min
ESI HRMS spectra were obtained on ESI Tof mass spectrometer LCT-Premier XE (Waters) by infusing solutions at 1 μg/μL with a flow rate of 5 μL/min operating in either positive or negative mode.
High resolution mass spectra (HRMS) were recorded by direct injection (2 μl of a 2 μM solution in 1/1 water/acetonitrile and either 0.1% formic acid or 10 mM ammonium formate for the oligomers) on a mass spectrometer (Thermo Finnigan LTQ Orbitrap) equipped with an electrospray ion source in positive mode (source voltage 3.5 kV, sheath gas flow 10, capillary temperature 275° C.) with resolution R=60000 at m/z 400 (mass range m/z=150-2000) and dioctylphthalate (m/z=391.28428) as a lock mass. The high resolution mass spectrometer was calibrated prior to measurements with a calibration mixture (Thermo Finnigan).

Example 1—Synthesis of the β(1,4) Octamer

4-O-(2-acetamido-2-deoxy-β-D-glucopyranosyl)-5-O-(4-O-(2-acetamido-2-deoxy-β-D-glucopyranosyl)-5-O[4-O-(2-acetamido-2-deoxy-β-D-glucopyranosyl)-5-O-(4-O-(2-acetamido-2-deoxy-β-D-glucopyranosyl)-5-O[4-O-(2-acetamido-2-deoxy-β-D-glucopyranosyl)-5-O-{4-O-(2-acetamido-2-deoxy-β-D-glucopyranosyl)-5-O-{4-O-(2-acetamido-2-deoxy-β-D-glucopyranosyl)-5-O-{4-O-(2-acetamido-2-deoxy-β-D-glucopyranosyl)-1-O-[sodium phosphinato]-D-ribitol}-1-O-[sodium phosphinato]-D-ribitol]-1-O-[sodium phosphinato]-D-ribitol}-1-O[sodium phosphinato]-D-ribitol]-1-O-[sodium phosphinato]-D-ribitol}-1-O-[sodium phosphinato]-D-ribitol]-1-O-[sodium phosphinato]-D-ribitol)-1-O[(2-[(4-hydrazino-4-oxobutanoyl)amino]ethoxy)(sodium phosphinato)]-D-ribitol (1)

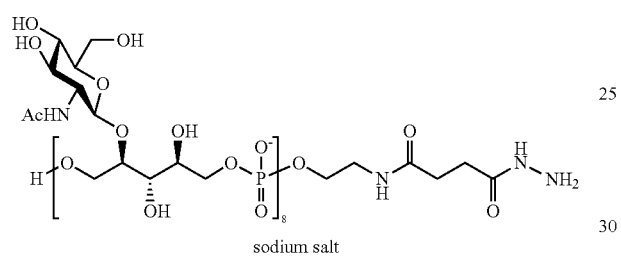

Scheme 1

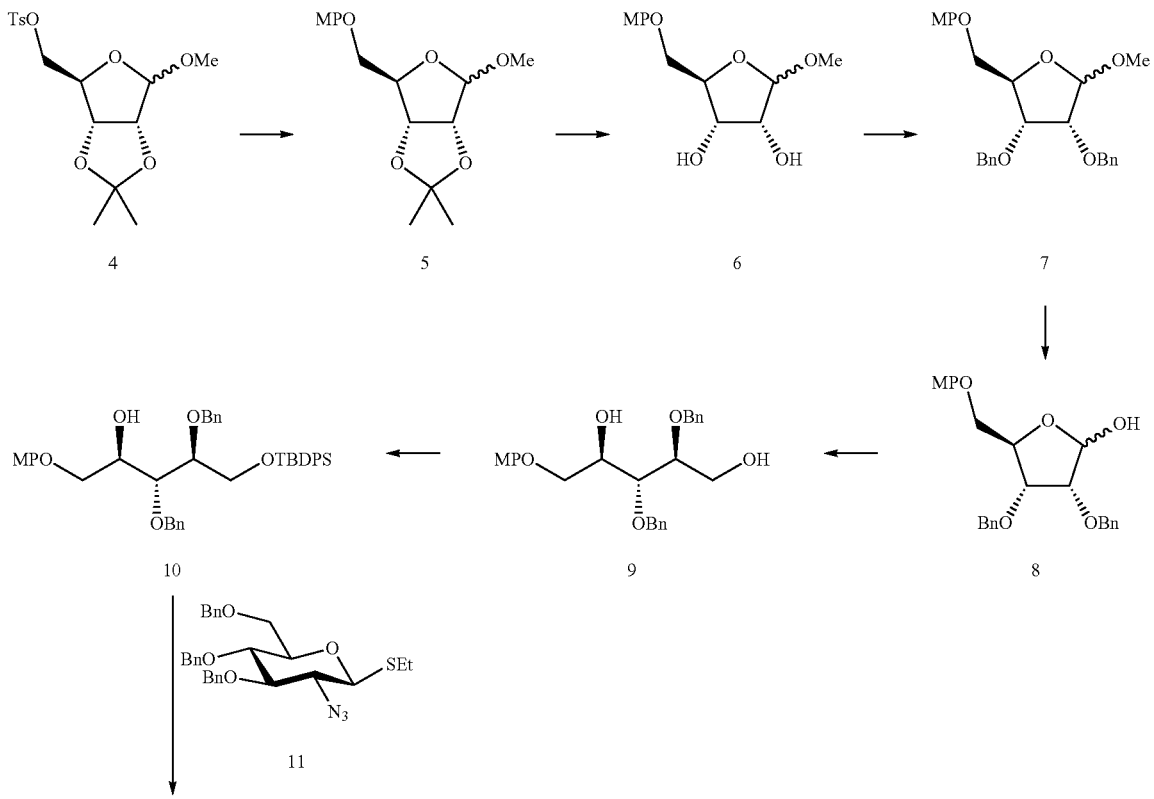

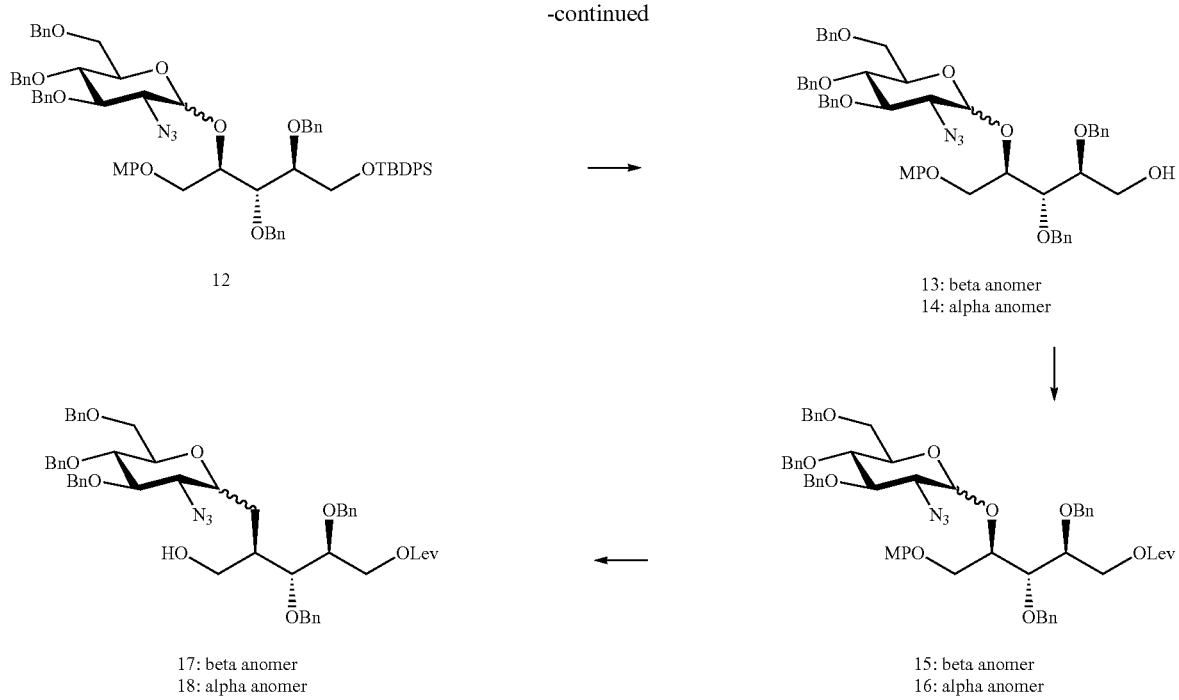

17: beta anomer
18: alpha anomer

15: beta anomer
16: alpha anomer

Step 1.1: methyl 2,3-O-isopropylidene-5-O-(4-methoxyphenyl)-D-ribofuranoside (5)

Cesium carbonate (50 g, 153 mmol) and MIBK (50 mL) were added to a solution of 4-methoxyphenol (17.3 g, 140 mmol) in MIBK (64 mL). The mixture was stirred at 110° C. and a solution of methyl 2,3-O-isopropylidene-5-O-tosyl-D-ribofuranoside (4) (50 g, 140 mmol) [Baird, Lynton J. et al, *Journal of Organic Chemistry*, 2009, 74(6), 2271-2277] in MIBK (140 mL) was added dropwise followed by MIBK (50 mL). After further stirring at 105° C. overnight, the brown mixture was cooled to rt, diluted with MIBK and washed with water. The organic layer was dried over sodium sulfate, filtered and concentrated in vacuo to give target compound 5 that was used without further purification in the following step.

LC-MS (method 1) m/z 333.2 [(M+Na)$^+$]; RT=8.53 min

Step 1.2: methyl 5-O-(4-methoxyphenyl)-D-ribofuranoside (6)

An aqueous solution of sulfuric acid 1N (56 mL) was added dropwise to a solution of 5 (140 mmol) in methanol (405 mL). The solution was stirred at reflux for 5 h. The solution was cooled to 0° C. and sodium hydrogen carbonate was added portionwise until neutral pH was reached. The mixture was filtered on Celite® and the filtrate was concentrated in vacuo. The residue obtained was purified by flash chromatography on silica gel (toluene/EtOAc 7/3 to 1/1) to afford 32 g (84% yield over 2 steps) of target compound 6.

LC-MS (method 1) m/z 293.1 [(M+Na)$^+$]; RT=5.64 and 5.76 min

Step 1.3: methyl 2,3-di-O-benzyl-5-O-(4-methoxyphenyl)-D-ribofuranoside (7)

Sodium hydride (60% suspension in oil, 8.79 g, 0.22 mol) was added portionwise to a solution of compound 6 (66 g, 0.18 mol) in DMF (0.9 L) at 0° C. under argon. After stirring at 0° C. for 20 min, benzyl bromide (31.3 mL, 0.26 mol) was added dropwise. The reaction mixture was stirred overnight at rt and MeOH (7 mL) was added dropwise at 0° C. After stirring at rt for 30 min, the mixture was concentrated in vacuo, diluted with AcOEt and washed with water. The organic layer was washed with water twice, dried over sodium sulfate, filtered and concentrated in vacuo. The residue obtained was purified by flash chromatography on silica gel (toluene/EtOAc 1/0 to 4/1) to afford 74.9 g (91% yield) of target compound 7.

LC-MS (method 2) m/z 468.2 [(M+NH$_4$)$^+$]; RT=2.65 min

Step 1.4: 2,3-di-O-benzyl-5-O-(4-methoxyphenyl)-D-ribofuranose (8)

A 3 M aqueous solution of hydrogen chloride (208 mL) was added slowly at rt to a solution of compound 7 (95.5 g, 0.21 mol) in 1,4-dioxane (1.2 L). The mixture was heated at reflux for 5 h and cooled down to 0° C. An aqueous saturated solution of hydrogen carbonate was added dropwise to the reaction mixture at 0° C. in order to reach pH 9. After dilution with EtOAc (500 mL), the organic layer was washed with water and brine. The aqueous phase was extracted with EtOAc (3×200 mL) and the resulting organic layer was washed with brine. The combined organic phases were dried over sodium sulfate, filtered and concentrated in vacuo. The residue obtained was purified by flash chromatography on silica gel (toluene/EtOAc 1/0 to 7/3) to afford 57.6 g (62% yield) of target compound 8.

LC-MS (method 2) m/z 454.2 [(M+NH$_4$)$^+$]; RT=2.46 and 2.51 min

Step 1.5: 2,3-di-O-benzyl-5-O-(4-methoxyphenyl)-D-ribitol (9)

Sodium borohydride (8.84 g, 0.23 mol) was added portionwise to a solution of compound 8 (78.5 g, 0.18 mol) in MeOH (1.2 L) at 0° C. After stirring at 0° C. for 1 h and 30 min at rt, the reaction mixture was diluted with DCM (1 L). The organic solution was washed with water and brine, dried over sodium sulfate, filtered and concentrated in vacuo to give target compound 9 as a colorless syrup that was used without further purification in the following step.

Step 1.6: 2,3-di-O-benzyl-5-O-(4-methoxyphenyl)-1-O-tert-butyldiphenylsilyl-D-ribitol (10)

To the solution of crude compound 9 (7.73 g, 17.63 mmol) in DCM (140 mL) at 0° C. were successively added triethylamine (6.21 mL, 44.1 mmol), DMAP (1.1 g, 8.8 mmol), and tert-butyldiphenylchlorosilane (9.32 mL, 35.3 mmol). The reaction mixture was stirred overnight at rt. After dilution with DCM (800 mL), the organic solution was washed with 10% aqueous solution of potassium sulfate (200 mL), water (3×150 mL), 2% aqueous solution of sodium hydrogen carbonate (150 mL) and water (150 mL). The resulting organic phase was dried over sodium sulfate, filtered and concentrated in vacuo. The residue obtained was purified by flash chromatography on silica gel (toluene/EtOAc 1/0 to 9/1) to give 10.6 g (89% yield) of target compound 10.

LC-MS (method 2) m/z 677.3 [(M+H)$^+$]; RT=3.73 min

Step 1.7: 4-O-[2-azido-3,4,6-tri-O-benzyl-2-deoxy-α,β-D-glucopyranosyl]-2,3-di-O benzyl-5-O-(4-methoxyphenyl)-1-tert-butyldiphenylsilyl-D-ribitol (12)

A mixture of compound 10 (5.17 g, 7.64 mmol), ethyl 2-azido-3,4,6-tri-O-benzyl-2-deoxy-1-thio-β-D-glucopyranoside (11) (5.64 g, 993 mmol) [Y. Du, J. Lin, R. J. Linhardt, *Journal of Carbohydrate Chemistry*, 1997, 16(9), 1327-1344] and 4 Å powdered molecular sieves (11.5 g) in anhydrous DCM (153 mL) and Et$_2$O (230 mL) was stirred for 2.5 h at rt under dry argon. N-Iodosuccinimide (4.30 g, 19.09 mmol) and triflic acid (167 μL, 1.91 mmol) were added at −20° C. to the mixture which was stirred for a further 10 min. Triethylamine (535 μL, 4.06 mmol) is added, and the mixture is filtered over a pad of Celite® and diluted with DCM (600 mL). The organic layer was then washed with 1 M Na$_2$S$_2$O$_3$ aqueous solution (3×150 mL), with water (3×150 mL), dried over sodium sulfate, filtered and concentrated in vacuo. Flash chromatography of the residue on a column of silica gel with toluene-EtOAc gave the expected product 12 (8.63 g, 7.61 mmol) as a 52:48 α/β mixture with 94% yield.

LC-MS (method 3) m/z 1156.1 [(M+Na)$^+$]; RT=4.24 min

Step 1.8: 4-O-(2-azido-3,4,6-tri-benzyl-2-deoxy-β-D-glucopyranosyl)-2,3-di-O-benzyl-5-O-(4-methoxyphenyl)-D-ribitol (13)

4-O-(2-azido-3,4,6-tri-benzyl-2-deoxy-α-D-glucopyranosyl)-2,3-di-benzyl-5-O-(4-methoxyphenyl)-D-ribitol (14)

Acetic acid (13.9 mL, 0.24 mol) and a 1 M solution of TBAF in THF (244 mL, 0.24 mol) were successively added to a solution of compound 12 (9.22 g, 8.13 mmol) in THF (325 mL) at 0° C. The solution was stirred at rt for 17 h and concentrated in vacuo. The residue was dissolved in DCM (800 mL) and the solution was washed with water (3×200 mL), 2% NaHCO$_3$ aqueous solution (3×100 mL) and water. The organic layer was dried over sodium sulfate, filtered and concentrated in vacuo. The residue obtained was purified by flash chromatography on silica gel (toluene/EtOAc 1/0 to 4/1) to give 2.94 g (40%) of β-anomer compound 13 and 3.37 g (46%) of α-anomer compound 14, both as a colourless oil.

13: Rf=0.63 silica gel, toluene/EtOAc: 4/1
LC-MS (method 3) m/z 896.3 [(M+H)$^+$]; RT=3.66 min
δH (600 MHz, CDCl$_3$) 7.35-7.14 (m, 25H), 6.81 (4H, s), 4.90 (1H, d), 4.76-4.80 (3H, m), 4.71 (1H, d), 4.66 (1H, d), 4.65 (1H, d, J$_{1'-2'}$=7.7 Hz), 4.62 (1H, d), 4.54 (1H, d), 4.52 (1H, d), 4.47 (1H, d), 4.37 (1H, ddd), 4.20 (1H, dd), 4.06 (1H, dd), 4.00 (1H, dd), 3.91 (1H, m), 3.88 (1H, dd), 3.78 (1H, dd), 3.77 (3H, s), 3.64 (1H, dd), 3.60 (1H, dd), 3.52 (1H, dd), 3.41 (1H, ddd), 3.39 (1H, dd), 3.38 (1H, dd).

14: Rf=0.49 silica gel, toluene/EtOAc: 4/1
LC-MS (method 3) m/z 896.3 [(M+H)$^+$]; RT=3.63 min
δH (600 MHz, CDCl$_3$) 7.35-7.15 (m, 25H), 6.77-6.70 (4H, m), 5.18 (1H, d, J$_{1'-2'}$=3.7 Hz), 4.86 (1H, d), 4.82 (1H, d), 4.79 (1H, d), 4.78 (1H, d), 4.70 (1H, d), 4.68 (1H, d), 4.61 (1H, d), 4.59 (1H, d), 4.54 (1H, d), 4.44 (1H, d), 4.31 (1H, dt), 4.14 (1H, ddd), 4.08 (2H, m), 3.99 (1H, dd), 3.95 (1H, dd), 3.84 (3H, m), 3.77 (3H, s), 3.76 (1H, dd), 3.70 (1H, dd), 3.54 (1H, dd), 3.52 (1H, dd).

Step 1.9: 4-O-(2-azido-3,4,6-tri-O-benzyl-2-deoxy-β-D-glucopyranosyl)-2,3-di-O-benzyl-1-O-levulinoyl-5-O-(4-methoxyphenyl)-D-ribitol (15)

To a solution of compound 13 (1.96 g, 2.18 mmol) in anhydrous DCM (2.6 mL) and 1,4-dioxane (26 mL) were successively added levulinic acid (0.45 mL, 2.18 mmol), DMAP (53 mg, 0.43 mmol) and EDCl (0.84 g, 4.37 mmol) at 0° C. After stirring at rt for 15 h, the solution was diluted with DCM, washed with 10% aqueous potassium sulfate solution, water, saturated aqueous sodium hydrogen carbonate and brine. The organic phase was dried sodium sulfate, filtered off and concentrated in vacuo to give target compound 15 as an oil that was used without further purification in the following step.

Rf=0.52 silica gel, toluene/EtOAc 4/1

Step 1.10: 4-O-(2-azido-3,4,6-tri-O-benzyl-2-deoxy-β-D-glucopyranosyl)-2,3-di-O-benzyl-1-O-levulinoyl-D-ribitol (17)

CAN (3.6 g, 6.57 mmol) was added portionwise to a solution of compound 15 (2.18 mmol) in acetonitrile (200 mL) and water (22 mL) cooled at 0° C. The reaction mixture was stirred at rt for 2 h, concentrated in vacuo, diluted with DCM (1.8 L), washed with water, 2% aqueous sodium hydrogen carbonate and brine. The organic layer was dried over sodium sulfate, filtered and concentrated in vacuo. The residue obtained was purified by flash chromatography on silica gel (toluene/EtOAc 1/0 to 7/3) to give 1.94 g (81% yield) of target compound 17.

LC-MS (method 2) m/z 905.3 [(M+NH$_4$)$^+$]; RT=3.45 min

Scheme 2

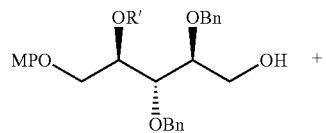

beta series   13
alpha series  14

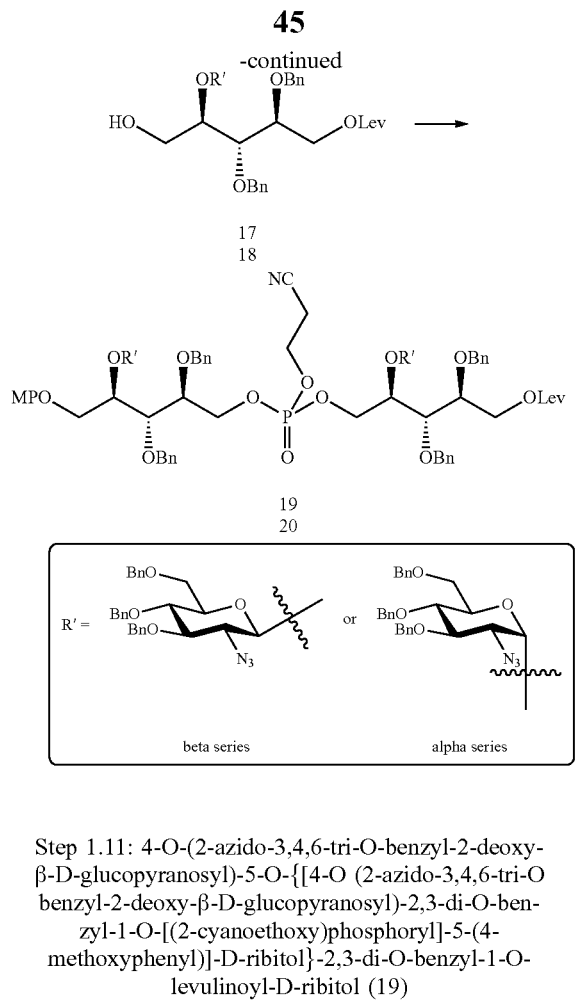

Step 1.11: 4-O-(2-azido-3,4,6-tri-O-benzyl-2-deoxy-β-D-glucopyranosyl)-5-O-{[4-O (2-azido-3,4,6-tri-O benzyl-2-deoxy-β-D-glucopyranosyl)-2,3-di-O-benzyl-1-O-[(2-cyanoethoxy)phosphoryl]-5-(4-methoxyphenyl)]-D-ribitol}-2,3-di-O-benzyl-1-O-levulinoyl-D-ribitol (19)

Each compound 13 and 17 were separately dissolved in anhydrous MeCN and concentrated in vacuo to give white foam. The procedure was repeated at least twice prior to reaction. All chemicals and glassware were dried overnight in vacuo over $P_2O_5$ and potassium hydroxide pellets before use.

A mixture of compound 13 (1.78 g, 1.99 mmol) and activated molecular sieves (3 Å powder, 0.66 g) in dry MeCN (50 mL) under argon was stirred at rt for 1 h. The mixture was cooled to 0° C. and N,N-diisopropylethylamine (0.83 mL, 4.77 mmol) and chloro-2-cyanoethyl-N,N-diisopropylphosphoramidite (0.59 mL, 2.58 mmol) were successively added dropwise under argon. After further stirring at 0° C. for 0.5 h, the mixture of the activated phosphoramidite was cooled to −10° C. before transfer.

Simultaneously a mixture of compound 17 (1.18 g, 1.33 mmol) and activated molecular sieves (3 Å powder, 0.66 g) in dry MeCN (50 mL) under argon was stirred at rt for 1 h. The mixture was cooled to −10° C. and the mixture containing the activated phosphoramidite was added followed by the addition of 5-ethylthio-1H-tetrazole (2.07 g, 15.9 mmol). After stirring for 1 h at 0° C., dry pyridine (3.25 mL, 40 mmol) was added at 0° C., followed by a 0.4 M solution of iodine (in THF/water 2/1) until a brown color persisted. The reaction mixture was filtered over Dicalite®. The filtrate was diluted with DCM, washed with 1 M aqueous solution of sodium thiosulfate, 2% aqueous solution of sodium hydrogen carbonate, water and brine. The organic layer was dried over sodium sulfate, filtered and concentrated in vacuo. The residue obtained was purified by flash chromatography on silica gel (toluene/acetone 1/0 to 3/2) to give 1.74 g (69% yield) of target compound 19.

LC-MS (method 4) m/z 1920.8 [(M+Na)$^+$]; RT=4.15 min

Scheme 3

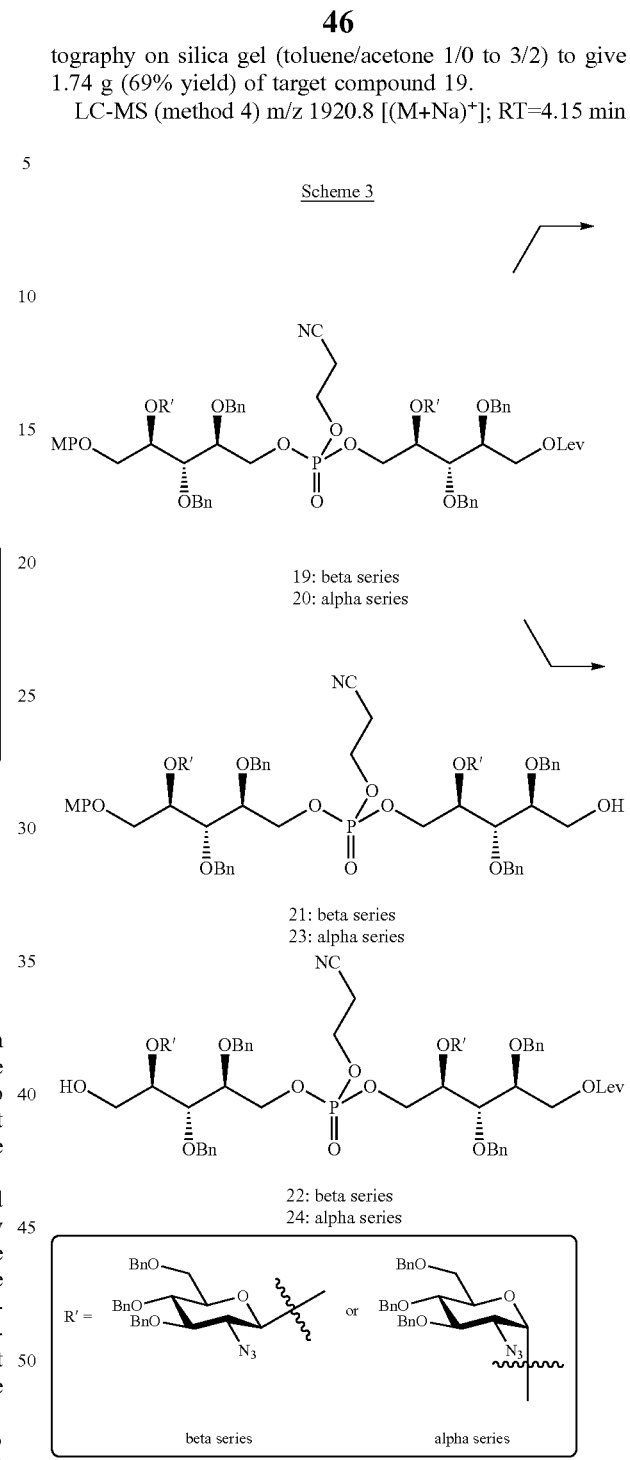

Step 1.12: 4-O-(2-azido-3,4,6-tri-O-benzyl-2-deoxy-β-D-glucopyranosyl)-5-O-{[4-O-(2-azido-3,4,6-tri-O-benzyl-2-deoxy-β-D-glucopyranosyl)-2,3-di-O-benzyl-1-O-[(2-cyanoethoxy)phosphoryl]-5-O-(4-methoxyphenyl)]-D-ribitol}-2,3-di-O-benzyl-D-ribitol (21)

A freshly prepared solution of hydrazine hydrate (2.66 mL, 30.0 mmol) in pyridine (48 mL) and acetic acid (32 mL) at 0° C. was added dropwise to a solution of compound 19 (10.2 g, 5.36 mmol) in pyridine (80 mL) at 0° C. After further stirring at 0° C. for 0.5 h, the solution was diluted with DCM and washed with a saturated aqueous solution of sodium hydrogen carbonate and water. The organic layer was dried over sodium sulfate, filtered and concentrated in vacuo. The residue obtained was purified by flash chromatography on silica gel (toluene/acetone 1/0 to 7/3) to give 8.08 g (83% yield) of target compound 21.

LC-MS (method 5) m/z 1817.6 [(M+NH$_4$)$^+$]; RT=16.55 min

Step 1.13: 4-O-(2-azido-3,4,6-tri-O-benzyl-2-deoxy-β-D-glucopyranosyl)-5-O-{[4-O-(2-azido-3,4,6-tri-O-benzyl-2-deoxy-β-D-glucopyranosyl)-2,3-di-O-benzyl-1-O-[(2-cyanoethoxy)phosphoryl]]-D-ribitol}-2,3-di-O-benzyl-1-O-levulinoyl-D-ribitol (22)

Compound 19 (7.84 g, 4.13 mmol) was treated according to the procedure described in Step 1.10 to give 5.81 g (79% yield) of target compound 22 after purification by flash chromatography on silica gel (toluene/acetone 1/0 to 7/3).

LC-MS (method 5) m/z 1809.6 [(M+NH$_4$)$^+$]; RT=16.02 min

Step 1.14: 4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-2,3-di-O-benzyl-1-O-[(2-cyanoethoxy)phosphoryl]-5-O-(4-methoxyphenyl)-D-ribitol}-2,3-di-O-benzyl-1-[(2-cyanoethoxy)phosphoryl]-D-ribitol}-2,3-di-O-benzyl-1-O[(2-cyanoethoxy)phosphoryl]-D-ribitol)-2,3-di-O-benzyl-1-O-levulinoyl-D-ribitol (25)

Compound 21 (1.0 g, 0.56 mmol) was reacted according to the procedure described in Step 1.11 with chloro-2-cyanoethyl-N,N-diisopropylphosphoramidite (166 µL, 0.72 mmol) and compound 22 (0.71 mg, 0.39 mmol) to give 1.21 g (80% yield) of target compound 25 as a white foam after purification by flash chromatography (toluene/acetone 1/0 to 3/2).

ESI HRMS: $C_{205}H_{222}N_{15}O_{45}P_3$ m/z calcd for [M+Na]$^+$ 3729.47, found 3729.26.

LC (method 5): RT=22.83 min

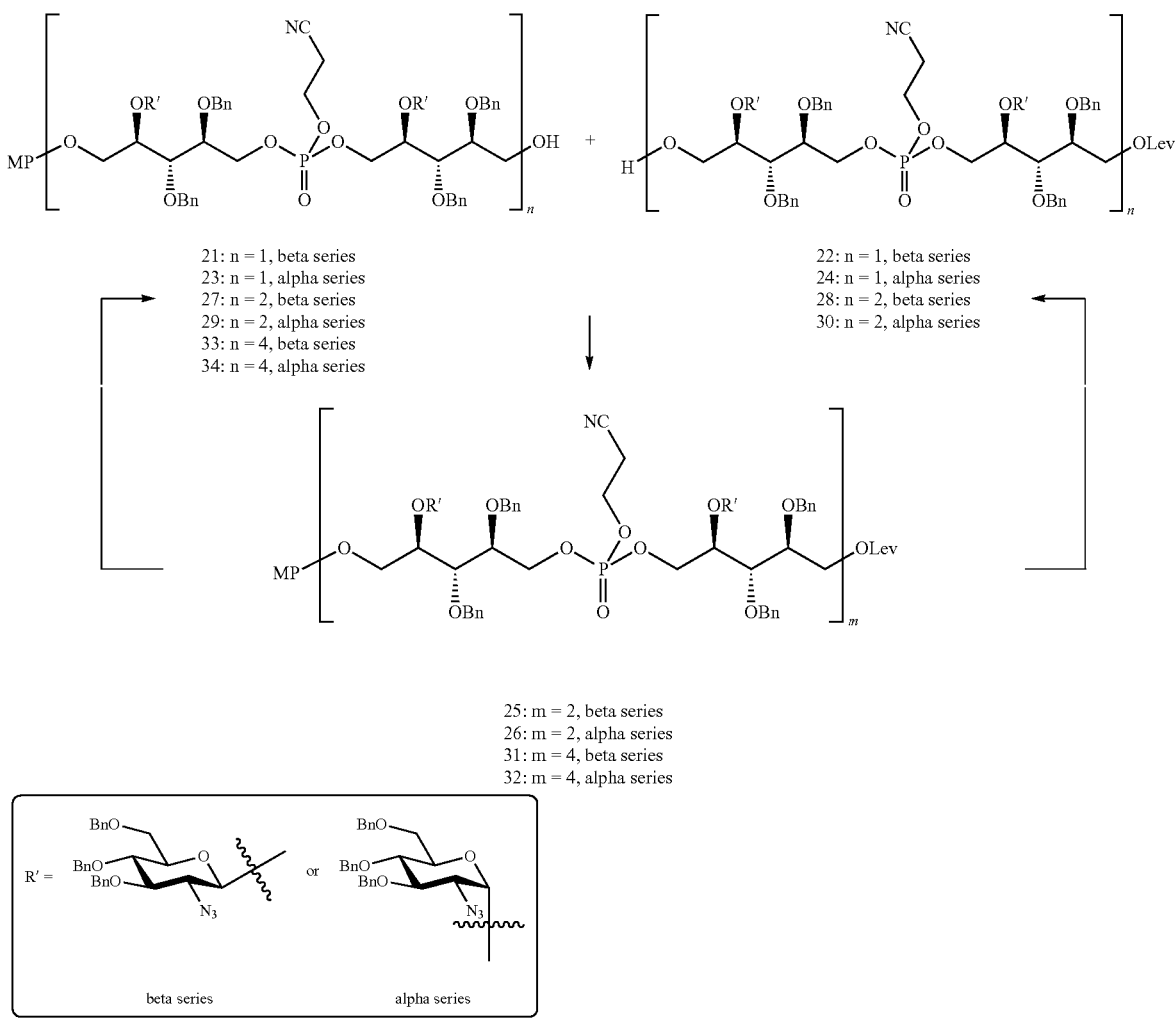

Scheme 4

Step 1.15: 4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-2,3-di-O-benzyl-1-O-[(2-cyanoethoxy)phosphoryl]-5-O-(4-methoxyphenyl)-D-ribitol}-2,3-di-O-benzyl-1-O-[(2-cyanoethoxy)phosphoryl]-D-ribitol]-2,3-di-O-benzyl-1-O-[(2-cyanoethoxy) phosphoryl]-D-ribitol)-2,3-di-O-benzyl-D-ribitol (27)

Compound 25 (5.1 g, 1.38 mmol) was treated according to the procedure described in Step 1.12 to give 3.51 g (71% yield) of target compound 27 as a white foam after purification by flash chromatography on silica gel (toluene/acetone 1/0 to 7/3) and size exclusion chromatography on Sephadex® LH-20 (DCM/MeOH 1/1).

ESI HRMS: $C_{200}H_{216}N_{15}O_{43}P_3$ m/z calcd for $[M+Na]^+$ 3631.43, found 3631.35.

LC (method 5): RT=21.84 min

Step 1.16: 4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-2,3-di-O-benzyl-1-O-[(2-cyanoethoxy) phosphoryl]-D-ribitol)-2,3-di-O-benzyl-1-O-[(2-cyanoethoxy) phosphoryl]-D-ribitol]-2,3-di-O-benzyl-1-O-[(2-cyanoethoxy)phosphoryl]-D-ribitol}-2,3-di-O-benzyl-1-O-levulinoyl-D-ribitol (28)

Compound 25 (4.19 g, 1.13 mmol) was treated according to the procedure described in Step 1.10 to give 3.07 g (76% yield) of target compound 28 as a white foam after purification by flash chromatography on silica gel (toluene/acetone 1/0 to 7/3) and size exclusion chromatography on Sephadex® LH-20 (DCM/MeOH 1/1).

ESI HRMS: $C_{198}H_{216}N_{15}O_{44}P_3$ m/z calcd for $[M+Na]^+$ 3623.43, found 3623.37.

LC (method 5): RT=20.31 min

Step 1.17: 4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-glucopyranosyl)-2,3-di-O-benzyl-1-O-[(2-cyanoethoxy)phosphoryl]-5-O-(4-methoxyphenyl)-D-ribitol)-2,3-di-O-benzyl-1-O{(2-cyanoethoxy)phosphoryl]-D-ribitol]-2,3-di-O-benzyl-1-O-[(2-cyanoethoxy)phosphoryl]-D-ribitol}-2,3-di-O-benzyl-1-O-[(2-cyanoethoxy) phosphoryl] D-ribitol]-2,3-di-O-benzyl-1-O-[(2-cyanoethoxy) phosphoryl]-D-ribitol}-2,3-di-O-benzyl-1-O-[(2-cyanoethoxy)phosphoryl]-D-ribitol]-2,3-di-O-benzyl-1-O-[(2-cyanoethoxy)phosphoryl]D-ribitol}-2,3-di-O-benzyl-1-O-levulinoyl-D-ribitol (31)

Compound 27 (1.5 g, 0.42 mmol) was reacted according to the procedure described in Step 1.11 with chloro-2-cyanoethyl-N,N-diisopropylphosphoramidite (124 µL, 0.54 mmol) and compound 28 (1.20 g, 0.33 mmol) to give 1.73 g (72%/yield) of target compound 31 as a gum after purification by flash chromatography (toluene/acetone 1/0 to 3/2).

LC-HRMS (method 6): $C_{401}H_{434}N_{31}O_{89}P_7$ m/z calcd for $[M+3H]^{3+}$ 2443.63, found 2443.65; RT=9.22 min Step 1.18: 4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-2,3-di-O-benzyl-1-O-[(2-cyanoethoxy)phosphoryl]-5-O-(4-methoxyphenyl)-D-ribitol)-2,3-di-O-benzyl-1-O-[(2-cyanoethoxy)phosphoryl]-D-ribitol]-2,3-di-O-benzyl-1-O-[(2-cyanoethoxy)phosphoryl-D-ribitol)-2,3-di-O-benzyl-1-O-[(2-cyanoethoxy) phosphoryl] D-ribitol]-2,3-di-O-benzyl-1-O-[(2-cyanoethoxy) phosphoryl]-D-ribitol)-2,3-di-O-benzyl-1-O-[(2-cyanoethoxy)phosphoryl]-D-ribitol-2,3-di-O-benzyl-1-O-[(2-cyanoethoxy)phosphoryl]-D-ribitol)-2,3-di-O-benzyl-D-ribitol (33)

Compound 31 (3.23 g, 0.44 mmol) was treated according to the procedure described in Step 1.12 to give 2.54 g (80% yield) of target compound 33 as a white foam after purification by flash chromatography on silica gel (toluene/acetone 1/0 to 7/3) and size exclusion chromatography on Sephadex® LH-20 (DCM/MeOH 1/1).

LC-HRMS (method 6): $C_{396}H_{428}N_{31}O_{87}P_7$ m/z calcd for $[M+3H]^{3+}$ 2410.95, found 2410.95; RT=9.24 min

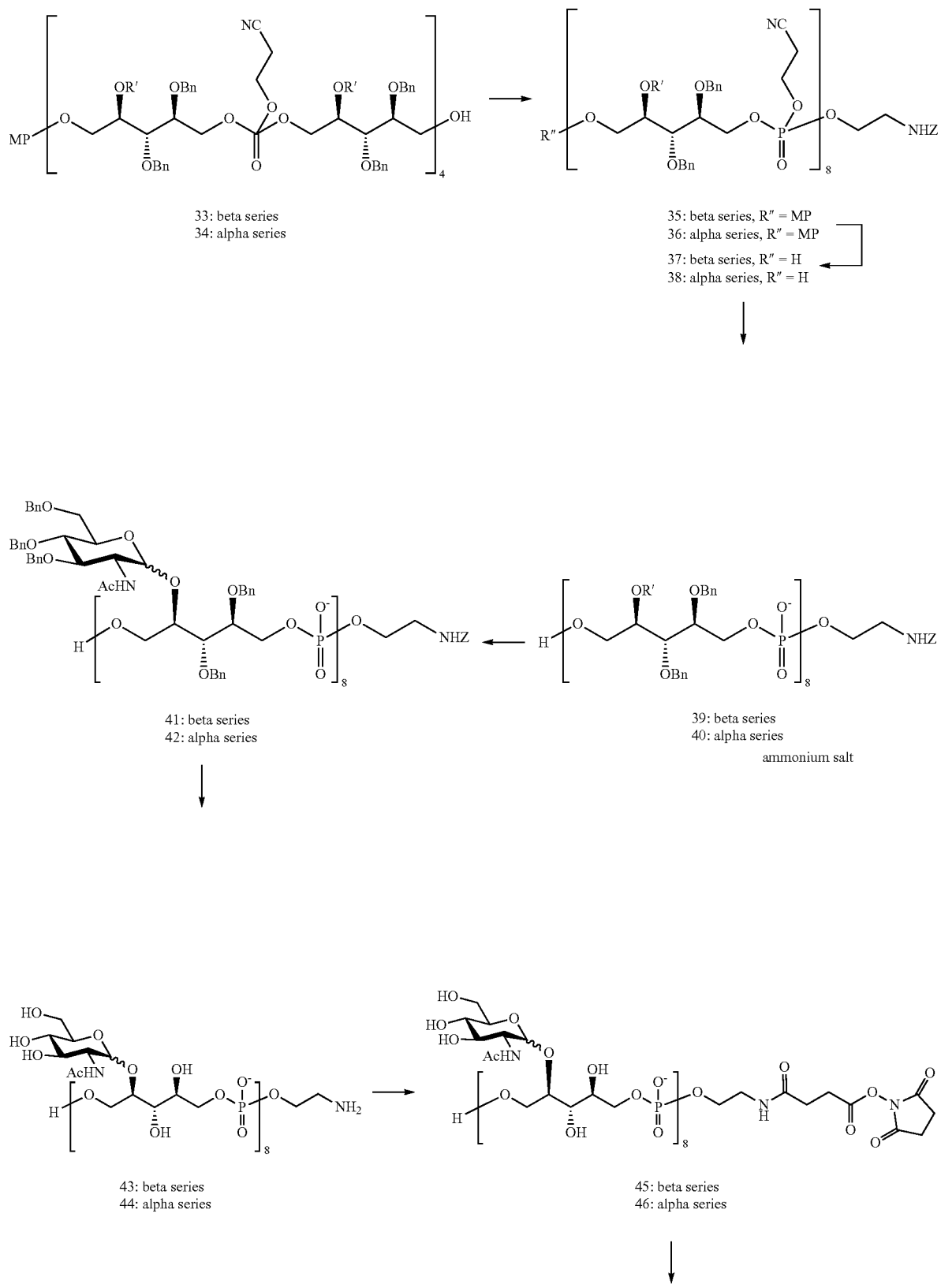
Scheme 5

-continued

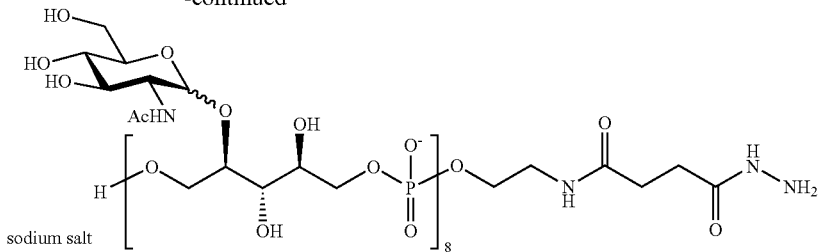

1: beta series
2: alpha series

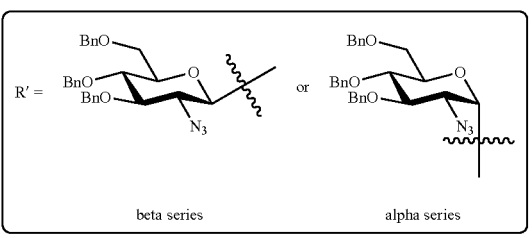

beta series    alpha series

Step 1.19: 4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-2,3-di-O-benzyl-1-O-[(2-cyanoethoxy)phosphoryl]-5-O-(4-methoxyphenyl)-D-ribitol}-2,3-di-O-benzyl-1-O-[(2-cyanoethoxy)phosphoryl]-D-ribitol]-2,3-di-O-benzyl-1-O-[(2-cyanoethoxy)phosphoryl]-D-ribitol}-2,3-di-O-benzyl-1-O-[(2-cyanoethoxy) phosphoryl]-D-ribitol]-2,3-di-O-benzyl-1-O-[(2-cyanoethoxy) phosphoryl]-D-ribitol}-2,3-di-O-benzyl-1-O-[(2-cyanoethoxy)phosphoryl]-D-ribitol]-2,3-di-O-benzyl-1-O-[(2-cyanoethoxy)phosphoryl]-D-ribitol}-2,3-di-O-benzyl-1-O-[(2-{[(benzyloxy)carbonyl]amino}ethoxy)(2-cyanoethoxy)phosphoryl]-D-ribitol (35)

Benzyl N-(2-hydroxyethyl) carbamate (108 mg, 0.55 mmol) was reacted according to the procedure described in Step 1.11 with chloro-2-cyanoethyl-N,N-diisopropylphosphoramidite (115 µL, 0.50 mmol) and compound 33 (800 mg, 0.11 mmol) to give 0.56 g (67% yield) of target compound 35 as a white foam after purification by flash chromatography (toluene/acetone 1/0 to 3/2) and size exclusion chromatography on Sephadex® LH-20 (DCM/MeOH 1/1).

LC-HRMS (method 6): $C_{409}H_{443}N_{33}O_{92}P_8$ m/z calcd for $[M+3H]^{3+}$ 2514.31, found 2514.31; RT=9.19 min Step 1.20: 4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-2,3-di-O-benzyl-1-O-[(2-cyanoethoxy)phosphoryl]-D-ribitol}-2,3-di-O-benzyl-1-O-[(2-cyanoethoxy)phosphoryl]-D-ribitol]-2,3-di-O-benzyl-1-O-[(2-cyanoethoxy) phosphoryl]-D-ribitol}-2,3-di-O-benzyl-1-O-[(2-cyanoethoxy)phosphoryl]-D-ribitol]-2,3-di-O-benzyl-1-O-[(2-cyanoethoxy)phosphoryl]-D-ribitol}-2,3-di-O-benzyl-1-O-[(2-cyanoethoxy)phosphoryl]-D-ribitol]-2,3-di-O-benzyl-1-O-[(2-cyanoethoxy)phosphoryl]-D-ribitol}-2,3-di-O-benzyl-1-O-[(2-{[(benzyloxy)carbonyl]amino}ethoxy)(2-cyanoethoxy) phosphoryl]-D-ribitol (37)

Compound 35 (550 mg, 72.9 µmol) was treated according to the procedure described in Step 1.10 to give 414 mg (76% yield) of target compound 37 as a gum after purification by flash chromatography on silica gel (toluene/acetone 1/0 to 7/3).

LC-HRMS (method 6): $C_{402}H_{437}N_{33}O_{91}P_8$ m/z calcd for $[M+3H]^{3+}$ 2478.96, found 2478.96; RT=9.10 min Step 1.21: 4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-5-O-[4-O-(2-azido-3,4,6-tri-O-benzyl-2-deoxy-β-D-glucopyranosyl)-5-O-{4-O-(2-azido-3,4,6-tri-O-benzyl-2-deoxy-β-D-glucopyranosyl)-2,3-di-O-benzyl-1-O-[ammonium phosphinato]-D-ribitol}-2,3-di-O-benzyl-1-O-[ammonium phosphinato]-D-ribitol}-2,3-di-O-benzyl-1-O-[ammonium phosphinato]-D-ribitol}-2,3-di-O-benzyl-1-O-[ammonium phosphinato]-D-ribitol]-2,3-di-O-benzyl-1-O-[ammonium phosphinato]-D-ribitol}-2,3-di-O-benzyl-1-O-[ammonium phosphinato]-D-ribitol]-2,3-di-O-benzyl-1-O-[ammonium phosphinato]-D-ribitol}-2,3-di-O-benzyl-1-O-[(2-{[(benzyloxy)carbonyl]amino}ethoxy)(ammonium phosphinato)]-D-ribitol (39)

Ammonium hydroxide (20% solution, 4.6 mL) was added to a solution of compound 37 (380 mg, 51.1 μmol) in MeOH (9.2 mL). The mixture was stirred at reflux for 5 h and cooled to rt. The residue was purified by size exclusion chromatography on Sephadex® LH-20 (DCM/MeOH 1/1) to afford 339 mg (ammonium salt, 95% yield) of target compound 39 as a white gum.

LC-HRMS (method 7): $C_{378}H_{405}N_{25}O_{91}P8$ m/z calcd for $[M+6H]^{2-}$ 3503.32, found 3503.07; RT=8.99 min Step 1.22: 4-O-(2-acetamido-3,4,6-tri-O-benzyl-2-deoxy-β-D-glucopyranosyl)-5-O-{4-O-(2-acetamido-3,4,6-tri-O-benzyl-2-deoxy-β-D-glucopyranosyl)-5-O-[4-O-(2-acetamido-3,4,6-tri-O-benzyl-2-deoxy-β-D-glucopyranosyl)-5-O-{4-O-(2-acetamido-3,4,6-tri-O-benzyl-2-deoxy-β-D-glucopyranosyl)-5-O-[4-O-(2-acetamido-3,4,6-tri-O-benzyl-2-deoxy-β-D-glucopyranosyl)-5-O-{4-O-(2-acetamido-3,4,6-tri-O-benzyl-2-deoxy-β-D-glucopyranosyl)-5-O-[4-O-(2-acetamido-3,4,6-tri-O-benzyl-2-deoxy-β-D-glucopyranosyl)-5-O-{4-O-(2-acetamido-3,4,6-tri-O-benzyl-2-deoxy-β-D-glucopyranosyl)-2,3-di-O-benzyl-1-O-[sodium phosphinato]-D-ribitol}-2,3-di-O-benzyl-1-O-[sodium phosphinato]-D-ribitol]-2,3-di-O-benzyl-1-O-[sodium phosphinato]-D-ribitol}-2,3-di-O-benzyl-1-O-[sodium phosphinato]-D-ribitol]-2,3-di-O-benzyl-1-O-[sodium phosphinato]-D-ribitol}-2,3-di-O-benzyl-1-O-[sodium phosphinato]-D-ribitol]-2,3-di-O-benzyl-1-O-[sodium phosphinato]-D-ribitol}-2,3-di-O-benzyl-1-O-[(2-{[(benzyloxy)carbonyl]amino}ethoxy)(sodium phosphinato)]-D-ribitol (41)

Thioacetic acid (1.38 mL, 18.8 mmol) was added to a solution of compound 39 (335 mg, 46.9 μmol) in pyridine (1.4 mL). After stirring at rt over 3.5 days, the mixture was purified by size exclusion chromatography on Sephadex® LH-20 (DCM/MeOH 1/1) to afford 324 mg (97% yield) of target compound 41 as a gum.

LC-HRMS (method 6): $C_{394}H_{437}N_9O_{99}P_8$ 8- m/z calcd for $[M+5H]^{3-}$ 2378.26, found 2378.14; RT=8.38 min Step 1.23: 4-O-(2-acetamido-2-deoxy-β-D-glucopyranosyl)-5-O-{4-O-(2-acetamido-2-deoxy-β-D-glucopyranosyl)-5-O-[4-O-(2-acetamido-2-deoxy-β-D-glucopyranosyl)-5-O-{4-O-(2-acetamido-2-deoxy-β-D-glucopyranosyl)-5-O-[4-O-(2-acetamido-2-deoxy-β-D-glucopyranosyl)-5-O-{4-O-(2-acetamido-2-deoxy-β-D-glucopyranosyl)-5-O-[4-O-(2-acetamido-2-deoxy-β-D-glucopyranosyl)-5-O-{4-O-(2-acetamido-2-deoxy-β-D-glucopyranosyl)-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[(2-aminoethoxy)(sodium phosphinato)]-D-ribitol (43)

Sodium (600 mg, 26.1 mmol) was added portionwise at −78° C. to a stirred solution of compound 41 (310 mg, 43.5 μmol) in dry THF (31 mL) saturated with liquid ammonia. After stirring for 30 min at −78° C., a saturated solution of aqueous ammonium chloride (50 mL) was added dropwise at −78° C. After further stirring for 1 h, the mixture was concentrated in vacuo and diluted with water. The mixture was purified by size-exclusion chromatography on Sephadex® G25 (0.2 M NaCl) and then Sephadex® G25 (water) to give 142 mg (96% yield) of target compound 43 as a white solid.

ESI HRMS: $C_{106}H_{191}N_9O_{97}P_8$ m/z calcd for $[M+H+_4Na]^{3-}$ 1161.27, found 1161.35.

Step 1.24: 4-O-(2-acetamido-2-deoxy-β-D-glucopyranosyl)-5-O-{4-O-(2-acetamido-2-deoxy-β-D-glucopyranosyl)-5-O-[4-O-(2-acetamido-2-deoxy-β-D-glucopyranosyl)-5-O-{4-O-(2-acetamido-2-deoxy-β-D-glucopyranosyl)-5-O-[4-O-(2-acetamido-2-deoxy-β-D-glucopyranosyl)-5-O-{4-O-(2-acetamido-2-deoxy-β-D-glucopyranosyl)-5-O-[4-O-(2-acetamido-2-deoxy-β-D-glucopyranosyl)-5-O-{4-O-(2-acetamido-2-deoxy-β-D-glucopyranosyl)-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[(2-({4-[(2,5-dioxopyrrolidin-1-yl)oxy]-4-oxobutanoyl}amino)ethoxy)(sodium phosphinato)]-D-ribitol (45)

A solution of compound 43 (80 mg, 22.4 μmol) in water (3.4 mL) was added dropwise under vigorous stirring to a solution of disuccinimidyl succinate (140 mg, 0.45 mmol) and N,N-diisopropylethylamine (86 μL, 0.49 mmol) in DMF (3.4 mL). After stirring at rt for 1 h, the mixture was purified by size exclusion chromatography on Sephadex® G25 (0.2 M NaCl) and then Sephadex® G25 (water) to give 74 mg (88% yield) of target compound 45 as a white solid. CE (method 8a): MT=7.24 min Step 1.25: 4-O-(2-acetamido-2-deoxy-β-D-glucopy-ranosyl)-5-O-{4-O-(2-acetamido-2-deoxy-β-D-glu-copyranosyl)-5-O-[4-O-(2-acetamido-2-deoxy-β-D-glucopyranosyl)-5-O-{4-O-(2-acetamido-2-deoxy-β-D-glucopyranosyl)-5-O-[4-O-(2-acetamido-2-deoxy-β-D-glucopyranosyl)-5-O-{4-O-(2-acetamido-2-deoxy-β-D-glucopyranosyl)-5-O-[4-O-(2-acetamido-2-deoxy-β-D-glucopyranosyl)-5-O-{4-O-(2-acetamido-2-deoxy-β-D-glucopyranosyl)-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[(2-[(4-hydrazino-4-oxobutanoyl)amino]ethoxy)(sodium phosphinato)]-D-ribitol (1)

Hydrazine hydrate (10$^6$ μL, 1.19 mmol) was added to a solution of compound 45 (60 mg, 15.9 μmol) in water (4 mL) at rt. After 5 h, the reaction mixture was purified by size exclusion chromatography on Sephadex® G25 (water), by preparative ionic Dionex chromatography followed by size exclusion chromatography on Sephadex® G25 (water) to give 13 mg (24% yield) of target compound 1 as a white foam.
ESI HRMS: $C_{110}H_{197}N_{11}O_{99}P_8$ m/z calcd for [M+H+Na]$^{6-}$ 588.14, found 588.15.
$^1$H NMR (600 MHz, $D_2O$) δ=4.81 (7H, m), 4.76 (1H, d), 4.22 (7H, m), 4.21-4.03 (30H, m), 4.05 (1H, m), 4.05-3.93 (16H, m), 3.99 (3H, m), 3.89 (1H, m), 3.99-3.82 (16H, m), 3.81 (7H, m), 3.78 (1H, m), 3.77 (1H, m), 3.63 (8H, m), 3.53 (16H, m), 3.50 (2H, m), 2.63 (2H, m), 2.55 (2H, m), 2.16 (21H, s), 2.11 (3H, s).

Example 2—Synthesis of the α(1,4) octamer 4-O-(2-acetamido-2-deoxy-α-D-glucopyranosyl)-5-O-{4-O-(2-acetamido-2-deoxy-α-D-glucopyranosyl)-5-O-[4-O-(2-acetamido-2-deoxy-α-D-glucopyranosyl)-5-O-{4-O-(2-acetamido-2-deoxy-α-D-glucopyranosyl)-5-O-[4-O-(2-acetamido-2-deoxy-α-D-glucopyranosyl)-5-O-{4-O-(2-acetamido-2-deoxy-α-D-glucopyranosyl)-5-O-[4-O-(2-acetamido-2-deoxy-α-D-glucopyranosyl)-5-O-{4-O-(2-acetamido-2-deoxy-α-D-glucopyranosyl)-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[(2-[(4-hydrazino-4-oxobutanoyl)amino]ethoxy)(sodium phosphinato)]-D-ribitol (2)

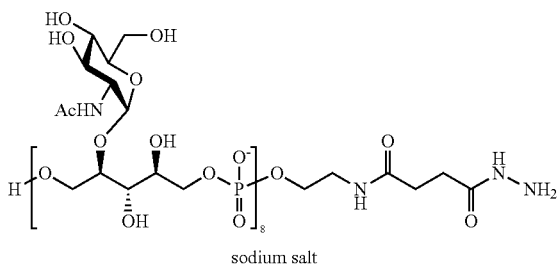
sodium salt

Step 2.1: 4-O-(2-azido-3,4,6-tri-O-benzyl-2-deoxy-α-D-glucopyranosyl)-2,3-di-O-benzyl-1-O-levu-linoyl-5-O-(4-methoxyphenyl)-D-ribitol (16)

Compound 14 (13.80 g, 15.4 mmol) was treated according to the procedure described in Step 1.9 to give target compound 16 as a colourless oil that was used without further purification in the following step.

Step 2.2: 4-O-(2-azido-3,4,6-tri-O-benzyl-2-deoxy-α-D-glucopyranosyl)-2,3-di-O-benzyl-1-O-levu-linoyl-D-ribitol (18)

Compound 16 (15.3 g, 15.4 mmol) was treated according to the procedure described in Step 1.10 to give 12.1 g (87% yield) of target compound 18 after purification by flash chromatography on silica gel (toluene/EtOAc 95/5 to 3/1).
LC-MS (method 3) m/z (ESI) 888.2 [(M+H)$^+$]; RT=8.91 min Step 2.3: 4-O-(2-azido-3,4,6-tri-O-benzyl-2-deoxy-α-D-glucopyranosyl)-5-O-{[4-O-(2-azido-3,4,6-tri-O-benzyl-2-deoxy-α-D-glucopyranosyl)-2,3-di-O-benzyl-1-O-[(2-cyanoethoxy)phosphoryl]-5-O-(4-methoxyphenyl)]-D-ribitol}-2,3-di-O-benzyl-1-O-levulinoyl-D-ribitol (20)

Compound 14 (3.8 g, 4.24 mmol) was reacted according to the procedure described in Step 1.11 with chloro-2-cyanoethyl-N,N-diisopropylphosphoramidite (1.27 mL, 5.51 mmol) and compound 18 (2.82 g, 3.18 mmol) to give 5.70 g (94% yield) of target compound 20 as a gum after purification by flash chromatography (toluene/EtOAc 95/5 to 7/3). SFC-MS (method 9) m/z 1920.7 [M+Na]$^+$; RT=9.29 min Step 2.4: 4-O-(2-azido-3,4,6-tri-O-benzyl-2-deoxy-α-D-glucopyranosyl)-5-O-{[4-O-(2-azido-3,4,6-tri-O-benzyl-2-deoxy-α-D-glucopyranosyl)-2,3-di-O-benzyl-1-O-[(2-cyanoethoxy)phosphoryl]-5-O-(4-methoxyphenyl)]-D-ribitol}-2,3-di-O-benzyl-D-ribitol (23)

Compound 20 (12.80 g, 6.74 mmol) was treated according to the procedure described in Step 1.12 to give 8.70 g (72% yield) of target compound 23 as a white foam after purification by flash chromatography on silica gel (toluene/EtOAc 95/5 to 3/2).
SFC-MS (method 9) m/z 1822.5 [M+Na]$^+$; RT=10.07 min Step 2.5: 4-O-(2-azido-3,4,6-tri-O-benzyl-2-deoxy-α-D-glucopyranosyl)-5-O-{[4-O-(2-azido-3,4,6-tri-O-benzyl-2-deoxy-α-D-glucopyranosyl)-2,3-di-O-benzyl-1-O-[(2-cyanoethoxy)phosphoryl]]-D-ribitol}-2,3-di-O-benzyl-1-O-levulinoyl-D-ribitol (24)

Compound 20 (9.60 g, 5.06 mmol) was treated according to the procedure described in Step 1.10 to give 6.23 g (69% yield) of target compound 24 after purification by flash chromatography on silica gel (toluene/EtOAc 95/5 to 7/3).
SFC-MS (method 9) m/z 1814.5 [M+Na]$^+$; RT=9.74 min

Step 2.6: 4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-2,3-di-O-benzyl-1-O-[(2-cyanoethoxy)phosphoryl]-5-O-(4-methoxyphenyl)-D-ribitol}-2,3-di-O-benzyl-1-O-[(2-cyanoethoxy)phosphoryl]-D-ribitol]-2,3-di-O-benzyl-1-O-[(2-cyanoethoxy)phosphoryl]-D-ribitol}-2,3-di-O-benzyl-1-O-levulinoyl-D-ribitol (26)

Compound 23 (0.99 g, 0.55 mmol) was reacted according to the procedure described in Step 1.11 with chloro-2-cyanoethyl-N,N-diisopropylphosphoramidite (164 μL, 0.71 mmol) and compound 24 (0.73 g, 0.41 mmol) to give 1.17 g (77% yield) of target compound 26 as a white foam after purification by flash chromatography (toluene/EtOAc 9/1 to 1/1).

SFC-MS (method 9) m/z 1872.3 [M+2NH$_4$]$^{2+}$; RT=11.68 min

Step 2.7: 4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-2,3-di-O-benzyl-1-O-[(2-cyanoethoxy)phosphoryl]-5-O-(4-methoxyphenyl)-D-ribitol}-2,3-di-O-benzyl-1-O-[(2-cyanoethoxy)phosphoryl]-D-ribitol]-2,3-di-1-benzyl-1-O-[(2-cyanoethoxy)phosphoryl]-D-ribitol}-2,3-di-O-benzyl-D-ribitol (29)

Compound 26 (4.51 g, 1.21 mmol) was treated according to the procedure described in Step 1.12 to give 3.58 g (82% yield) of target compound 29 as a white foam after purification by flash chromatography on silica gel (toluene/EtOAC 7/3 to 2/3) and size exclusion chromatography on Sephadex® LH-20 (DCM/MeOH 1/1).

LC-MS (method 5) m/z 1823.1 (average mass) [M+2NH$_4$]$^{2+}$; RT=21.91 min

Step 2.8: 4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-2,3-di-O-benzyl-1-O-[(2-cyanoethoxy) phosphoryl]-D-ribitol}-2,3-di-O-benzyl-1-O-[(2-cyanoethoxy)phosphoryl]-D-ribitol]-2,3-di-O-benzyl-1-O-[(2-cyanoethoxy)phosphoryl]-D-ribitol}-2,3-di-O-benzyl-1-O-levulinoyl-D-ribitol (30)

Compound 26 (3.20 g, 0.86 mmol) was treated according to the procedure described in Step 1.10 to give 2.13 g (68% yield) of target compound 30 as a white foam after purification by flash chromatography on silica gel (toluene/EtOAc 85/15 to 3/1) and size exclusion chromatography on Sephadex® LH-20 (DCM/MeOH 1/1).

LC-MS (method 5) m/z (ESI) 1870.1 (average mass) [(M+2HCO$_2$H+Na)$^{2+}$]; RT=20.72 min

Step 2.9: 4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-2,3-di-O-benzyl-1-O-[(2-cyanoethoxy)phosphoryl]-5-O-(4-methoxyphenyl)-D-ribitol}-2,3-di-O-benzyl-1-O-[(2-cyanoethoxy)phosphoryl]-D-ribitol]-2,3-di-O-benzyl-1-O-[(2-cyanoethoxy)phosphoryl]-D-ribitol}-2,3-di-O-benzyl-1-O-[(2-cyanoethoxy) phosphoryl]-D-ribitol]-2,3-di-O-benzyl-1-O-[(2-cyanoethoxy) phosphoryl]-D-ribitol}-2,3-di-O-benzyl-1-O-[(2-cyanoethoxy)phosphoryl]-D-ribitol]-2,3-di-O-benzyl-1-O-[(2-cyanoethoxy)phosphoryl]-D-ribitol}-2,3-di-O-benzyl-1-O-levulinoyl-D-ribitol (32)

Compound 29 (1.39 g, 0.38 μmol) was reacted according to the procedure described in Step 1.11 with chloro-2-cyanoethyl-N,N-diisopropylphosphoramidite (115 μL, 0.50 mmol) and compound 30 (1.05 g, 0.29 mmol) to give 1.01 g (47% yield) of target compound 32 as a white foam after purification by size exclusion chromatography on Sephadex® LH-20 (DCM/MeOH 1/1) and flash chromatography (toluene/EtOAc 9/1 to 1/1).

LC-HRMS (method 6): $C_{401}H_{434}N_{31}O_{89}P_7$ m/z calcd for [M+3H]$^{3+}$ 2443.63, found 2443.56; RT=9.30 min

Step 2.10: 4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-2,3-di-O-benzyl-1-O-[(2-cyanoethoxy)phosphoryl]-5-O-(4-methoxyphenyl)-D-ribitol}-2,3-di-O-benzyl-1-O-[(2-cyanoethoxy)phosphoryl]-D-ribitol}-2,3-di-O-benzyl-1-O-[(2-cyanoethoxy)phosphoryl]-D-ribitol}-2,3-di-O-benzyl-1-O-[(2-cyanoethoxy) phosphoryl]-D-ribitol]-2,3-di-O-benzyl-1-O-[(2-cyanoethoxy) phosphoryl]-D-ribitol}-2,3-di-O-benzyl-1-O-[(2-cyanoethoxy)phosphoryl]-D-ribitol]-2,3-di-1-benzyl-1-O-[(2-cyanoethoxy)phosphoryl]-D-ribitol}-2,3-di-1-benzyl-D-ribitol (34)

Compound 32 (1.10 g, 0.15 mmol) was treated according to the procedure described in Step 1.12 to give 0.80 g (92% yield) of target compound 34 as a white foam after purification by flash chromatography on silica gel (toluene/EtOAc/EtOH 7/3/0 to 7/3/0.3) and size exclusion chromatography on Sephadex® LH-20 (DCM/MeOH 3/2).

LC-HRMS (method 6): $C_{396}H_{428}N_{31}O_{87}P_7$ m/z calcd for [M+2H]$^{2+}$ 3615.92, found 3615.83; RT=9.27 min Step 2.11: 4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-2,3-di-O-benzyl-1-O-[(2-cyanoethoxy)phosphoryl]-5-O-(4-methoxyphenyl)-D-ribitol}-2,3-di-O-benzyl-1-O-[(2-cyanoethoxy)phosphoryl]-D-ribitol]-2,3-di-1-benzyl-1-O-[(2-cyanoethoxy)phosphoryl]-D-ribitol}-2,3-di-O-benzyl-1-O-[(2-cyanoethoxy) phosphoryl]-D-ribitol]-2,3-di-O-benzyl-1-O-[(2-cyanoethoxy) phosphoryl]-D-ribitol}-2,3-di-1-benzyl-1-O-[(2-cyanoethoxy)phosphoryl]-D-ribitol]-2,3-di-1-benzyl-1-O-[(2-cyanoethoxy)phosphoryl]-D-ribitol}-2,3-di-O-benzyl-1-O-[(2-{[(benzyloxy)carbonyl]amino}ethoxy)(2-cyanoethoxy)phosphoryl]-D-ribitol (36)

Benzyl N-(2-hydroxyethyl) carbamate (70 mg, 0.36 mmol) was reacted according to the procedure described in Step 1.11 with chloro-2-cyanoethyl-N,N-diisopropylphosphoramidite (71 µL, 0.30 mmol) and compound 34 (370 mg, 51.2 µmol) to give 209 mg (54% yield) of target compound 36 as a white foam after purification by flash chromatography (toluene/acetone 1/0 to 0/1).
Rf=0.53 on silica gel, toluene/acetone 3/2

Step 2.12: 4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-2,3-di-O-benzyl-1-O-[(2-cyanoethoxy)phosphoryl]-D-ribitol}-2,3-di-O-benzyl-1-O-[(2-cyanoethoxy)phosphoryl]-D-ribitol]-2,3-di-O-benzyl-1-O-[(2-cyanoethoxy)phosphoryl]-D-ribitol}-2,3-di-O-benzyl-1-O-[(2-cyanoethoxy)phosphoryl]-D-ribitol]-2,3-di-O-benzyl-1-O-[(2-cyanoethoxy)phosphoryl]-D-ribitol}-2,3-di-O-benzyl-1-O-[(2-cyanoethoxy)phosphoryl]-D-ribitol]-2,3-di-O-benzyl-1-O-[(2-cyanoethoxy)phosphoryl]-D-ribitol}-2,3-di-O-benzyl-1-O-[(2-{[(benzyloxy)carbonyl]amino}ethoxy)(2-cyanoethoxy)phosphoryl]-D-ribitol (38)

Compound 36 (122 mg, 16 µmol) was treated according to the procedure described in Step 1.10 to give 76 mg (63% yield) of target compound 38 as a white foam after purification by flash chromatography on silica gel (toluene/acetone 9/1 to 3/2).
LC-HRMS (method 6): $C_{402}H_{437}N_{33}O_{91}P_8$ m/z calcd for $[M+2H]^{2+}$ 3717.94, found 3717.99; RT=9.12 min Step 2.13: 4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-5-O-[4-O-(2-azido-3,4,6-tri-O-benzyl-2-deoxy-α-D-glucopyranosyl)-5-O-{4-O-(2-azido-3,4,6-tri-O-benzyl-2-deoxy-α-D-glucopyranosyl)-2,3-di-O-benzyl-1-O-[ammonium phosphinato]-D-ribitol}-2,3-di-O-benzyl-1-O-[ammonium phosphinato]-D-ribitol]-2,3-di-O-benzyl-1-O-[ammonium phosphinato]-D-ribitol}-2,3-di-O-benzyl-1-O-[ammonium phosphinato]-D-ribitol]-2,3-di-O-benzyl-1-O-[ammonium phosphinato]-D-ribitol}-2,3-di-O-benzyl-1-O-[ammonium phosphinato]-D-ribitol]-2,3-di-O-benzyl-1-O-[ammonium phosphinato]-D-ribitol}-2,3-di-O-benzyl-1-O-[(2-{[(benzyloxy)carbonyl]amino}ethoxy)(ammonium phosphinato)]-D-ribitol (40)

Compound 38 (318 mg, 42.8 µmol) was treated according to the procedure described in Step 1.21 to give 295 mg (96% yield) of target compound 40 as a white gum after purification by size exclusion chromatography on Sephadex® LH-20 (DCM/MeOH 1/4).
LC-HRMS (method 6): $C_{378}H_{405}N_{25}O_{91}P_8$ m/z calcd for $[M+6H]^{2-}$ 3503.82, found 3503.59; RT=9.23 min Step 2.14: 4-O-(2-acetamido-3,4,6-tri-O-benzyl-2-deoxy-α-D-glucopyranosyl)-5-O-{4-O-(2-acetamido-3,4,6-tri-O-benzyl-2-deoxy-α-D-glucopyranosyl)-5-O-[4-O-(2-acetamido-3,4,6-tri-O-benzyl-2-deoxy-α-D-glucopyranosyl)-5-O-{4-O-(2-acetamido-3,4,6-tri-O-benzyl-2-deoxy-α-D-glucopyranosyl)-5-O-[4-O-(2-acetamido-3,4,6-tri-O-benzyl-2-deoxy-α-D-glucopyranosyl)-5-O-{4-O-(2-acetamido-3,4,6-tri-O-benzyl-2-deoxy-α-D-glucopyranosyl)-5-O-[4-O-(2-acetamido-3,4,6-tri-O-benzyl-2-deoxy-α-D-glucopyranosyl)-5-O-{4-O-(2-acetamido-3,4,6-tri-O-benzyl-2-deoxy-α-D-glucopyranosyl)-2,3-di-O-benzyl-1-O-[sodium phosphinato]-D-ribitol}-2,3-di-O-benzyl-1-O-[sodium phosphinato]-D-ribitol]-2,3-di-O-benzyl-1-O-[sodium phosphinato]-D-ribitol}-2,3-di-O-benzyl-1-O-[sodium phosphinato]-D-ribitol]-2,3-di-O-benzyl-1-O-[sodium phosphinato]-D-ribitol}-2,3-di-O-benzyl-1-O-[sodium phosphinato]-D-ribitol]-2,3-di-O-benzyl-1-O-[sodium phosphinato]-D-ribitol}-2,3-di-O-benzyl-1-O-[(2-{[(benzyloxy)carbonyl]amino}ethoxy)(sodium phosphinato)]-D-ribitol (42)

Compound 40 (362 mg, 50.7 µmol) was treated according to the procedure described in Step 1.22 to give 347 mg (96% yield) of target compound 42 as a gum after purification by size exclusion chromatography on Sephadex® LH-20 (DCM/MeOH 1/4).
LC-HRMS (method 6): $C_{394}H_{437}N_9O_{99}P_8$ m/z calcd for $[M+5H]^{3-}$ 2378.26, found 2378.10; RT=8.27 min Step 2.15: 4-O-(2-acetamido-2-deoxy-α-D-glucopyranosyl)-5-O-{4-O-(2-acetamido-2-deoxy-α-D-glucopyranosyl)-5-O-[4-O-(2-acetamido-2-deoxy-α-D-glucopyranosyl)-5-O-{4-O-(2-acetamido-2-deoxy-α-D-glucopyranosyl)-5-O-[4-O-(2-acetamido-α-D-glucopyranosyl)-5-O-{4-O-(2-acetamido-2-deoxy-α-D-glucopyranosyl)-5-O-[4-O-(2-acetamido-2-deoxy-α-D-glucopyranosyl)-5-O-{4-O-(2-acetamido-2-deoxy-α-D-glucopyranosyl)-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[(2-aminoethoxy)(sodium phosphinato)]-D-ribitol (44)

Compound 42 (171 mg, 22.1 μmol) was treated according to the procedure described in Step 1.23 to give target compound 44 quantitatively as a gum after purification by size exclusion chromatography on Sephadex® G25 (0.2 M NaCl) and then Sephadex® G25 (water).

ESI HRMS: $C_{106}H_{191}N_9O_{97}P_8{}^{8-}$ m/z calcd for [M+2H+Na]$^{5-}$ 683.17, found 683.17.

Step 2.16: 4-O-(2-acetamido-2-deoxy-α-D-glucopyranosyl)-5-O-{4-O-(2-acetamido-2-deoxy-α-D-glucopyranosyl)-5-O-[4-O-(2-acetamido-2-deoxy-α-D-glucopyranosyl)-5-O-{4-O-(2-acetamido-2-deoxy-α-D-glucopyranosyl)-5-O-[4-O-(2-acetamido-2-deoxy-α-D-glucopyranosyl)-5-O-{4-O-(2-acetamido-2-deoxy-α-D-glucopyranosyl)-5-O-[4-O-(2-acetamido-2-deoxy-α-D-glucopyranosyl)-5-O-{4-O-(2-acetamido-2-deoxy-α-D-glucopyranosyl)-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[(2-[(4-hydrazino-4-oxobutanoyl)amino]ethoxy)(sodium phosphinato)]-D-ribitol (2)

Compound 44 (75 mg, 21 μmol) in solution in water (2.1 mL) is added dropwise under vigorous stirring to a solution containing disuccinimidyl succinate (130 mg, 0.42 mmol) and N,N-diisopropylethylamine (80 μL, 0.46 mmol) in DMSO (11.0 mL) to give intermediate 46. After stirring for 0.5 h at rt, a first portion of hydrazine hydrate (0.74 mL, 8.4 mmol) was added to the reaction mixture, followed by 3 other portions (0.57 mmol, 0.23 mmol) after 1 h, 1.5 h and 2.5 h. Purification by size exclusion chromatography on Sephadex® G25 (0.2 M NaCl) then on Sephadex® G25 (water), by preparative ionic Dionex chromatography followed by size exclusion chromatography on Sephadex® G25 (water) afforded 21 mg (27%) of target compound 2 as white foam after lyophilization.

ESI HRMS: $C_{110}H_{197}N_{11}O_{99}P_8$ m/z calcd for [M+2H]$^{6-}$ 584.48, found 584.48.

CE (method 8b): MT=7.38 min $^1$H (600 MHz, D$_2$O) δ=5.12 (8H, m), 4.20-4.01 (30H, m), 4.13 (7H, m), 4.09 (9H, m), 4.02-3.93 (16H, m), 4.00 (8H, m), 3.98 (3H, m), 3.96 (1H, m), 3.96-3.85 (16H, m), 3.89 (8H, m), 3.56 (8H, m), 3.49 (2H, m), 2.63 (2H, m), 2.55 (2H, m), 2.13 (24H, s).

Example 3—Synthesis of the β(1,3) Nonamer 3-O-(2-acetamido-2-deoxy-(3-D-glucopyranosyl)-5-O-{3-O-(2-acetamido-2-deoxy-β-D-glucopyranosyl)-5-O-[3-O-(2-acetamido-2-deoxy-β-D-glucopyranosyl)-5-O-{3-O-(2-acetamido-2-deoxy-β-D-glucopyranosyl)-5-O-[3-O-(2-acetamido-2-deoxy-β-D-glucopyranosyl)-5-O-{3-O-(2-acetamido-2-deoxy-β-D-glucopyranosyl)-5-O-[3-O-(2-acetamido-2-deoxy-β-D-glucopyranosyl)-5-O-{3-O-(2-acetamido-2-deoxy-[3-D-glucopyranosyl)-5-O-f{3-O-(2-acetamido-2-deoxy-β-D-glucopyranosyl)-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol}-1-O-[sodium phosphinato]-D-ribitol]-1-O-[sodium phosphinato]-D-ribitol}-1-O-[(2-[(4-hydrazino-4-oxobutanoyl)amino]ethoxy)(sodium phosphinato)]-D-ribitol (3)

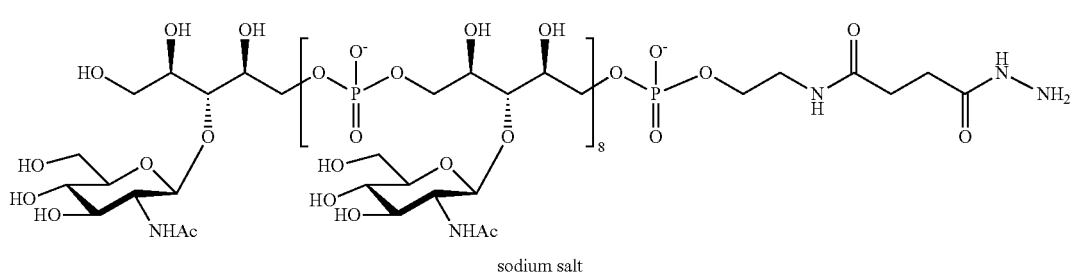

3 sodium salt

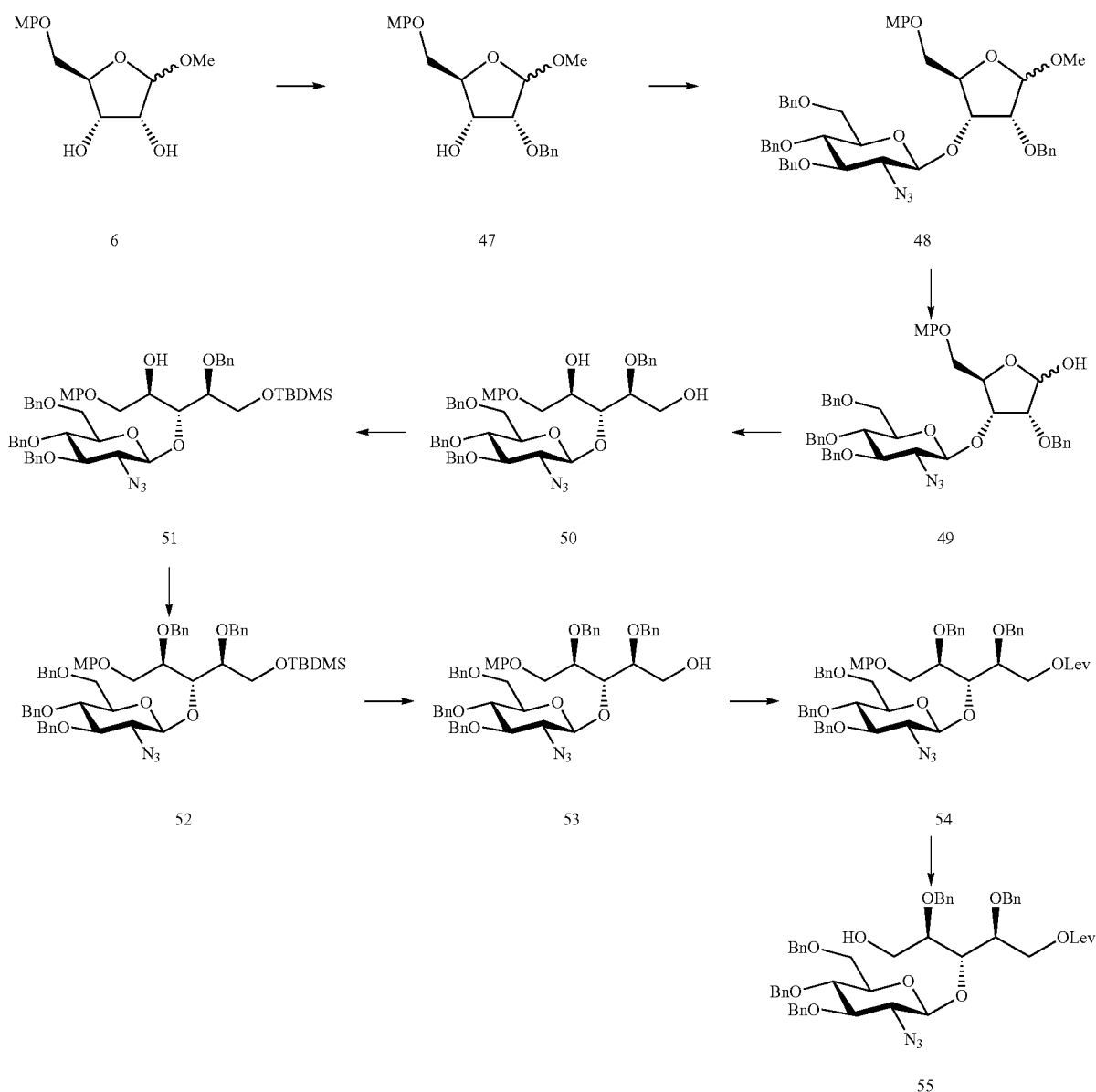

Step 3.1: methyl 2-O-benzyl 5-O-(4-methoxyphenyl)-D-ribofuranoside (47)

To a solution of 6 (45.3 g, 168 mmol) in DCM (1.68 L) were successively added tetra-n-butylammonium bromide (10.8 g, 33.5 mmol), benzyl bromide (21.9 mL, 184 mmol) and 10% aqueous sodium hydroxide (168 mL). The reaction mixture was stirred at rt for 20 h, diluted with DCM and water. After separation of the two layers, the organic layer was dried over sodium sulfate, filtered and concentrated in vacuo. The residue obtained was purified by flash chromatography on silica gel (toluene/EtOAc 1/0 to 0/1) to afford 20.25 g (34% yield) of target compound 47.

LC-MS (method 1) m/z 383 [M+Na]$^+$; RT=8.2 min

Step 3.2: methyl 3-O-(2-azido-3,4,6-tri-O-benzyl-2-deoxy-β-D-glucopyranosyl)-2-O-benzyl-5-O-(4-methoxyphenyl)-D-ribofuranoside (48)

A mixture of ethyl 2-azido-3,4,6-tri-O-benzyl-2-deoxy-1-thio-β-D-glucopyranoside (11) (7.6 g, 13.5 mmol) [Y. Du, J. Lin, R. J. Linhardt, *Journal of Carbohydrate Chemistry*, 1997, 16(9), 1327-1344], methyl 2-O-benzyl-5-O-(4-methoxyphenyl)-D-ribofuranoside 47 (4.04 g, 11.2 mmol) in acetonitrile/propionitrile/DCM 2/1/1 (1.12 L) and molecular sieve 4 Å powder (11.2 g) was stirred under argon for 1 h at rt. The mixture was then cooled to −70° C. and N-iodosuccinimide (4.5 g, 20.2 mmol) and a 1M solution of triflic acid in DCM (3.9 mL, 3.9 mmol) were successively added. After stirring for 10 min at −70° C., triethylamine (0.5 mL) was added dropwise and the reaction mixture was filtered on Celite® and diluted with DCM. The organic solution was washed with a 1M aqueous solution of sodium thiosulfate and brine, dried over sodium sulfate, filtered and concentrated in vacuo. The residue obtained was purified by flash chromatography on silica gel (toluene/EtOAc 1/0 to 9/1) to afford 9.33 g (84% yield) of target compound 48.

LC-MS (method 12a) m/z 835.2 [M+NH$_4$]$^+$; RT=2.08 min

Step 3.3: 3-O-(2-azido-3,4,6-tri-O-benzyl-2-deoxy-β-D-glucopyranosyl)-2-O-benzyl-5-O-(4-methoxyphenyl)-D-ribofuranose (49)

Hydrochloric acid 3M (47 mL) was added to a solution of compound 48 (15.3 g, 18.7 mmol) in 1,4-dioxane (140 mL). The mixture was stirred at reflux for 7 h and cooled to rt. The reaction mixture was poured slowly into a solution of sodium hydrogen carbonate (20 g) in water (500 mL) at 0° C. After extraction with DCM, the organic layer was dried over sodium sulfate, filtered and concentrated in vacuo. The residue obtained was purified by flash chromatography on silica gel (toluene/EtOAc 1/0 to 3/2) to give 10.9 g (73% yield) of target compound 49.

LC-MS (method 1) m/z 826.4 [(M+Na)$^+$]; RT=11.64 min

Step 3.4: 3-O-(2-azido-3,4,6-tri-O-benzyl-2-deoxy-β-D-glucopyranosyl)-2-O-benzyl-5-O-(4-methoxyphenyl)-D-ribitol (50)

Sodium borohydride (1.7 g, 45.3 mmol) was added portionwise to a solution of compound 49 (20.2 g, 25.2 mmol) in methanol (250 mL) at 0° C. The reaction mixture was stirred at rt for 3.5 h. The mixture was diluted with DCM and poured slowly into water. The layers were separated and the organic layer was dried over sodium sulfate, filtered and concentrated in vacuo a give target compound 50 that was used without further purification in the following step.

Step 3.5: 3-O-(2-azido-3,4,6-tri-O-benzyl-2-deoxy-β-D-glucopyranosyl)-2-O-benzyl-1-O-tert-butyldimethylsilyl-5-O-(4-methoxyphenyl)-D-ribitol (51)

To a solution of compound 50 (25.2 mmol) in DCM (330 mL) at 0° C. under argon were successively added DMAP (462 mg, 3.78 mmol), triethylamine (17.7 mL, 126 mmol) and tert-butyldimethylsilyl chloride (11.4 g, 75.6 mmol). The solution was stirred at rt overnight, diluted with DCM and washed with an aqueous solution of potassium hydrogenosulfate 10%, an aqueous sodium hydrogenocarbonate 2% and brine. The organic layer was dried over sodium sulfate, filtered and concentrated in vacuo to give target compound 51 that was used without further purification in the following step.

Step 3.6: 3-O-(2-azido-3,4,6-tri-O-benzyl-2-deoxy-β-D-glucopyranosyl)-2,4-di-O-benzyl-1-O-tert-butyldimethylsilyl-5-O-(4-methoxyphenyl)-D-ribitol (52)

To a solution of compound 51 (25.2 mmol) in anhydrous DMF (240 mL) at 0° C. under argon were added successively and portionwise sodium hydride (60% suspension in oil, 1.5 g, 37.8 mmol) and benzyl bromide (7.5 mL, 63.0 mmol). The mixture was stirred at rt overnight and cooled to 0° C. before methanol was added. The mixture was concentrated in vacuo, diluted with DCM and washed with water twice. The organic layer was dried over sodium sulfate, filtered and concentrated in vacuo to give target compound 52 that was used without further purification in the following step.

Step 3.7: 3-O-(2-azido-3,4,6-tri-O-benzyl-2-deoxy-β-D-glucopyranosyl)-2,4-di-O-benzyl-5-O-(4-methoxyphenyl)-D-ribitol (53)

To a solution of compound 52 (25.2 mmol) in anhydrous THF (1 L) at 0° C. under argon were added successively acetic acid (43 mL, 0.75 mol) and TBAF 1M in THF (756 mL, 0.75 mol). The mixture was stirred at rt overnight and cooled to 0° C. before acetic acid (7.4 mL, 0.126 mol) and TBAF 1M in THF (126 mL, 0.126 mol) were added. The mixture was stirred for a further 5 h at rt and concentrated in vacuo. The residue was dissolved in DCM and washed with water. The organic layer was dried over sodium sulfate, filtered and concentrated in vacuo. The residue obtained was purified by flash chromatography on silica gel (toluene/EtOAc 1/0 to 4/1) to give 21.3 g (94% yield) of target compound 53.

SFC-MS (method 10) m/z 918.4 [(M+Na)$^+$]; RT=4.84 and 4.94 min

Step 3.8: 3-O-(2-azido-3,4,6-tri-O-benzyl-2-deoxy-β-D-glucopyranosyl)-2,4-di-O-benzyl-1-O-levulinoyl-5-O-(4-methoxyphenyl)-D-ribitol (54)

Compound 53 (17.9 g, 20.0 mmol) was treated according to the procedure described in Step 1.9 to give target compound 54 as a colourless oil that was used without further purification in the following step.

Step 3.9: 3-O-(2-azido-3,4,6-tri-O-benzyl-2-deoxy-β-D-glucopyranosyl)-2,4-di-O-benzyl-1-O-levulinoyl-D-ribitol (55)

Compound 54 (20.0 mmol) was treated according to the procedure described in Step 1.10 to give 12.6 g (71% yield over 2 steps) of target compound 55 after purification by flash chromatography on silica gel (toluene/EtOAc 1/0 to 7/3).

LC-MS (method 4) m/z 910.4 [(M+Na)$^+$]; RT=3.46 min

Scheme 7

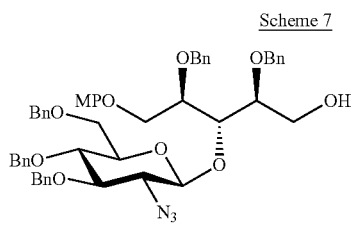

53

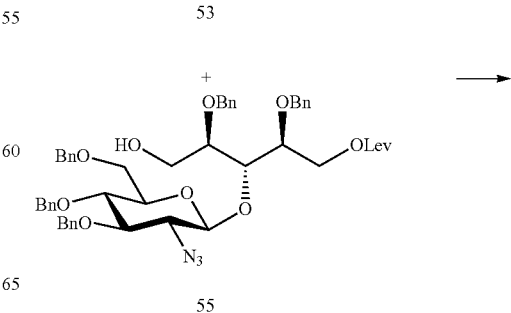

55

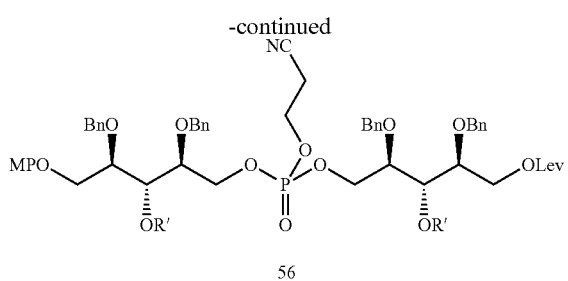

56

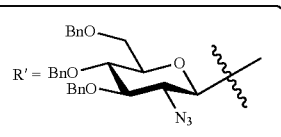

Step 3.10: 3-O-(2-azido-3,4,6-tri-O-benzyl-2-deoxy-β-D-glucopyranosyl)-5-O-{[3-O-(2-azido-3,4,6-tri-O-benzyl-2-deoxy-β-D-glucopyranosyl)-2,4-di-O-benzyl-1-O-[(2-cyanoethoxy)phosphoryl]-5-O-(4-methoxyphenyl)]-D-ribitol}-2,4-di-O-benzyl-1-O-levulinoyl-D-ribitol (56)

Compound 53 (2.83 g, 3.15 mmol) was reacted according to the procedure described in Step 1.11 with chloro-2-cyanoethyl-N,N-diisopropylphosphoramidite (0.94 mL, 4.10 mmol) and compound 55 (2.0 g, 2.25 mmol) to give 3.49 g (82% yield) of target compound 56 as a white foam after purification by flash chromatography (toluene/EtOAc 1/0 to 4/1).

LC-MS (method 5) m/z 1915.5 [M+NH$_4$]$^+$; RT=14.61 min

Scheme 8

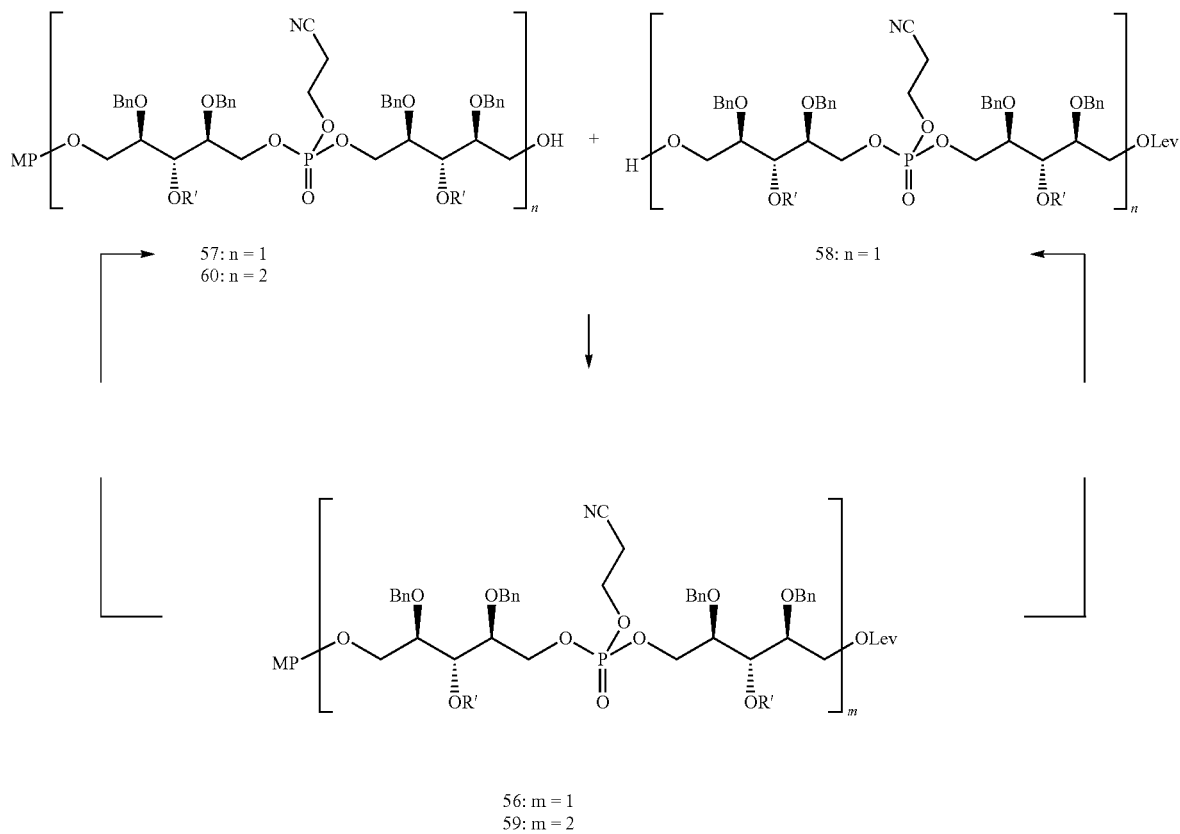

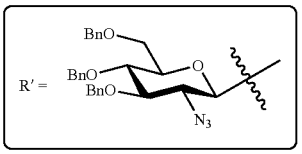

Step 3.11: 3-O-(2-azido-3,4,6-tri-O-benzyl-2-deoxy-
β-D-glucopyranosyl)-5-O-{[3-O-(2-azido-3,4,6-tri-
O-benzyl-2-deoxy-β-D-glucopyranosyl)-2,4-di-O-
benzyl-1-O-[(2-cyanoethoxy)phosphoryl]-5-O-(4-
methoxyphenyl)]-D-ribitol}-2,4-di-O-benzyl-D-
ribitol (57)

Compound 56 (7.73 g, 4.0 mmol) was treated according to the procedure described in Step 1.12 to give 6.29 g (86% yield) of target compound 57 after purification by flash chromatography on silica gel (toluene/EtOAc 1/0 to 4/1).
LC-MS (method 11) m/z 1822.5 [(M+Na)$^+$]; RT=29.16 min Step 3.12: 3-O-(2-azido-3,4,6-tri-O-benzyl-2-deoxy-
β-D-glucopyranosyl)-5-O-{[3-O-(2-azido-3,4,6-tri-
O-benzyl-2-deoxy-β-D-glucopyranosyl)-2,4-di-O-
benzyl-1-O-[(2-cyanoethoxy)phosphoryl]]-D-
ribitol}-2,4-di-O-benzyl-1-O-levulinoyl-D-ribitol
(58)

Compound 56 (0.95 g, 0.50 mmol) was treated according to the procedure described in Step 1.10 to give 0.56 g (62% yield) of target compound 58 after purification by flash chromatography on silica gel (toluene/acetone 9/1 to 3/2).
SFC-MS (method 9) m/z 1814.5 [M+Na]$^+$; RT=9.76 min Step 3.13: 3-O-(2-azido-3,4,6-tri-O-benzyl-2-deoxy-
5-D-glucopyranosyl)-5-O-{3-O-(2-azido-3,4,6-tri-O-
benzyl-2-deoxy-β-D-glucopyranosyl)-5-O-[3-O-(2-
azido-3,4,6-tri-O-benzyl-2-deoxy-β-D-
glucopyranosyl)-5-O-{3-O-(2-azido-3,4,6-tri-O-
benzyl-2-deoxy-β-D-glucopyranosyl)-2,4-di-O-
benzyl-1-O-[(2-cyanoethoxy)phosphoryl]-5-O-(4-
methoxyphenyl)-D-ribitol}-2,4-di-O-benzyl-1-O-[(2-
cyanoethoxy)phosphoryl]-D-ribitol]-2,4-di-O-
benzyl-1-O-[(2-cyanoethoxy)phosphoryl]-D-ribitol}-
2,4-di-O-benzyl-1-O-levulinoyl-D-ribitol (59)

Compound 57 (2.33 g, 1.29 mmol) and compound 58 (1.93 g, 1.08 mmol) were coupled according to the procedure described in Step 1.11 to give 3.15 g (79% yield) of target compound 59 after purification by flash chromatography on silica gel (toluene/EtOAc 1/0 to 1/3).

LC-HRMS (method 7): $C_{205}H_{222}N_{15}O_{45}P_3$ m/z calcd for [M+H]$^+$ 3709.49, found 3709.48; RT=8.22 min Step 3.14: 3-O-(2-azido-3,4,6-tri-O-benzyl-2-deoxy-
β-D-glucopyranosyl)-5-O-{3-O-(2-azido-3,4,6-tri-O-
benzyl-2-deoxy-β-D-glucopyranosyl)-5-O-[3-O-(2-
azido-3,4,6-tri-O-benzyl-2-deoxy-β-D-
glucopyranosyl)-5-O-{3-O-(2-azido-3,4,6-tri-O-
benzyl-2-deoxy-β-D-glucopyranosyl)-2,4-di-O-
benzyl-1-O-[(2-cyanoethoxy)phosphoryl]-5-O-(4-
methoxyphenyl)-D-ribitol}-2,4-di-O-benzyl-1-O-[(2-
cyanoethoxy)phosphoryl]-D-ribitol]-2,4-di-O-
benzyl-1-O-[(2-cyanoethoxy) phosphoryl]-D-
ribitol}-2,4-di-O-benzyl-D-ribitol (60)

Compound 59 (12.39 g, 3.34 mmol) was treated according to the procedure described in Step 1.12 to give 9.65 g (82% yield) of target compound 60 after purification by flash chromatography on silica gel (toluene/EtOAc 1/0 to 3/7) and size exclusion chromatography on Sephadex® LH-20 (DCM/MeOH 1/1).

LC-HRMS (method 7): $C_{200}H_{216}N_{15}O_{43}P_3$ m/z calcd for [M+2H]$^{2+}$ 1806.23, found 1806.15; RT=8.19 min Scheme 9

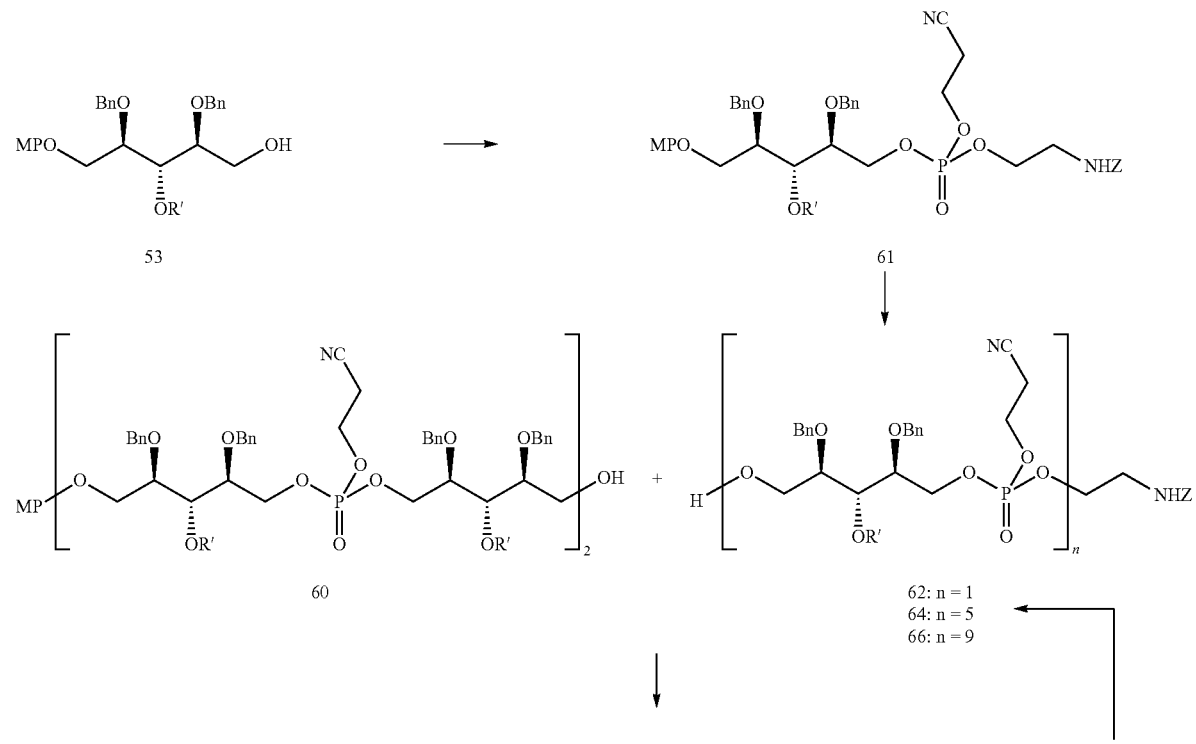

62: n = 1
64: n = 5
66: n = 9

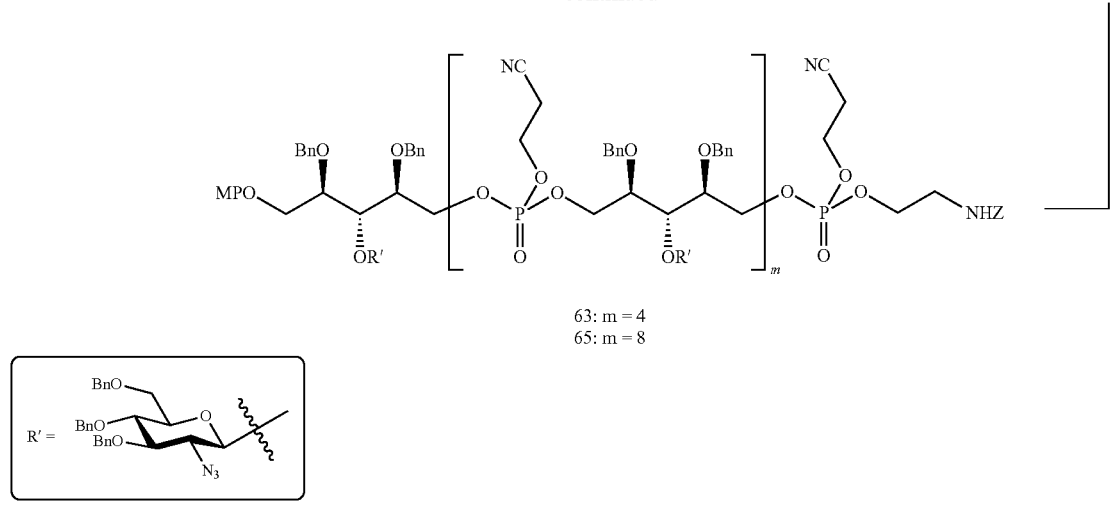

63: m = 4
65: m = 8

Step 3.15. 3-O-(2-azido-3,4,6-tri-O-benzyl-2-deoxy-β-D-glucopyranosyl)-2,4-di-O-benzyl-1-O-[(2-{[(benzyloxy)carbonyl]amino}ethoxy)(2-cyanoethoxy)phosphoryl]-5-O-(4-methoxyphenyl)-D-ribitol (61)

Compound 53 (3.4 g, 3.79 mmol) was reacted according to the procedure described in Step 1.11 with chloro-2-cyanoethyl-N,N-diisopropylphosphoramidite (2.1 mL, 9.49 mmol) and benzyl N-(2-hydroxyethyl) carbamate (3.7 g, 18.95 mmol) to give 2.97 g (65% yield) of target compound 61 as a white foam after purification by flash chromatography on silica gel (toluene/EtOAc 1/0 to 4/1).

LC-MS (method 1) m/z 1228.2 [(M+Na)$^+$]; RT=12.39 min

Step 3.16: 3-O-(2-azido-3,4,6-tri-O-benzyl-2-deoxy-β-D-glucopyranosyl)-2,4-di-O-benzyl-1-O-[(2-{[(benzyloxy)carbonyl]amino}ethoxy)(2-cyanoethoxy)phosphoryl]-D-ribitol (62)

Compound 61 (3.56 g, 2.95 mmol) was treated according to the procedure described in Step 1.10 to give 3.10 g (85% yield) of target compound 62 after purification by flash chromatography on silica gel (toluene/acetone 4/1 to 7/3).

LC-MS (method 1) m/z 1122.2 [(M+Na)$^+$]; RT=11.59 min

Step 3.17: 3-O-(2-azido-3,4,6-tri-O-benzyl-2-deoxy-β-D-glucopyranosyl)-5-O-{3-O-(2-azido-3,4,6-tri-O-benzyl-2-deoxy-β-D-glucopyranosyl)-5-O-[3-O-(2-azido-3,4,6-tri-O-benzyl-2-deoxy-β-D-glucopyranosyl)-5-O-{3-O-(2-azido-3,4,6-tri-O-benzyl-2-deoxy-β-D-glucopyranosyl)-5-O-{3-O-(2-azido-3,4,6-tri-O-benzyl-2-deoxy-β-D-glucopyranosyl)-2,4-di-O-benzyl-1-O-[(2-cyanoethoxy)phosphoryl]-5-O-(4-methoxyphenyl)-D-ribitol}-2,4-di-O-benzyl-1-O-[(2-cyanoethoxy)phosphoryl]-2,4-di-O-benzyl-1-O-[(2-cyanoethoxy)phosphoryl]-D-ribitol]-2,4-di-O-benzyl-1-O-[(2-cyanoethoxy)phosphoryl]-D-ribitol}-2,4-di-O-benzyl-1-O-[(2-{[(benzyloxy)carbonyl]amino}ethoxy)(2-cyanoethoxy)phosphoryl]-D-ribitol (63)

Compound 60 (1.79 g, 0.50 mmol) and compound 62 (0.60 g, 0.54 mmol) were coupled according to the procedure described in Step 1.11 to give 1.85 g (77% yield) of target compound 63 after purification by flash chromatography on silica gel (toluene/acetone 1/0 to 3/2).

LC-HRMS (method 7): $C_{262}H_{284}N_{21}O_{59}P_5$ m/z calcd for [M+2H]$^{2+}$ 2413.94, found 2413.86; RT=8.49 min

Step 3.18: 3-O-(2-azido-3,4,6-tri-O-benzyl-2-deoxy-3β-D-glucopyranosyl)-5-O-{3-O-(2-azido-3,4,6-tri-O-benzyl-2-deoxy-β-D-glucopyranosyl)-5-O-[3-O-(2-azido-3,4,6-tri-O-benzyl-2-deoxy-β-D-glucopyranosyl)-5-O-{3-O-(2-azido-3,4,6-tri-O-benzyl-2-deoxy-β-D-glucopyranosyl)-5-O-{3-O-(2-azido-3,4,6-tri-O-benzyl-2-deoxy-β-D-glucopyranosyl)-2,4-di-O-benzyl-1-O-[(2-cyanoethoxy)phosphoryl]-D-ribitol}-2,4-di-O-benzyl-1-O-[(2-cyanoethoxy)phosphoryl]-D-ribitol}-2,4-di-O-benzyl-1-O-[(2-cyanoethoxy)phosphoryl]-D-ribitol]-2,4-di-O-benzyl-1-O-[(2-cyanoethoxy)phosphoryl]-D-ribitol}-2,4-di-O-benzyl-1-O-[(2-{[(benzyloxy)carbonyl]amino} ethoxy)(2-cyanoethoxy)phosphoryl]-D-ribitol (64)

Compound 63 (568 mg, 118 µmol) was treated according to the procedure described in Step 1.10 to give 411 mg (74% yield) of target compound 64.

ESI HRMS: $C_{255}H_{278}N_{21}O_{58}P5$ m/z calcd for [M+2Na]$^{2+}$ 2382.90, found 2382.86.

SFC (method 9): RT=13.40 min

75

Step 3.19: 3-O-(2-azido-3,4,6-tri-O-benzyl-2-deoxy-β-D-glucopyranosyl)-5-O-{3-O-(2-azido-3,4,6-tri-O-benzyl-2-deoxy-β-D-glucopyranosyl)-5-O-[3-O-(2-azido-3,4,6-tri-O-benzyl-2-deoxy-β-D-glucopyranosyl)-5-O-{3-O-(2-azido-3,4,6-tri-O-benzyl-2-deoxy-β-D-glucopyranosyl)-5-O-[3-O-(2-azido-3,4,6-tri-O-benzyl-2-deoxy-β-D-glucopyranosyl)-5-O-{3-O-(2-azido-3,4,6-tri-O-benzyl-2-deoxy-β-D-glucopyranosyl)-5-O-[3-O-(2-azido-3,4,6-tri-O-benzyl-2-deoxy-β-D-glucopyranosyl)-5-O-{3-O-(2-azido-3,4,6-tri-O-benzyl-2-deoxy-β-D-glucopyranosyl)-2,4-di-O-benzyl-1-O-[(2-cyanoethoxy)phosphoryl]-5-O-(4-methoxyphenyl)-D-ribitol}-2,4-di-O-benzyl-1-O-[(2-cyanoethoxy) phosphoryl]-D-ribitol]-2,4-di-O-benzyl-1-O-[(2-cyanoethoxy) phosphoryl]-D-ribitol}-2,4-di-O-benzyl-1-O-[(2-cyanoethoxy)phosphoryl]-D-ribitol]-2,4-di-O-benzyl-1-O-[(2-cyanoethoxy)phosphoryl]-D-ribitol}-2,4-di-O-benzyl-1-O-[(2-cyanoethoxy) phosphoryl]-D-ribitol}-2,4-di-O-benzyl-1-O-[(2-cyanoethoxy)phosphoryl]-D-ribitol]-2,4-di-O-benzyl-1-O-[(2-cyanoethoxy)phosphoryl]-D-ribitol}-2,4-di-O-benzyl-1-O-[(2-{[(benzyloxy)carbonyl]amino}ethoxy)(2-cyanoethoxy)phosphoryl]-D-ribitol (65)

Compound 60 (430 mg, 119 μmol) and compound 64 (469 mg, 99 μmol) were coupled according to the procedure described in Step 1.11 to give 225 mg (27% yield) of target compound 65 after purification by flash chromatography on silica gel (toluene/acetone 9/1 to 7/3).

LC-HRMS (method 7): $C_{458}H_{496}N_{37}O_{103}P_9$ m/z calcd for $[M+2H]^{2+}$ 4223.63, found 4223.72; RT=9.27 min

76

Step 3.19: 3-O-(2-azido-3,4,6-tri-O-benzyl-2-deoxy-3β-D-glucopyranosyl)-5-O-{3-O-(2-azido-3,4,6-tri-O-benzyl-2-deoxy-β-D-glucopyranosyl)-5-O-[3-O-(2-azido-3,4,6-tri-O-benzyl-2-deoxy-β-D-glucopyranosyl)-5-O-{3-O-(2-azido-3,4,6-tri-O-benzyl-2-deoxy-β-D-glucopyranosyl)-5-O-[3-O-(2-azido-3,4,6-tri-O-benzyl-2-deoxy-3β-D-glucopyranosyl)-5-O-{3-O-(2-azido-3,4,6-tri-O-benzyl-2-deoxy-β-D-glucopyranosyl)-5-O-[3-O-(2-azido-3,4,6-tri-O-benzyl-2-deoxy-β-D-glucopyranosyl)-5-O-{3-O-(2-azido-3,4,6-tri-O-benzyl-2-deoxy-β-D-glucopyranosyl)-2,4-di-O-benzyl-1-O-[(2-cyanoethoxy)phosphoryl]-D-ribitol}-2,4-di-O-benzyl-1-O-[(2-cyanoethoxy) phosphoryl]-D-ribitol]-2,4-di-O-benzyl-1-O-[(2-cyanoethoxy) phosphoryl]-D-ribitol}-2,4-di-O-benzyl-1-O-[(2-cyanoethoxy)phosphoryl]-D-ribitol]-2,4-di-O-benzyl-1-O-[(2-cyanoethoxy)phosphoryl]-D-ribitol}-2,4-di-O-benzyl-1-O-[(2-cyanoethoxy) phosphoryl]-D-ribitol}-2,4-di-O-benzyl-1-O-[(2-cyanoethoxy) phosphoryl]-D-ribitol]-2,4-di-1-benzyl-1-O-[(2-cyanoethoxy)phosphoryl]-D-ribitol}-2,4-di-O-benzyl-1-O-[(2-{[(benzyloxy)carbonyl]amino}ethoxy)(2-cyanoethoxy)phosphoryl]-D-ribitol (66)

Compound 65 (566 mg, 67.1 μmol) was treated according to the procedure described in Step 1.10 to give 445 mg (80% yield) of target compound 66 after purification by flash chromatography on silica gel (toluene/acetone 9/1 to 3/2).

LC-HRMS (method 7): $C_{451}H_{490}N_{37}O_{102}P_9$ m/z calcd for $[M+3H]^{3+}$ 2780.75, found 2780.43; RT=9.21 min Scheme 10

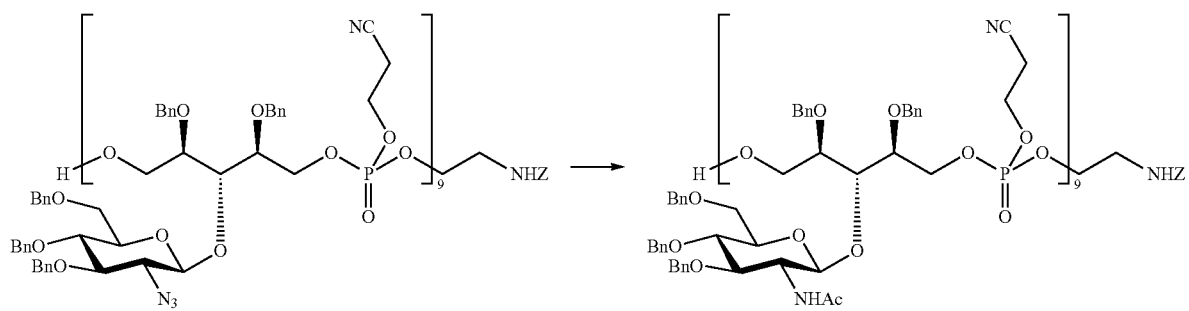

-continued

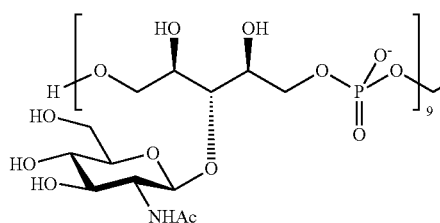

69

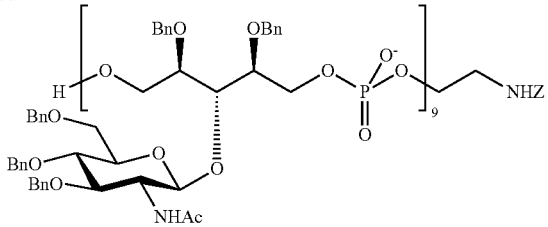

68

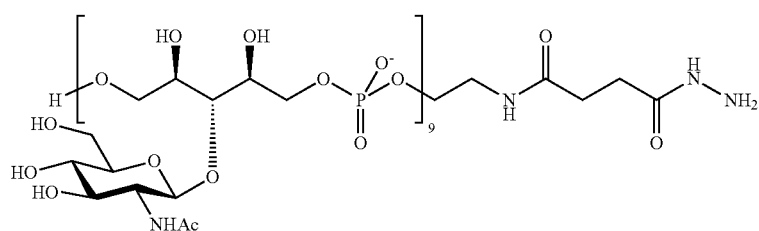

3

Step 3.20: 3-O-(2-acetamido-3,4,6-tri-O-benzyl-2-deoxy-β-D-glucopyranosyl)-5-O-{3-O-(2-acetamido-3,4,6-tri-O-benzyl-2-deoxy-β-D-glucopyranosyl)-5-O-[3-O-(2-acetamido-3,4,6-tri-O-benzyl-2-deoxy-β-D-glucopyranosyl)-5-O-{3-O-(2-acetamido-3,4,6-tri-O-benzyl-2-deoxy-β-D-glucopyranosyl)-5-O-[3-O-(2-acetamido-3,4,6-tri-O-benzyl-2-deoxy-β-D-glucopyranosyl)-5-O-{3-O-(2-acetamido-3,4,6-tri-O-benzyl-2-deoxy-β-D-glucopyranosyl)-5-O-[3-O-(2-acetamido-3,4,6-tri-O-benzyl-2-deoxy-β-D-glucopyranosyl)-5-O-{3-O-(2-acetamido-3,4,6-tri-O-benzyl-2-deoxy-β-D-glucopyranosyl)-5-O-{3-O-(2-acetamido-3,4,6-tri-O-benzyl-2-deoxy-β-D-glucopyranosyl)-2,4-di-O-benzyl-1-O-[(2-cyanoethoxy)phosphoryl]-D-ribitol}-2,4-di-O-benzyl-1-O-[(2-cyanoethoxy)phosphoryl]-D-ribitol]-2,4-di-O-benzyl-1-O-[(2-cyanoethoxy) phosphoryl]-D-ribitol}-2,4-di-O-benzyl-1-O-[(2-cyanoethoxy) phosphoryl]-D-ribitol]-2,4-di-O-benzyl-1-O-[(2-cyanoethoxy)phosphoryl]-D-ribitol}-2,4-di-O-benzyl-1-O-[(2-cyanoethoxy)phosphoryl]-D-ribitol}-2,4-di-O-benzyl-1-O-[(2-cyanoethoxy) phosphoryl]-D-ribitol]-2,4-di-O-benzyl-1-O-[(2-cyanoethoxy) phosphoryl]-D-ribitol}-2,4-di-O-benzyl-1-O-[(2-{[(benzyloxy)carbonyl]amino}ethoxy)(2-cyanoethoxy)phosphoryl]-D-ribitol (67)

Compound 66 (440 mg, 52.8 μmol) was treated according to the procedure described in Step 1.22 to give 401 mg (90% yield) of target compound 67 after purification by size exclusion chromatography on Sephadex® LH-20 (DCM/MeOH 1/1).

Step 3.21: 3-O-(2-acetamido-3,4,6-tri-O-benzyl-2-deoxy-β-D-glucopyranosyl)-5-O-{3-O-(2-acetamido-3,4,6-tri-O-benzyl-2-deoxy-β-D-glucopyranosyl)-5-O-[3-O-(2-acetamido-3,4,6-tri-O-benzyl-2-deoxy-β-D-glucopyranosyl)-5-O-{3-O-(2-acetamido-3,4,6-tri-O-benzyl-2-deoxy-β-D-glucopyranosyl)-5-O-[3-O-(2-acetamido-3,4,6-tri-O-benzyl-2-deoxy-β-D-glucopyranosyl)-5-O-{3-O-(2-acetamido-3,4,6-tri-O-benzyl-2-deoxy-β-D-glucopyranosyl)-5-O-[3-O-(2-acetamido-3,4,6-tri-O-benzyl-2-deoxy-β-D-glucopyranosyl)-5-O-{3-O-(2-acetamido-3,4,6-tri-O-benzyl-2-deoxy-β-D-glucopyranosyl)-5-O-{3-O-(2-acetamido-3,4,6-tri-O-benzyl-2-deoxy-β-D-glucopyranosyl)-2,4-di-O-benzyl-1-O-[ammonium phosphinato]-D-ribitol}-2,4-di-O-benzyl-1-O-[ammonium phosphinato]-D-ribitol]-2,4-di-O-benzyl-1-O-[ammonium phosphinato]-D-ribitol}-2,4-di-O-benzyl-1-O-[ammonium phosphinato]-D-ribitol]-2,4-di-O-benzyl-1-O-[ammonium phosphinato]-D-ribitol}-2,4-di-O-benzyl-1-O-[ammonium phosphinato]-D-ribitol]-2,4-di-O-benzyl-1-O-[ammonium phosphinato]-D-ribitol}-2,4-di-O-benzyl-1-O-[ammonium phosphinato]-D-ribitol}-2,4-di-O-benzyl-1-O-[(2-{[(benzyloxy)carbonyl]amino}ethoxy)(ammonium phosphinato)]-D-ribitol (68)

Compound 67 (401 mg, 47.3 μmol) was treated according to the procedure described in Step 1.21 to give 368 mg (97% yield) of target compound 68 after purification by size exclusion chromatography on Sephadex® LH-20 (DCM/MeOH 1/1).

LC-HRMS (method 7): $C_{442}H_{490}N_{10}O_{111}P_9$ m/z calcd for $[M+12H]^{3+}$2669.73, found 2669.69; RT=8.73 min Step 3.22: 3-O-(2-acetamido-2-deoxy-5-D-glucopyranosyl)-5-O-{3-O-(2-acetamido-2-deoxy-β-D-glucopyranosyl)-5-O-[3-O-(2-acetamido-2-deoxy-β-D-glucopyranosyl)-5-O-{3-O-(2-acetamido-2-deoxy-β-D-glucopyranosyl)-5-O-[3-O-(2-acetamido-2-deoxy-β-D-glucopyranosyl)-5-O-{3-O-(2-acetamido-2-deoxy-β-D-glucopyranosyl)-5-O-[3-O-(2-acetamido-2-deoxy-β-D-glucopyranosyl)-5-O-{3-O-(2-acetamido-2-deoxy-β-D-glucopyranosyl)-5-O-{3-O-(2-acetamido-2-deoxy-β-D-glucopyranosyl)-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[(2-aminoethoxy)(sodium phosphinato)]-D-ribitol (69)

Compound 68 (232 mg, 28.4 μmol) was treated according to the procedure described in Step 1.23 to give 54 mg (50% yield) of target compound 69 after purification by size exclusion chromatography on Sephadex® G25 (0.2 NaCl) then Sephadex® G25 (water) and by preparative ionic Dionex chromatography, followed by size exclusion chromatography on Sephadex® G25 (water).

ESI HRMS: $C_{119}H_{214}N_{10}O_{10}{}^{9}P9$ m/z calcd for $[M+2H+2Na]^{5-}$ 770.98, found 770.99.

Step 3.23: 3-O-(2-acetamido-2-deoxy-3β-D-glucopyranosyl)-5-O-{3-O-(2-acetamido-2-deoxy-β-D-glucopyranosyl)-5-O-[3-O-(2-acetamido-2-deoxy-β-D-glucopyranosyl)-5-O-{3-O-(2-acetamido-2-deoxy-β-D-glucopyranosyl)-5-O-[3-O-(2-acetamido-2-deoxy-β-D-glucopyranosyl)-5-O-{3-O-(2-acetamido-2-deoxy-β-D-glucopyranosyl)-5-O-[3-O-(2-acetamido-2-deoxy-β-D-glucopyranosyl)-5-O-{3-O-(2-acetamido-2-deoxy-β-D-glucopyranosyl)-5-O-{3-O-(2-acetamido-2-deoxy-β-D-glucopyranosyl)-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[sodium phosphinato]-D-ribitol]-1-O-[sodium phosphinato]-D-ribitol}-1-O-[(2-[(4-hydrazino-4-oxobutanoyl)amino]ethoxy)(sodium phosphinato)]-D-ribitol (3)

Compound 69 (50 mg, 12.5 μmol) was treated according to the procedure described in Step 2.16 to give an intermediate to which hydrazine hydrate (0.50 mL, 5.73 mmol) was added. The reaction mixture was stirred for 1 h at rt and eluted on a Sephadex® G25 column (water). The mixture of target compound 3 and the activated ester was concentrated in vacuo, diluted with water (3 mL) and reacted with hydrazine hydrate (0.32 mL, 3.63 mmol) for 2 h at rt. After purification by size exclusion chromatography on Sephadex® G25 (water), by preparative ionic Dionex chromatography followed by size exclusion chromatography on Sephadex® G25 (water), 25 mg (53%) of target compound 3 was obtained as white solid after lyophilisation.

ESI HRMS: $C_{123}H_{220}N_{12}O_{111}P_{9}$ m/z calcd for $[M+3H+Na]^{5-}$ 789.40, found 789.40. CE (method 8b): MW=5.65 min III) Preparation and Characterization of the Octamer and Nonamer Conjugates Each of the synthetic oligosaccharides produced according to the methods described in Examples 1 (β(1,4) octamer), 2 (α(1,4) octamer) and 3 (β(1,3) nonamer) was mixed with rEPA and EDAC to obtain a final concentration of 5 mg/mL, 1 mg/mL and 50 mM respectively in 150 mM NaCl 50 mM MES buffer, pH 5.7. The mixture was incubated at room temperature for 3 hours. Each conjugate obtained was purified by size exclusion chromatography on Superdex 75 gel to separate it from unconjugated protein and unconjugated synthetic oligosaccharide. The conjugates were then formulated in PBS for immunogenicity testing.

Conjugates were characterized for saccharide to protein ratio and size. The molar mass of each conjugate was determined using a TDA301 Viscotek HPSEC system combined with a TSKgel G3000 column. 100 μL of each solution were injected into the columns and eluted with 0.2 M phosphate buffer pH 6.9 at a flow rate of 0.5 mL/min. The $M_w$ of each conjugate (in kDa) was calculated by the OmniSEC 4.2 software. The absence of unconjugated protein was confirmed by SDS-PAGE. The features of the synthetic oligosaccharide conjugates are summarized in the table below.

| Conjugate | Oligosaccharide concentration μg/mL | Protein concentration μg/mL | Ratio Prot/OS w:w | Ratio Prot/OS M:M | Size kDa |
|---|---|---|---|---|---|
| β(1,3) Nona-rEPA | 41 | 81 | 2.0 | 9.0 | ND |
| β(1,4) Octa-rEPA | 71 | 191 | 2.7 | 7.2 | 115 |
| α(1,4) Octa-rEPA | 60 | 171 | 2.9 | 6.7 | 118 |

ND: not determined

IV) Extraction, Purification and Characterization of the Native Polysaccharides (Teichoic Acids) from Bacterial Strains The Wood 46 *S. aureus* strain (ATCC 10832), which is a 100% β(1-4) strain, the Newman D2C *S. aureus* strain (ATCC 25904), which is a 100% α(1-4) strain and the *S. aureus* strain with the reference number ATCC 55804, which is a 100% β(1-3) strain, were cultivated overnight in TSB. The entire culture of each strain was then inactivated by treatment with phenol-ethanol (1:1, v/v) to a final concentration of 2%. The inactivated *S. aureus* cells were separated from the culture broth by centrifugation for 1 hour at 5,000 g and +4° C. The supernatant was discarded and the cell paste was suspended in 0.05 M Tris, 2 mM $MgSO_4$ pH 7.5 (0.5 g wet weight/mL). Lysostaphin (5 mg/mL in water) was added to a final concentration of 100 μg/mL and the reaction mixture was incubated at 37° C. for 3 hours with stirring. 100 mM $MgCl_2$ and benzonase (2.5 UI/mL) were subsequently added to a final concentration of 1 mM and 50 UI/mL respectively and incubated at 37° C. for 4 hours with stirring. Finally, the concentration of Tris buffer was adjusted to 50 mM and $CaCl_2$ and Pronase were added to final concentrations of 1 mM and 0.5 mg/mL respectively. The reaction mixture was incubated for 16 hours at 37° C. and subsequently centrifuged for 30 min at 8,000 g and 4° C.

$CaCl_2$ powder was added to the supernatant to a final concentration of 10 mM and the reaction mixture was precipitated with 25% ethanol and stirred for 16 hours at +4° C. After centrifugation (8,000 g for 15 min), the pellet was discarded. The supernatant was precipitated with 75% ethanol in the presence of 10 mM $CaCl_2$ and stirred for 4 hours at +4° C. The 75% ethanol precipitate was pelleted by centrifugation at 8,000 g for 30 minutes and re-dissolved in water. The solution was dialyzed extensively against water at room temperature.

1 M Tris buffer pH 7.0 was added to a final concentration of 50 mM and loaded onto a Q Sepharose column. The teichoic acids (TAs) were separated from residuals using a 0-0.5 M NaCl linear gradient in 50 mM Tris buffer pH 7.0. Fractions that contained teichoic acid, as detected by ribitol assay using HPAEC-PAD were pooled, extensively dialyzed against water at room temperature and freeze-dried.

Analysis of the monosaccharide composition of TAs by HPAEC (high pH anion exchange chromatography) after 48% hydrofluoric acid (HF) and 2M trifluoroacetic acid (TFA) hydrolysis showed the presence of ribitol and glucosamine at a molar ratio of 1:1 for the three structures, as expected.

Proton nuclear magnetic resonance spectra of purified TAs were consistent with the structure of TAs comprising 1,5-poly(ribitol phosphate) polymers in which position 4 or 3 of the ribitol is substituted by N-acetyl-D-glucosamine (GlcNAc). In accordance with published data, the chemical shifts of their respective single anomeric proton as evidenced in FIGS. 1 to 3 indicate that the anomeric status and position of the GlcNAc moieties on the ribitol residues of the TA from the Newman D2C strain is GlcNAc α(1,4) (5.07 ppm), the anomeric status and position of the GlcNAc moieties on the ribitol residues of the TA from the Wood 46 strain is GlcNAc β(1,4) (4.75 ppm) and the anomeric status and position of the GlcNAc moieties on the ribitol of TA from strain ATCC 55804 (PS336) is GlcNAc β(1,3) (4.66 ppm).

The molar masses of each purified TA were determined using a TDA301 Viscotek HPSEC system combined with a TSKgel G3000 column. A solution of each purified teichoic acid was prepared at a concentration of 2 mg/mL in water. 100 L of each solution was injected into the columns and eluted with 0.2 M phosphate buffer pH 6.9 at a flow rate of 0.5 mL/min. $M_w$ and Pd (polydispersity calculated from the formula $M_w/M_n$; where $M_n$ is the number average molar mass; and $M_w$ the weight average molar mass) were calculated by the OmniSEC 4.2 software. The molar mass distributions of the three purified polysaccharides were narrow, as reflected by the low values of polydispersity (Pd=1.1). $M_w$ of alpha-linked GlcNAc TA and beta-linked GlcNAc TAs were identical and approximately 18,000 g/mol. As the molar mass of the TA repeat unit is 438 g/mol, the number of repeat units in each polymer was approximately 40.

V) Preparation and Characterization of the Native Polysaccharide (Teichoic Acid) Conjugates The purified TAs as described in paragraph IV were coupled to rEPA or detoxified double mutant *S. aureus* alpha toxin (HladM) as carrier protein using the linking agent adipic acid dihydrazide (ADH). First, TAs were derivatized with ADH. Polysaccharides were dissolved in 200 mM NaCl at 10 mg/mL. 900 mM ADH in water was added to obtain a final concentration of 500 mM and the pH was adjusted to 5.7 with 1 M HCl. 1 M EDAC in water was added to obtain a final concentration of 100 mM and the pH was maintained at 5.7 at room temperature for 3 hours. The pH was adjusted to 7.0 with 0.5 M NaOH. The reaction mixture was dialysed at room temperature against 0.5 M NaCl for 2 days with 7 changes, then against water for 3 days with 4 changes and freeze-dried. The ADH-derivatized TAs were named using the abbreviation TA-AH. Derivatization with ADH was measured by the TNBS colorimetric assay (Snyder and Sobocinski (1975), Anal. Biochem. 64 pp: 284-288). ADH derivatization of TAs ranged from 2.3 to 4.3% (w/w).

TA-AHs were mixed with rEPA and EDAC to a final concentration of 4 mg/mL, 4 mg/mL and 50 mM respectively in 150 mM NaCl 50 mM MES buffer pH 5.7. The mixture was incubated at room temperature for 3 hours.

Each conjugate obtained was then purified by size exclusion chromatography on Sepharose 6BCl gel to separate it from unconjugated protein and unconjugated polysaccharide. The conjugate was then formulated in PBS for immunogenicity testing. Conjugates were characterized for polysaccharide to protein ratio and size. Molar masses of each conjugate were determined using a TDA301 Viscotek HPSEC system combined with a TSKgel G3000 column. 100 μL of each solution was injected into the columns eluted with 0.2 M phosphate buffer pH 6.9 at a flow rate of 0.5 mL/min. $M_w$ were calculated by the OmniSEC 4.2 software. The absence of unconjugated TA was checked by micellar capillary electrophoresis (MEKC). The features of the TA conjugates are summarized in the table below.

| Conjugate | Polysaccharide concentration μg/mL | Protein concentration μg/mL | Ratio Prot/PS w:w | Size kDa |
|---|---|---|---|---|
| β(1,3)TA-rEPA | 193 | 356 | 1.8 | 1,600 |
| β(1,4)TA-rEPA | 90 | 265 | 2.9 | 516 |
| α(1,4)TA-rEPA | 159 | 366 | 2.3 | 477 |
| β(1,4)TA-HladM | 100 | 220 | 2.2 | 75 |

VI) Evaluation of the Immunogenicity of the Unconjugated and Conjugated Saccharides VI-1) Immunization Protocols The immunogenicity of the saccharides and rEPA-based conjugates as described in paragraphs I to V, were tested in various conditions in outbred OF-1 mice. The following forms of the saccharides were tested (in PBS solution: phosphate 10 mM, NaCl 200 mM, pH=7.2):

unconjugated synthetic oligosaccharides linked to the linking agent ADH: β(1,4) octamer-AH (compound 1); α(1,4) octamer-AH (compound 2) and β(1,3) nonamer-AH (compound 3), unconjugated native TAs linked to ADH: β(1,4) TA-AH; α(1,4) TA-AH and β(1,3) TA-AH synthetic oligosaccharides conjugated to rEPA via the linking agent: β(1,4) octamer-AH-rEPA; α(1,4) octamer-AH-rEPA and β(1,3) nonamer-AH-rEPA, and native TAs conjugated to rEPA via the ADH linking agent: β(1,4) TA-AH-rEPA; α(1,4) TA-AH-rEPA and β(1,3) TA-AH-rEPA).

In all immunization protocols, OF1 mice were administered an amount of the compound to be tested that corresponds to 5 μg of saccharide. Doses were administered via the SC route in the scapular region on D0, D21 and D35. The mice that were immunized with the non-conjugated saccharides were also given 9 μg of rEPA per dose of oligosaccharide, which is within the range of the amount of rEPA injected per mouse in the groups of mice immunized with the conjugated saccharides. Depending on the test to be carried out, the immunogenicity of the saccharides (either non conjugated or conjugated to rEPA) was assessed in presence or absence of AF04, which is a Th1 adjuvant. For the groups of mice that were immunized with the AF04 adjuvant alone (as negative control) or with the compound to be tested in the presence of AF04, the method that was carried out was as follows: AF04, a squalene-based oil in water (O/W) emulsion that contains a TLR4 agonist, was obtained according to the process described in WO 2007/080308. Briefly, in a first step, a concentrated thermoreversible squalene-based O/W emulsion was prepared according to the protocol described in example 1 of WO 2007/080308. The concentrated O/W emulsion was then diluted in a PBS solution to obtain a squalene concentration of 5% in the emulsion, the composition of which was as follows: Squalene: 50 mg/mL; Ceteareth-12 (Emulgin B1): 9.5 mg/mL; Sorbitan monoleate (Dehymuls SMO): 7.4 mg/mL, mannitol: 9 mg/mL, E6020: 40 µg/mL. This diluted O/W emulsion was then mixed volume to volume with the solution of the compound to be tested for immunogenicity or with PBS (for the negative control group of mice immunized with AF04 alone) before administration to mice so that each mouse was given per injection an amount of 4 µg of E6020 in a 2.5% squalene-based O/W emulsion.

VI-2) Analyses of the Antibody Responses Induced by Unconjugated and Conjugated Saccharides For each mouse, sera were collected from blood samples taken on D0, D21, D35 and D42 and stored at −20° C. until use. The level of the antibody response directed against the saccharide that was used in the immunization protocol was assessed by ELISA using as coating agent the corresponding teichoic acid linked to ADH (TA-AH). For instance, when the saccharide used in the immunization protocol was the β(1,3) nonamer-AH-rEPA, β(1,3) AT-AH was used as the coating agent in the ELISA. Briefly, the ELISA was carried out by coating overnight at +4° C. ELISA plates (Dynex Ref: 655071) with 100 µL per well of a TA-ADH at 1.5 µg/mL in carbonate buffer solution (pH: 9.6), followed by a saturation step with a saturation buffer (PBS/Tween 0.05%/Bovine Serum Albumin 1%) (100 µL/well). Serial dilutions of the sera to be tested in saturation buffer were then added to the wells. After incubation for 90 min at 37° C. followed by successive washes, 100 µL of an anti-mouse Ig conjugated to horseradish peroxidase solution diluted as needed in saturation buffer according to the class of Ig measured, was added to each well. After a further incubation for 90 min at 37° C. followed by successive washes, the intensity of the enzymatic reaction which reflects the amount of anti mouse Ig fixed per well was measured using the well-known tetramethylbenzidine substrate. Absorbance was measured at 450 and 650 nm. Antibody titers were expressed as arbitrary units using Softmax Pro Software corresponding to reciprocal serum dilutions for $OD_{450\,nm}=1$. Threshold value of ELISA assay was determined by biostatistics analyses at 1.3 Log.

VI-3) Results

In a first series of tests, the importance of the conjugation as well as the role of the adjuvant were assessed in mice immunized with conjugated or unconjugated β(1,3) saccharides, wherein the GlcNAc residues are all in position β(1,3) on the ribitol groups.

The groups of mice which were tested are listed in the table below.

| Group name | Composition tested |
|---|---|
| 336 conjugate | β(1,3) TA-ADH-rEPA |
| 336 conjugate + AF04 | β(1,3) TA-AH-rEPA + AF04 |
| Synthetic nonamer conjugate | β(1,3) nonamer-AH-rEPA |
| Synthetic nonamer conjugate + AF04 | β(1,3) nonamer-AH-rEPA + AF04 |
| rEPA + nona-AH + AF04 | β(1,3) nonamer-AH + rEPA + AF04 |
| rEPA + 336-AH + AF04 | β(1,3) TA-AH + rEPA + AF04 |
| AF04 | AF04 |
| PBS | PBS |

Figure 4:
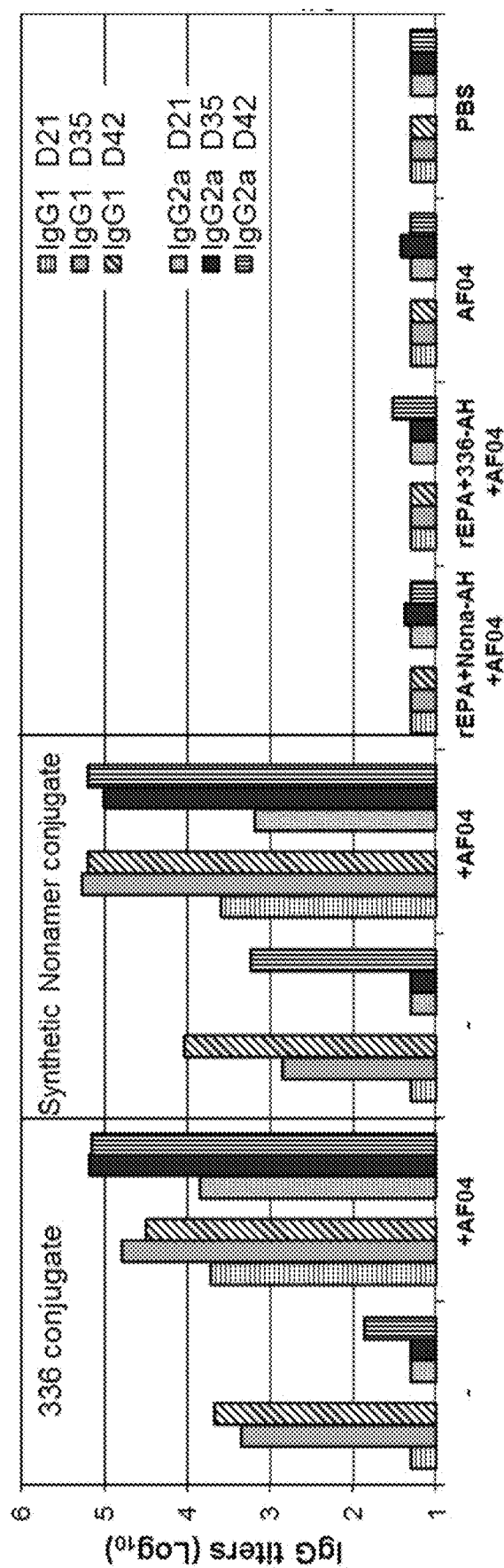
FIG. 4 represents the evolution of the specific IgG1 and IgG2a titers directed against purified β(1,3) TA (336 Ag) after one (D21), two (D35) or three (D42) immunizations with either unconjugated β(1,3) saccharides (synthetic nonamer or native TA) or with conjugated β(1,3) saccharides [synthetic β(1,3) nonamer conjugate or β(1,3) TA conjugate] in the presence or in the absence of the AF04 adjuvant.

The results displayed in FIG. 4 clearly indicate:
1) The unconjugated β(1,3) saccharides, whatever their origin (synthetic or native) are unable to induce a specific immune response against the saccharide. AF04 has no effect since the unconjugated β(1,3) saccharides formulated with AF04 remain unable to trigger a specific immune response.
2) In contrast, the conjugated β(1,3) saccharides, whatever the origin of the saccharide (synthetic or native) are able to induce a specific immune response against the saccharide after the second immunization, with said immune response being even stronger after the third immunization, (indicative of a "boost effect" of the carrier protein). The antibody responses are increased when the β(1,3) saccharides conjugates are formulated with AF04. The antibody responses induced by the synthetic β(1,3) nonamer conjugate (formulated or not with AF04) are similar to those induced by the 336 conjugate.

In a second series of tests, the importance of conjugation to a carrier protein was tested in mice immunized with conjugated or unconjugated β(1,4) saccharides (wherein the GlcNAc residues are all in position β(1,4) on the ribitol groups) and in mice immunized with conjugated or unconjugated α(1,4) saccharides, wherein the GlcNAc residues are all in position α(1,4) on the ribitol groups. All the compositions tested were formulated with AF04.

The groups of mice which were tested are listed in the table below.

| Group name | Composition tested |
|---|---|
| TA α(1,4) + rEPA | α(1,4) TA-AH + rEPA + AF04 |
| TA β(1,4) + rEPA | β(1,4) TA-AH + rEPA + AF04 |
| octamer α(1,4)-rEPA | α(1,4) octamer-AH-rEPA + AF04 |
| TA α(1,4)-rEPA | α(1,4) TA-AH-rEPA + AF04 |
| octamer β(1,4)-rEPA | β(1,4) octamer-AH-rEPA + AF04 |
| TA β(1,4)-rEPA | β(1,4) TA-AH-rEPA + AF04 |
| AF04 | AF04 |

The results displayed in FIG. 5 clearly indicate:
1) The unconjugated β(1,4) saccharides as well as the unconjugated α(1,4) saccharides (either synthetic or native) are unable to induce a specific immune response against the saccharide even in the presence of AF04; the level of antibody response after 3 immunizations is the same as the one observed in the AF04 negative control group.
2) On the contrary, as previously shown, the β(1,4) saccharide conjugates, and the α(1,4) saccharides conjugates whatever the origin of the saccharide (synthetic or native) are able to induce a specific immune response against the corresponding saccharide. The synthetic β(1,4)-octamer conjugate [β(1,4) octamer-AH-rEPA)] is as immunogenic as the hemi-synthetic β(1,4)-octamer conjugate [β(1,4) TA-AH-rEPA], but is more immunogenic than the synthetic α(1,4)-octamer conjugate [α(1,4) octamer-AH-rEPA].

VII) Cross Reactivity Studies of the Immune Sera from Mice Immunized with Either Conjugated α(1,4) Saccharides, Conjugated β(1,4) Saccharides or Conjugated β(1,3) Saccharides.

The immune sera from mice immunized with either conjugated α(1,4) saccharides [α(1,4) octamer-AH-rEPA or α(1,4) TA-AH-rEPA], conjugated β(1,4) saccharides [β(1,4) octamer-AH-rEPA or β(1,4) TA-AH-rEPA] or conjugated β(1,3) saccharides [β(1,3) nonamer-AH-rEPA or β(1,3) TA-AH-rEPA], were then tested by flow cytometry for their ability to recognize a broad panel of S. aureus strains that express structurally different TA. The immunization protocol described in paragraph VI-1) was utilised, except that all the immunogens tested were formulated with AF04. A group of mice immunized with AF04 alone was also introduced and used as "negative control group" (not presented). The immune sera of each group of mice (comprising at least 5 mice per group) were collected on D42, pooled and tested by flow cytometry against the panel of the 19 S. aureus strains described in paragraph 1 of the examples.

The strains were grown in Difco Tryptic Soy Broth (TSB) (Beckton Dickinson—ref: 211825) for 20 h at 37° C. with gentle stirring (110 rpm). After centrifugation of an aliquot of each culture, followed by a wash with a PBS-1% BSA Immunofluorescence (IF) buffer, each bacterial suspension was adjusted to $10^8$ CFU/mL in the IF buffer. To avoid the nonspecific signal generated by protein A expressed on the surface of S. aureus strains, about $10^8$ CFU of each bacterial suspension were incubated for 1 hour at 37° C. under shaking with a 100 µg/mL guinea pig IgG solution (Bioscience, ref 006-000-003). After centrifugation followed by a wash with IF buffer, 20 µL of the $10^8$ CFU/mL bacterial suspension was pipetted into the wells of a 96 well plate (Ritter—ref: 539034). 20 µL of a ten-fold dilution of each pooled immune serum ("test sample") or the "negative control" pooled serum was then added to the wells. All the sera were tested in duplicate. After incubation for 1 hour at 37° C. with stirring (200 rpm), the wells were washed twice with 400 µL of IF buffer. The bacterial pellets in each well were then re-suspended with 100 µL of a diluted solution of Phycoerythrin-labeled goat anti-mouse F(ab')$_2$ IgG (Southern Biotech-ref: 1032-09) diluted in IF buffer. A few wells that contained only Ig-treated bacterial suspension were used as "controls" and re-suspended with either 100 µL of IF buffer ("bacterial" control) or with 100 µL of the same diluted solution of Phycoerythrin-labeled goat anti mouse F(ab')$_2$ IgG (Southern Biotech-ref: 1032-09) ("antibody" control). After a 1 hour incubation at 37° C. with stirring (200 rpm), the wells were washed twice with 400 µL of IF buffer and then re-suspended with 500 µL of IF buffer for FACS analysis. For each immune serum tested the data were visualized under the form of a histogram based on the analysis of the fluorescence and scatter parameters. For each histogram, a geometric mean of fluorescence intensity (MFI) was then calculated by the software. A "ratio value" for each test sample was then calculated from the ratio between the mean value of the two MFI provided by the "test sample" tested in duplicate and the mean value of the two MFI provided by the "negative control group" serum. A ratio value above 2 was considered as positive and meant that the pooled immune serum tested recognized the strain of S. aureus that was deposited in the wells. The higher the ratio value, the stronger the recognition of the S. aureus strain by the pooled immune serum tested.

| | | Immunogen adminstered to mice | | | | | |
|---|---|---|---|---|---|---|---|
| TA type | reference | α(1,4) octamer-AH-rEPA | α(1,4) TA-AH-rEPA | β(1,4) octamer-AH-rEPA | β(1,4) TA-AH-rEPA | β(1,3) nonamer-AH-rEPA | β(1,3) TA-AH-rEPA |
| 100% α(1-4) | Newman D2C | 3.7 | 3.4 | 2.5 | 2.1 | 1.4 | 1.2 |
| | HT20050843 | 8.1 | 6.8 | 8.5 | 3.1 | 1.4 | 1.0 |
| Mix α(1-4) and β(1-4) | HT20050726 | 4.9 | 4.5 | 2.3 | 2.1 | NT | NT |
| | HT20050702 | 7.5 | 6.6 | 11.4 | 6.2 | NT | NT |
| 100% β(1-4) | HT20050742 | 3.0 | 3.0 | 14.7 | 8.4 | 2.6 | 1.1 |
| 100% β(1-3) | HT20050667 | 2.5 | 1.5 | 3.4 | 1.8 | 5.7 | 1.7 |
| | ATCC55804 | 2.8 | 1.7 | 4.1 | 2.8 | 10 | 1.8 |

The results shown in the table above and in FIG. 6 clearly indicate:

The pooled immune sera from mice immunized with the synthetic conjugates [α(1,4) octamer-AH-rEPA, β(1,4) octamer-AH-rEPA and β(1,3) nonamer-AH-rEPA] more strongly recognize the homologous and heterologous strains of S. aureus than the pooled immune sera from mice immunized with the respective hemi-synthetic conjugates [α(1,4) TA-AH-rEPA, β(1,4) TA-AH-rEPA and β(1,3) TA-AH-rEPA].

The pooled immune sera from mice immunized with either the synthetic β(1,4) octamer conjugate [β(1,4) octamer-AH-rEPA] or the synthetic α(1,4) octamer conjugate [α(1,4) octamer-AH-rEPA] recognize a much broader panel of S. aureus strains than the pooled immune serum from mice immunized with the synthetic β(1,3) nonamer conjugate [β(1,3) nonamer-AH-rEPA]. The pooled immune serum from mice immunized with the synthetic β(1,3) nonamer conjugate almost exclusively recognize the homologous 100% β(1-3) strains (a ratio value only slightly above 2 was observed with only one 100% β(1-4) strain among the five 100% β(1-4) strains tested and with only one "mix α(1-4) and β(1-4)" strain among the seven "mix α (1-4) and β (1-4)" strains tested). In contrast, the pooled immune sera from mice immunized with the synthetic β(1,4) octamer conjugate and from mice immunized with the synthetic α(1,4) octamer conjugate are broadly "cross reactive" since they recognize almost all the S. aureus strains tested. As shown in FIG. 6, they recognize 100% β(1-3) strains, 100% β(1-4) strains, 100% α(1-4) strains, as well as mix α (1-4) and β (1-4) strains. The pooled immune serum from mice immunized with the synthetic β(1,4) octamer conjugate more strongly recognize the S. aureus strains with a higher ratio value than the pooled immune serum from mice immunized with the synthetic α(1,4) octamer conjugate.

In conclusion, use of a conjugate of a saccharide comprising repetitive units of 1,5 ribitol phosphate in which all the ribitol residues are substituted by N-acetyl D-glucosaminyl residues at the 4-position and wherein said GlcNAc residues are exclusively in anomeric configuration α or anomeric configuration β, contributes to the reduction of number of antigens to be combined in a S. aureus vaccine. As shown in FIG. 6, each of the two conjugates induces cross reactive antibodies that recognize almost all the strains of S. aureus tested. To obtain a similar pattern of recognition using capsular polysaccharide conjugates as immunogens, it would require the use of a PS5 conjugate, a PS8 conjugate and a conjugate of a saccharide comprising units of 1,5 ribitol phosphate in which all the ribitol residues are substituted by N-acetyl D-glucosaminyl residues at the 3-position and which are in anomeric configuration β.

VIII) Comparison of the Immunogenicity of β(1,4)TA-HladM and β(1,4)TA-rEPA Conjugates in Mice The immunogenicity of the purified native β(1,4)TA-HladM and β(1,4)TA-rEPA conjugates as described in paragraph V was tested in outbred OF-1 mice (Charles River Laboratories; age: 7 weeks old on D0; sex: female). The mice were divided into 4 groups with 30 mice in each group (see the table below for the compositions received by each group). For all groups, mice were injected, on D0, D21 and D35 via the SC route (0.2 mL/injection) in the right flank for the first injection, in the left flank for the second and in the scapular girdle for the third injection. The adjuvant administered (which was different from the adjuvant AF04 administered in Example VI) was an aluminium hydroxide salt including the TLR4 agonist E6020 (E6020 is described in WO 2007/005583). E6020 liposomes were made by the ethanol injection method and were then adsorbed onto aluminium hydroxide and diluted in a mixture of PBS and Tris buffer (50 mM Tris, 100 mM NaCl, 88 mM phosphate, pH 7.4). The adjuvant was diluted volume for volume with the tested composition in PBS solution such that the adjuvanted composition administered to the mice contained 240 µg aluminium and 4 µg E6020. The mice in groups 2 to 4 each also received an identical cocktail of additional proteins in combination with the compositions listed in the table below. Blood samples were collected under anesthesia on D45 in the sub-mandibular region. Anesthesia was performed by maintaining the mouse in a compartment with isoflurane gas for 3 minutes. Blood samples of around 200 µL were collected in tubes containing clot activator and serum separator (BD Microtainer SST, ref 365951). The tubes were centrifuged at 4000 rpm for 15 min in order to separate serum from blood cells. The sera were transferred into Deepwell (ritter) and heat-inactivated at +56° C. for 30 min. They were stored at −20° C. until used for the ELISA test.

| Group | Composition tested |
|---|---|
| 1 | PBS + adjuvant |
| 2 | HladM + adjuvant |
| 3 | β(1,4)TA-HladM + adjuvant |
| 4 | β(1,4)TA-rEPA + adjuvant |

IgG1 and IgG2 antibodies generated by the each of the components of the tested compositions were quantified by ELISA from pools of sera collected from each immunised group using the relevant antigen as coating antigen. Briefly, the plates were coated with 100 µL per well of 1.5 µg/mL of the relevant antigen and kept overnight at +4° C. Free sites were blocked with 150 µL of buffer 1 (PBS/Tween 0.05%/Bovine albumin 1%) and after a 60 min incubation period at +37° C., the plates were emptied. The sera were serially diluted in buffer 1 in a volume of 100 µL (12 times) in the microplates. The plates were incubated for 90 min at +37° C. and then washed with buffer 2 (PBS/Tween 0.05%). 100 µl of a diluted anti-mouse IgG1 or anti-mouse IgG2a peroxidase conjugate was added to each well. After 90 min incubation at +37° C., the plates were washed with buffer 2. The reaction was developed by adding 100 µL of a tetramethylbenzidine substrate solution in each well. The reaction was chemically stopped after 30 min at room temperature with HCl (1N) and absorbance was measured at 450-650 nm. The results were expressed in arbitrary ELISA units/mL by the reciprocal of the dilution corresponding to the OD=1 using SoftmaxPro software.

The humoral responses (IgG1 and IgG2a antibodies as quantified by ELISA) to each of the components of of the tested compositions are shown in the following tables.

| β(1,4)TA antibody response | | |
|---|---|---|
| Group | IgG1 | IgG2a |
| 1 | 1.70 | 1.70 |
| 3 | 5.17 | 4.32 |
| 4 | 5.25 | 4.47 |

| HladM antibody response | | |
|---|---|---|
| Group | IgG1 | IgG2a |
| 1 | 4.17 | 3.99 |
| 2 | 6.13 | 6.25 |
| 3 | 6.10 | 5.94 |

| rEPA antibody response | | |
|---|---|---|
| Group | IgG1 | IgG2a |
| 1 | 1.70 | 1.70 |
| 4 | 5.39 | 5.15 |

These data demonstrate that the tested conjugates are capable of inducing a robust and specific anti-teichoic acid antibody response in mice regardless of whether the teichoic acids are conjugated to rEPA or HladM as carrier protein. Furthermore, these data demonstrate that the tested teichoic acid conjugates are capable of inducing an antibody response in mice when adjuvanted with an alum-based adjuvant as an alternative to the squalene-based oil in water emulsion adjuvant (AF04) described in paragraph VI.

Alpha-Hemolysin (Hla) Neutralisation

Alpha-hemolysin neutralization titers of mice sera were determined based on neutralization of hemolysis of Rabbit Red Blood Cells (RRBC) when pre-incubated with native alpha-hemolysin. Briefly, 25 ng of purified native Hla was pre-incubated at room temperature with different concentrations of sera obtained from the mice immunized with the compositions described in the table above. Sera were tested at 1:10 final starting concentration and two-fold serial diluted, then incubated with 1.10$^7$ rabbit red blood cells at +37° C. for 30 min. Following incubation, samples were centrifuged for 3 min at 800 g+4° C. (acceleration 9, deceleration 9). Absorbance in the supernatant was determined in a Versamax™ plate reader (Molecular Devices) at 405 nm. A standard control rabbit polyclonal antibody anti-Hla (Sigma, S7531) was also included in the assay during each run. The Hla neutralization titre was defined as the reciprocal of the highest dilution of the serum resulting in 50% inhibition of the toxicity of Hla.

The results are shown in the following table.

| Group | Neutralising titre (NT$_{50}$) | |
|---|---|---|
| | RRBC assay 1 | RRBC assay 2 |
| 1 | <10 | <10 |
| 2 | 164 | 168 |
| 3 | 137 | 139 |
| 4 | <10 | <10 |

As can be seen from the above table, antibodies generated by all compositions containing HladM (Group 2) or HladM-TAβ1-4 (Group 3) were able to neutralise the haemolytic activity of the native toxin. Furthermore, no significant differences in neutralizing antibody titers were observed between combinations containing HladM or HladM-TAβ1-4, indicating that conjugation of the HladM to teichoic acid does not impact the ability of HladM portion of the conjugate to induce specific anti-Hla antibodies that are able to neutralise native Hla.

The invention claimed is:

1. A conjugate of a saccharide covalently bound to a carrier protein, wherein the saccharide comprises repetitive units of 1,5 ribitol phosphate in which all the ribitol residues are substituted by N-acetyl D-glucosaminyl residues at the 4-position, wherein said N-acetyl D-glucosaminyl residues are exclusively in anomeric configuration α or are exclusively in anomeric configuration β and wherein the carrier protein comprises at least one chain of amino acids which is an epitope recognized by T helper lymphocytes.

2. A conjugate according to claim 1, wherein the saccharide consists of repetitive units of 1,5 ribitol phosphate in which all the ribitol residues are substituted by N-acetyl D-glucosaminyl residues at the 4-position, wherein said N-acetyl D-glucosaminyl residues are exclusively in anomeric configuration a or are exclusively in anomeric configuration β.

3. A conjugate according to claim 1, wherein the saccharide is extracted from the cell wall of S. aureus.

4. A conjugate according to claim 1, wherein the saccharide is obtained by chemical synthesis.

5. A conjugate according to claim 1, wherein all the repetitive units have the following structure, or a salt thereof:

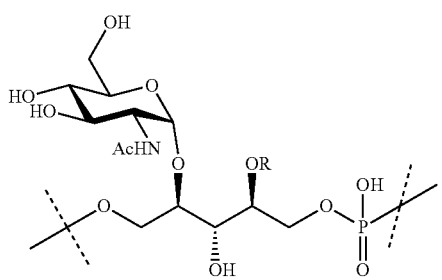

wherein:
R is independently H or D-Ala, and R can be different from one repetitive unit to another, and
the N-acetyl D-glucosaminyl residue is in anomeric configuration α.

6. A conjugate according to claim 1, wherein all the repetitive units have the following structure, or a salt thereof:

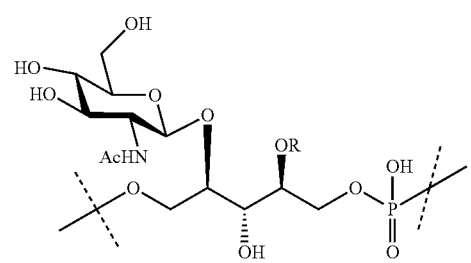

wherein:
R is independently H or D-Ala, and R can be different from one repetitive unit to another, and
the N-acetyl D-glucosaminyl residue is in anomeric configuration β.

7. A conjugate according to claim 5 wherein R is H.

8. A conjugate according to claim 1 wherein the number of the repetitive units is ≥4.

9. A conjugate according to claim 1 wherein the carrier protein is linked to the terminal phosphate of the saccharide.

10. A conjugate according to claim 1, wherein the saccharide is covalently bound to the carrier protein via a linker.

11. A conjugate according to claim 10 having the following structure:

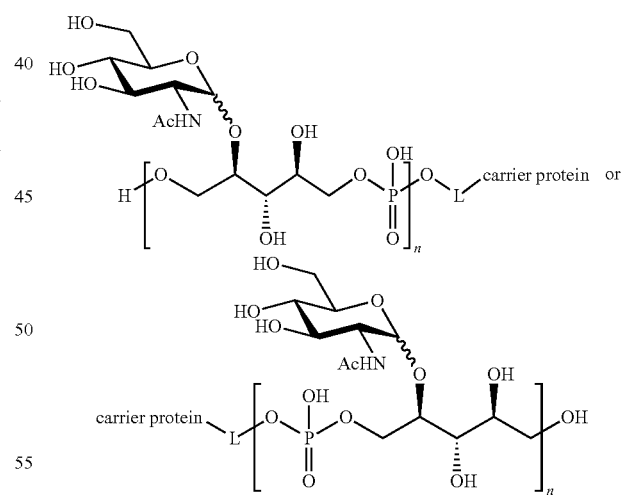

wherein:
the N-acetyl D-glucosaminyl residues are exclusively in anomeric configuration α or exclusively in anomeric configuration β;
n is ≥4; and
L is a linker;
or a salt of one of these structures.

12. A conjugate according to claim 11 having the following structure:

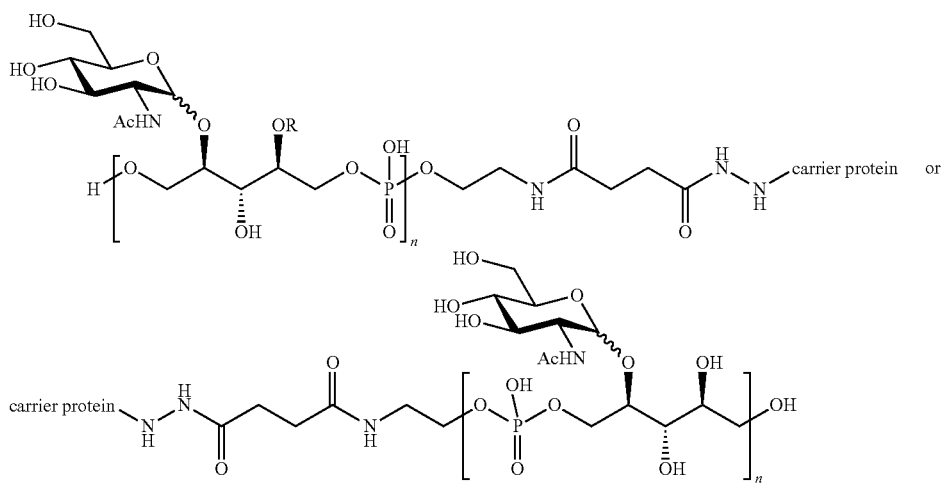

wherein:
the N-acetyl D-glucosaminyl residues are exclusively in anomeric configuration α or exclusively in anomeric configuration β;
and n is ≥4;
or a salt of one of these structures.

13. A conjugate according to claim 11, wherein said N-acetyl D-glucosaminyl residues are exclusively in anomeric configuration β.

14. A conjugate according to claim 1 which comprises less than 5% w/w peptidoglycan.

15. A conjugate according to claim 1, wherein the carrier protein is a detoxified bacterial toxin.

16. A conjugate according to claim 15, wherein the detoxified bacterial toxin is the Exoprotein A of *Pseudomonas aeruginosa*.

17. A conjugate according to claim 15, wherein the detoxified bacterial toxin is a hemolysin of *S. aureus*.

18. A conjugate according to claim 1, wherein the weight ratio between the saccharide and the carrier protein is between 0.1 and 10.

19. A composition comprising a conjugate according to claim 1, and an adjuvant.

20. A composition according to claim 19, wherein the adjuvant is a Toll Like Receptor 4 agonist.

21. A composition according to claim 20, wherein the Toll Like Receptor 4 (TLR4) agonist is in combination with a delivery system.

22. A composition according to claim 20, wherein the Toll Like Receptor 4 agonist is E6020 (CAS number: 287180-63-6).

23. A composition according to claim 19, wherein the adjuvant is at least one of a Th1, a Th17, and a Th1/Th17 adjuvant.

24. A conjugate of a saccharide covalently bound to a carrier protein, wherein the saccharide comprises repetitive units of 1,5 ribitol phosphate in which all the ribitol residues are substituted by N-acetyl D-glucosaminyl residues at the 4-position, wherein said N-acetyl D-glucosaminyl residues are exclusively in anomeric configuration β and wherein the carrier protein provides at least one epitope to the conjugate which is recognized by T helper lymphocytes, or a composition according to claim 19,
wherein the conjugate induces the production of antibodies that bind to *S. aureus* type 336 strain deposited under ATCC 55804, Wood 46 strain of *S. aureus* deposited under ATCC number 10832 and the Newman D2C strain deposited under ATCC number 25904.

25. A method for preparing a conjugate as claimed in claim 1 comprising:
a) providing a saccharide that comprises repetitive units of 1,5 ribitol phosphate in which all the ribitol residues are substituted by N-acetyl D-glucosaminyl residues at the 4-position, and wherein said N-acetyl D-glucosaminyl residues are exclusively in anomeric configuration α or are exclusively in anomeric configuration β, wherein said saccharide is as defined in claim 1;
b) providing a carrier protein;
c) derivatizing said saccharide with a linking agent and coupling the derivatized saccharide with said carrier protein or, alternatively, derivatizing said carrier protein with a linking agent and coupling the derivatized carrier protein to said saccharide to obtain the conjugate.

26. A method as claimed in claim 25, wherein the saccharide is derivatized using a dihydrazide or wherein the saccharide is derivatized using a di-activated diester followed by treatment with hydrazine.

27. A method for preparing a conjugate as claimed in claim 1 comprising:
a) providing a saccharide that comprises or consists of repetitive units of 1,5 ribitol phosphate in which all the ribitol residues are substituted by N-acetyl D-glucosaminyl residues at the 4-position, and wherein said N-acetyl D-glucosaminyl residues are exclusively in anomeric configuration α or are exclusively in anomeric configuration β, wherein said saccharide is as defined in claim 1;
b) providing a carrier protein;
c) derivatizing said saccharide with a first linking agent;
d) derivatizing said carrier protein with a second linking agent; and
e) coupling said derivatized saccharide to said derivatized carrier protein to obtain the conjugate.

28. The method as claimed in claim 27, wherein the linking agent for derivatizing the saccharide is cysteine, cysteamine or cystamine, and the linking agent for derivatizing the carrier protein is γ-maleimidobutyric acid N-hydroxysuccinimide ester (GMBS) or succinimidyl-3 (bromoacetamido) propionate (SBAP).

29. The method as claimed in claim 25 further comprising adding an adjuvant to the conjugate to form a composition.

30. A method to induce cross reactive antibodies against *S. aureus* strains in an individual at risk of *S. aureus* infection comprising administering to said individual a composition comprising a conjugate as claimed in claim 1 or a composition comprising a conjugate according to claim 1, and an adjuvant.

31. The method as claimed in claim 30, wherein the cross reactive antibodies bind to a *S. aureus* type 336 strain.

32. The method as claimed in claim 31 wherein the cross reactive antibodies further bind to the Wood 46 strain of *S. aureus* deposited under ATCC number 10832 and the Newman D2C strain of *S. aureus* deposited under ATCC number 25904.

* * * * *